United States Patent
Straus

(10) Patent No.: US 10,000,788 B2
(45) Date of Patent: Jun. 19, 2018

(54) RAPID AND SENSITIVE DETECTION OF MOLECULES

(75) Inventor: Don Straus, Cambridge, MA (US)

(73) Assignee: First Light Biosciences, Inc., Bedford, MA (US)

( * ) Notice: Subject to any disclaimer, the term of this patent is extended or adjusted under 35 U.S.C. 154(b) by 2435 days.

(21) Appl. No.: 10/236,105

(22) Filed: Sep. 6, 2002

(65) Prior Publication Data

US 2003/0143580 A1   Jul. 31, 2003

Related U.S. Application Data

(60) Provisional application No. 60/317,658, filed on Sep. 6, 2001.

(51) Int. Cl.
*C12Q 1/00*   (2006.01)
*C12Q 1/06*   (2006.01)
(Continued)

(52) U.S. Cl.
CPC ............... *C12Q 1/06* (2013.01); *B82Y 20/00* (2013.01); *C12Q 1/04* (2013.01); *C12Q 1/18* (2013.01);
(Continued)

(58) Field of Classification Search
USPC ........ 436/169, 172, 531–534, 525–526, 523; 422/82, 82.07, 82.08; 209/576–582, 636;
(Continued)

(56) References Cited

U.S. PATENT DOCUMENTS 2,672,431 A   3/1954   Goetz
2,761,813 A   9/1956   Goetz
(Continued)

FOREIGN PATENT DOCUMENTS

AU          760425 B2    3/2000
CN       101254482 A    9/2008
(Continued)

OTHER PUBLICATIONS

PerkinElmer, Inc., GeneScreen™ hybridization transfer membranes, Application Notes, available at <http://las.perkinelmer.com/> (retrieved Feb. 27, 2007).*
(Continued)

*Primary Examiner* — Melanie Yu Brown
*Assistant Examiner* — Richard Moerschell
(74) *Attorney, Agent, or Firm* — Clark & Elbing LLP

(57) ABSTRACT

The invention features methods for rapidly and sensitively identifying molecular targets in medical, industrial, and environmental samples. The invention labels target molecules and then images them using large area imaging. Diagnostic tests based on the invention can be rapid, ultra-sensitive, quantitative, multiplexed, and automated. A broad range of infectious agents (e.g., bacteria, viruses, fungi, and parasites) and molecules (e.g., proteins, DNA, RNA, hormones, and drugs) can be detected by the methods. The invention enables rapid, ultra-sensitive, cost-effective, and portable assays. The ability of the invention to detect low levels of target molecules rapidly and cost-effectively results from the combination of high intensity labeling, formats that facilitate rapid reaction kinetics, and large area imaging based using either instrumentation made from off-the-shelf commercial components or no instrumentation at all.

110 Claims, 19 Drawing Sheets

Detecting individual labeling particles using a CCD array.

(51) Int. Cl.
| | |
|---|---|
| *B82Y 20/00* | (2011.01) |
| *C12Q 1/04* | (2006.01) |
| *C12Q 1/18* | (2006.01) |
| *G01N 33/50* | (2006.01) |
| *G01N 33/569* | (2006.01) |
| *G01N 33/58* | (2006.01) |
| *G01N 15/14* | (2006.01) |
| *G01N 21/64* | (2006.01) |
| *B82Y 5/00* | (2011.01) |
| *B82Y 10/00* | (2011.01) |

(52) U.S. Cl.
CPC ..... *G01N 15/1429* (2013.01); *G01N 21/6428* (2013.01); *G01N 33/5005* (2013.01); *G01N 33/5008* (2013.01); *G01N 33/56916* (2013.01); *G01N 33/56938* (2013.01); *G01N 33/56966* (2013.01); *G01N 33/56983* (2013.01); *G01N 33/58* (2013.01); *G01N 33/582* (2013.01); *B82Y 5/00* (2013.01); *B82Y 10/00* (2013.01); *G01N 15/1475* (2013.01); *G01N 2015/1488* (2013.01); *G01N 2021/6439* (2013.01); *G01N 2021/6471* (2013.01); *G01N 2333/195* (2013.01); *G01N 2333/245* (2013.01); *G01N 2333/31* (2013.01); *G01N 2333/32* (2013.01); *G01N 2333/33* (2013.01)

(58) Field of Classification Search
USPC .................................. 356/335–343, 72, 73
See application file for complete search history.

(56) References Cited

U.S. PATENT DOCUMENTS

| | | | |
|---|---|---|---|
| 3,694,317 A | 9/1972 | Scher | |
| 3,981,776 A | 9/1976 | Saxholm | |
| 4,097,586 A | 6/1978 | Gross | |
| 4,098,876 A | 7/1978 | Piasio et al. | |
| 4,115,535 A | 9/1978 | Giaever | |
| 4,125,375 A | 11/1978 | Hunter | |
| 4,129,419 A | 12/1978 | Hermann, Jr. | |
| 4,141,687 A | 2/1979 | Forrest et al. | |
| 4,157,323 A | 6/1979 | Yen et al. | |
| 4,177,253 A | 12/1979 | Davies et al. | |
| 4,222,744 A | 9/1980 | McConnell | |
| 4,436,826 A | 3/1984 | Wang | |
| 4,438,068 A | 3/1984 | Forrest | |
| 4,454,233 A | 6/1984 | Wang | |
| 4,455,370 A * | 6/1984 | Bartelsman et al. | 435/6 |
| 4,477,578 A | 10/1984 | Miles et al. | |
| 4,537,861 A | 8/1985 | Elings et al. | |
| 4,562,157 A | 12/1985 | Lowe et al. | |
| 4,565,783 A | 1/1986 | Hansen et al. | |
| 4,582,810 A | 4/1986 | Rosenstein | |
| 4,587,213 A | 5/1986 | Malecki | |
| 4,614,585 A | 9/1986 | Mehra et al. | |
| 4,693,972 A | 9/1987 | Mansour et al. | |
| 4,731,337 A | 3/1988 | Luotola et al. | |
| 4,745,077 A | 5/1988 | Holian et al. | |
| 4,777,137 A | 10/1988 | Lemonnier | |
| 4,777,145 A * | 10/1988 | Luotola et al. | 436/526 |
| 4,912,037 A | 3/1990 | Lemonnier et al. | |
| 4,922,092 A | 5/1990 | Rushbrooke et al. | |
| 4,959,301 A | 9/1990 | Weaver et al. | |
| 4,988,302 A | 1/1991 | Smith et al. | |
| 4,988,618 A | 1/1991 | Li et al. | |
| 5,073,497 A | 12/1991 | Schwartz | |
| 5,089,413 A | 2/1992 | Nelson et al. | |
| 5,137,812 A | 8/1992 | Matner | |
| 5,190,666 A | 3/1993 | Bisconte | |
| 5,232,838 A | 8/1993 | Nelson et al. | |
| 5,238,810 A | 8/1993 | Fujiwara et al. | |
| 5,258,284 A * | 11/1993 | Morris et al. | 435/6 |
| 5,262,526 A * | 11/1993 | Sasamoto et al. | 534/551 |
| 5,292,644 A | 3/1994 | Berg | |
| 5,306,420 A | 4/1994 | Bisconte | |
| 5,321,545 A | 6/1994 | Bisconte | |
| 5,355,215 A | 10/1994 | Schroeder et al. | |
| 5,366,867 A | 11/1994 | Kawakami et al. | |
| 5,464,749 A | 11/1995 | Schwarzberg et al. | |
| 5,474,910 A | 12/1995 | Alfano | |
| 5,510,246 A | 4/1996 | Morgan | |
| 5,538,857 A * | 7/1996 | Rosenthal et al. | 435/15 |
| 5,541,069 A * | 7/1996 | Mortensen et al. | 435/7.9 |
| 5,552,272 A | 9/1996 | Bogart | |
| 5,558,839 A | 9/1996 | Matte et al. | |
| 5,582,982 A | 12/1996 | Cubbage et al. | |
| 5,585,241 A | 12/1996 | Lindmo | |
| 5,604,351 A | 2/1997 | Bisconte | |
| 5,606,413 A * | 2/1997 | Bellus et al. | 356/326 |
| 5,624,850 A | 4/1997 | Kumar et al. | |
| 5,652,939 A | 7/1997 | Verlinden et al. | |
| 5,653,939 A * | 8/1997 | Hollis et al. | 506/3 |
| 5,663,057 A | 9/1997 | Drocourt et al. | |
| 5,672,880 A | 9/1997 | Kain | |
| 5,681,530 A * | 10/1997 | Kuster et al. | 422/63 |
| 5,681,712 A | 10/1997 | Nelson | |
| 5,694,478 A | 12/1997 | Braier et al. | |
| 5,705,402 A | 1/1998 | Leland et al. | |
| 5,736,405 A * | 4/1998 | Alfano et al. | 436/55 |
| 5,744,322 A | 4/1998 | Krejcarek et al. | |
| 5,766,868 A | 6/1998 | Seto | |
| 5,792,617 A | 8/1998 | Rotman | |
| 5,814,454 A * | 9/1998 | Ju | 435/6 |
| 5,821,066 A | 10/1998 | Pyle | |
| 5,828,716 A | 10/1998 | Bisconte de Saint Julien | |
| 5,843,766 A | 12/1998 | Applegate et al. | |
| 5,852,498 A | 12/1998 | Youvan et al. | |
| 5,861,270 A | 1/1999 | Nelis | |
| 5,891,394 A | 4/1999 | Drocourt et al. | |
| 5,914,245 A | 6/1999 | Bylina et al. | |
| 5,958,790 A | 9/1999 | Cerny | |
| 5,968,766 A | 10/1999 | Powers | |
| 5,976,892 A | 11/1999 | Bisconte | |
| 5,981,180 A | 11/1999 | Chandler et al. | |
| 5,985,675 A | 11/1999 | Charm et al. | |
| 5,989,835 A | 11/1999 | Dunlay et al. | |
| 5,993,740 A | 11/1999 | Niiyama et al. | |
| 6,048,723 A | 4/2000 | Banes | |
| 6,051,395 A | 4/2000 | Rocco | |
| 6,121,055 A | 9/2000 | Hargreaves | |
| 6,122,396 A | 9/2000 | King et al. | |
| 6,130,931 A | 10/2000 | Laurila et al. | |
| 6,140,653 A | 10/2000 | Che | |
| 6,165,742 A | 12/2000 | Ofjord et al. | |
| 6,171,180 B1 | 1/2001 | Pham et al. | |
| 6,171,780 B1 | 1/2001 | Pham et al. | |
| 6,200,762 B1 * | 3/2001 | Zlokarnik et al. | 435/7.1 |
| 6,214,560 B1 | 4/2001 | Yguerabide et al. | |
| 6,258,326 B1 | 7/2001 | Modlin | |
| 6,259,807 B1 | 7/2001 | Ravkin | |
| 6,268,222 B1 | 7/2001 | Chandler et al. | |
| 6,274,384 B1 | 8/2001 | Starzl et al. | |
| 6,306,589 B1 | 10/2001 | Muller et al. | |
| 6,309,822 B1 * | 10/2001 | Fodor et al. | 506/9 |
| 6,345,115 B1 | 2/2002 | Ramm et al. | |
| 6,358,730 B1 | 3/2002 | Kane | |
| 6,472,166 B1 | 10/2002 | Wardlaw et al. | |
| 6,582,912 B1 | 6/2003 | Rousseau et al. | |
| 6,623,983 B1 * | 9/2003 | Terstappen et al. | 436/526 |
| 6,664,528 B1 | 12/2003 | Cartlidge et al. | |
| 6,710,879 B1 | 3/2004 | Hansen et al. | |
| 6,727,071 B1 | 4/2004 | Dunlay et al. | |
| 6,764,648 B1 | 7/2004 | Roach et al. | |
| 6,852,527 B2 | 2/2005 | Chan et al. | |
| 6,919,960 B2 | 7/2005 | Hansen et al. | |
| 7,068,365 B2 | 6/2006 | Hansen et al. | |
| 7,110,585 B2 | 9/2006 | Cork et al. | |
| 7,160,687 B1 | 1/2007 | Kapur et al. | |
| 7,582,415 B2 | 9/2009 | Straus | |
| 7,763,405 B2 | 7/2010 | Wu et al. | |
| 7,820,430 B2 | 10/2010 | Weng et al. | |
| 8,021,848 B2 | 9/2011 | Straus | |

(56) References Cited

U.S. PATENT DOCUMENTS

| | | | |
|---|---|---|---|
| 9,090,462 | B2 | 7/2015 | Straus |
| 9,290,382 | B2 | 3/2016 | Straus |
| 2001/0039060 | A1 | 11/2001 | Siiman et al. |
| 2002/0028471 | A1 | 3/2002 | Oberhardt |
| 2002/0055092 | A1 | 5/2002 | Hochman |
| 2002/0137106 | A1 | 9/2002 | Leung et al. |
| 2003/0068638 | A1 | 4/2003 | Cork et al. |
| 2003/0082516 | A1 | 5/2003 | Straus |
| 2003/0170613 | A1 | 9/2003 | Straus |
| 2004/0048395 | A1 | 3/2004 | Lee et al. |
| 2004/0171121 | A1 | 9/2004 | Leppla et al. |
| 2004/0172000 | A1 | 9/2004 | Roe et al. |
| 2004/0246483 | A1 | 12/2004 | Hansen et al. |
| 2005/0013737 | A1 | 1/2005 | Chow et al. |
| 2005/0148085 | A1 | 7/2005 | Larsen |
| 2005/0191687 | A1 | 9/2005 | Wang et al. |
| 2005/0220670 | A1 | 10/2005 | Palmieri et al. |
| 2005/0221403 | A1 | 10/2005 | Gazenko |
| 2005/0225766 | A1 | 10/2005 | Hansen et al. |
| 2005/0226779 | A1 | 10/2005 | Oldham et al. |
| 2006/0006067 | A1 | 1/2006 | Unger |
| 2006/0051816 | A1 | 3/2006 | Hsieh et al. |
| 2006/0121055 | A1 | 6/2006 | Campbell et al. |
| 2006/0129327 | A1 | 6/2006 | Kim et al. |
| 2006/0188967 | A1 | 8/2006 | Nalin et al. |
| 2006/0210435 | A1 | 9/2006 | Alavie et al. |
| 2006/0216696 | A1 | 9/2006 | Goguen |
| 2006/0256340 | A1 | 11/2006 | Hansen et al. |
| 2006/0292552 | A1 | 12/2006 | Haquette et al. |
| 2007/0014695 | A1 | 1/2007 | Yue et al. |
| 2007/0172899 | A1 | 7/2007 | Graham et al. |
| 2007/0184546 | A1 | 8/2007 | Farrelly et al. |
| 2007/0212681 | A1 | 9/2007 | Shapiro et al. |
| 2007/0212747 | A1 | 9/2007 | Browne et al. |
| 2008/0003571 | A1 | 1/2008 | McKernan et al. |
| 2008/0014576 | A1 | 1/2008 | Jovanovich et al. |
| 2008/0032328 | A1 | 2/2008 | Cline et al. |
| 2008/0038738 | A1 | 2/2008 | Weigum et al. |
| 2008/0200343 | A1 | 8/2008 | Clemens et al. |
| 2008/0206099 | A1 | 8/2008 | Aruga et al. |
| 2009/0315987 | A1 | 12/2009 | Straus |
| 2010/0248281 | A1 | 9/2010 | Straus |
| 2012/0045826 | A1 | 2/2012 | Yantz et al. |
| 2012/0046203 | A1 | 2/2012 | Walsh et al. |
| 2012/0149007 | A1 | 6/2012 | Abrams et al. |
| 2013/0011566 | A1 | 1/2013 | Colin et al. |

FOREIGN PATENT DOCUMENTS

| | | | |
|---|---|---|---|
| DE | 19608320 A1 | 8/1997 | |
| DE | 19631997 | 2/1998 | |
| DE | 19940810 A1 | 5/2000 | |
| EP | 0171174 A2 | 2/1986 | |
| EP | 0574977 | 12/1993 | |
| EP | 0753732 A2 | 1/1997 | |
| EP | 1207394 | 5/2002 | |
| EP | 1508374 A2 | 2/2005 | |
| JP | S62-501647 A | 7/1987 | |
| JP | H02-502405 A | 8/1990 | |
| JP | 3102240 A | 4/1991 | |
| JP | H3-83598 | 4/1991 | |
| JP | 10-295362 A | 11/1998 | |
| JP | H11-346795 | 12/1999 | |
| JP | 2000-509827 A | 8/2000 | |
| JP | 2001-224355 | 8/2001 | |
| JP | 2001-512875 A | 8/2001 | |
| JP | 2002-125656 A | 5/2002 | |
| JP | 2003-294596 A | 10/2003 | |
| JP | 2006-087336 A | 4/2006 | |
| JP | 2006-162466 A | 6/2006 | |
| JP | 2007-526807 A | 9/2007 | |
| JP | 2008-513022 A | 5/2008 | |
| JP | 2009-513111 A | 4/2009 | |
| WO | WO 83/01581 | 5/1983 | |
| WO | WO-86/04684 A1 | 8/1986 | |
| WO | WO-89/05456 A1 | 6/1989 | |
| WO | WO-97/40181 A1 | 10/1997 | |
| WO | WO 9744664 A1 * | 11/1997 | |
| WO | WO 98/38490 | 9/1998 | |
| WO | WO 98/50577 | 11/1998 | |
| WO | WO 99/08233 | 2/1999 | |
| WO | WO 9920789 A1 * | 4/1999 | |
| WO | WO99/35483 | 7/1999 | |
| WO | WO99/36577 | 7/1999 | |
| WO | WO 9958948 A2 * | 11/1999 | |
| WO | WO 0004382 A1 * | 1/2000 | |
| WO | WO 0047766 A1 * | 8/2000 | |
| WO | WO 01/57522 | 8/2001 | |
| WO | WO 01/61348 | 8/2001 | |
| WO | WO-03/073817 A2 | 9/2003 | |
| WO | WO-2005/082254 A2 | 9/2005 | |
| WO | WO-2006/032044 A2 | 3/2006 | |
| WO | WO-2007/038478 A2 | 4/2007 | |
| WO | WO-2008/005998 A2 | 1/2008 | |
| WO | WO-2010/036808 A1 | 4/2010 | |
| WO | WO-2010/036827 A1 | 4/2010 | |
| WO | WO-2010/036829 A1 | 4/2010 | |
| WO | WO-2011/117545 A1 | 9/2011 | |
| WO | WO-2013/070730 A2 | 5/2013 | |
| WO | WO-2013/158666 A1 | 10/2013 | |

OTHER PUBLICATIONS

Definition and Procedure for the Determination of the Method Detection Limit, Appendix B to 40 C.F.R. § 136, available at http://www.access.gpo.gov (retrieved Nov. 20, 2007). pp. 343-346.*

Susa et al., "Legionella pneumophila infection in intratracheally inoculated T cell-depleted or -nondepleted A/J mice", J. Immunol., 1998, vol. 160, pp. 316-321.*

Thomas et al., "Making gold nanoparticles glow: enhanced emission from a surface-bound fluoroprobe", J. Am. Chem. Soc., 2000, vol. 122, pp. 2655-2656.*

Patterson, RB (1966) SPIE.*

Crowther (2000) Method in Mol Biol vol. 149.*

Batchelor (2012) Machine Vision Handbook.*

Yasui (1997) App Env Micro 63:4528-4533 (Year: 1997).*

Lamture et al., "Direct Detection of Nucleic Acid Hybridization on the Surface of a Charge Coupled Device," Nucleic Acids Res. 22 (11):2121-5 (1994).

Rousseau A., "New Miniaturized Highly Sensitive Immunoassay Device for Quantitative Measurement of Soluble or Particular Antigen or Antibodies in a Liquid Sample," Clinical Chemistry 45 (9):1685-7 (1999).

Schultz S., "Single target Molecule Detection with Nonbleaching Multicolor Optical Immunolabels," PNAS 97 (3):996-01 (2000).

Al-Hakiem MH et al., "Development of Fluoroimmunassays for the Determination of Individual or Combined Levels of Procainamide and N-acetylprocainamide in serum." *J Immunoassay* 3(1): 91-110 (1982).

Allman et al., "Fluoroimmunoassay of Progesterone in Human Serum or Plasma" *Clin Chem* 27(7): 1176-1179 (1981).

Corkidi et al., "COVASIAM: an Image Analysis Method That Allows Detection of Confluent Microbial Colonies and Colonies of Various Sizes for Automated Counting," Appl Environ. Microbiol. 1998 vol. 64(4) pp. 1400-1404.

Kamentsky, L., "Laser Scanning Cytometry," *In Cytometry*, Z. Darzynkiewicz, H. Crissman, and J. Robinsnon, eds. (San Diego: Academic Press), (2001) pp. 51-87.

Logtenberg, T. et al., "Enumeration of (auto)antibody producing cells in human using the "spot—ELISA"," *Immunol Lett* 9, (1985) pp. 343-347.

Masuko, M. et al., "A novel method for detection and counting of single bacteria in a wide field using an ultra-high-sensitivity TV camera without a microscope," *FEMS Microbiol Lett* 81, (1991) pp. 287-290.

Masuko, M. et al., "Rapid detection and counting of single bacteria in a wide field using a photon-counting TV camera," *FEMS Microbiol Lett* 83, (1991) pp. 231-238.

(56) References Cited

OTHER PUBLICATIONS

Mignon-Godefroy, K. et al., "Solid phase cytometry for detection of rare events," *Cytometry* 27, (1997) pp. 336-344.
Miraglia, S., "Homogeneous cell-and bead-based assays for high throughput screening using fluorometric microvolume assay technology," *Journal of Biomolecular Screening* 4, (1999) pp. 193-204.
Nargessi et al., "Magnetizable Solid-Phase Fluoroimmunoassay of Thyroxine by a Sequential Addition Technique." *Clin Chem* 26(12): 1701-1703 (1980).
Nargessi et al., "Immunoassays for Serum C-reactive Protein Employing Fluorophore-labelled reactants." *Journal Immunol Methods* 71(1): 17-24 (1984).
Tibbe, A., "Optical tracking and detection of immunomagnetically selected and aligned cells," *Nature Biotechnology* 17, (1999) pp. 1210-1213.
Viinikka L. et al., "A Two-site Immunofluorometric Assay for Human Placental Lactogen." *Clin Chim Acta.* 114(1):1-9 (1981).
Wellman et al. "Magnetically-assisted Transport Evanescent Field Fluoroimmunoassay" *Anal Chem.* 78(13): 4450-6 (2006).
Yasui, T. et al., "Imaging of Lactobacillus brevis single cells and microcolonies without a microscope by an ultrasensitive chemiluminescent enzyme immunoassay with a photon-counting television camera," *Appl. Environ. Microbiol.* 63, (1997) pp. 4528-4533.
Zhao et al., "Competitive Immunoassay for Microliter Protein Samples with Magnetic Beads and Near-infrared Fluorescence Detection." *Anal Chem* 76(7): 1871-6 (2004).
Anonymous, The Brain, Enchanted Learning.com, http://www.enchantedlearning.com/subjects/anatomy/brain.neuron.html, copyright 2001-2007, printed Nov. 4, 2007, pp. 1-4.
Colony Counter (http://www.topac.com/acolyte.html), downloaded Apr. 12, 2005, p. 1-3.
Colony Counter Models and Specifications (http://biologics-inc.com/cc-models.htm), downloaded Apr. 15, 2005, p. 1-3.
Digital Multi-Purpose High-Resolution Colony and Plaque Counter (http://www.loats.com/mla.html), downloaded Apr. 12, 2005, p. 1-3.
Esteban et al., "Improved Direct Epifluorescent Filter Technique for Rapid Bioburden Control in Intravenous Solutions," *J. Parenter. Sci. Technol.* 46:146-149 (1992).
Frost, "Improved Technic for the Micro or Little Plate Method of Counting Bacteria in Milk," p. 176-184 (1920).
Loats et al., "LAI High-Resolution Automated Copy Colony Counting System—Mouse Lymphoma Assay: Performance Analysis," (http://loats.com/docs/HRCCval/HRCCval/HRCCval/HRCCval.html), p. 1-11 (1990).
System Specifications (http://www.loats.com/order_info.html), p. 1-7 (1999).
Technical Specification (http://www.perceptive.co.uk/products/scc/techspec.html), downloaded Apr. 12, 2005, p. 1-2.
Wilson et al., "Use of the IUL Countermat Automatic Colony Counter for Spiral Plated Total Viable Counts," *Appl. Environ. Microbiol.* 61:3158-3160 (1995).
Wolniak et al., 2004. BSCI 427 Principles of Microscopy Fall 2004 Syllabus, (http://www.life.umd.edu/cbmg/faculty/wolniak /wolniac/micro.html), printed Nov. 8, 2007, p. 1-8.
International Search Report for PCT/US2002/28411, completed Nov. 25, 2002, dated Mar. 14, 2003.
International Preliminary Report on Patentability for PCT/US2002/28411, completed Jul. 13, 2004.
"Innovative Plate Holder for Colony Counter," downloaded from http://www.laboratorytalk.com on Oct. 16, 2002 (2 pages).

"Innovative Plate Holder for ProtoCOL," downloaded from http://www.synbiosis.com on Oct. 16, 2002 (2 pages).
Moore et al, "Lymphocyte fractionation using immunomagnetic colloid and a dipole magnet flow cell sorter," *Journal of Biochemical and Biophysical Methods* 37:11-33 (1998).
Sorcerer Automated Colony Counting, Perceptive Instruments, 2 pages, 2002.
Vidon et al. "A simple chemiluminescence-based method for rapid enumeration of *Listeri* spp. microcolonies", Journal of Applied Microbiology, 90:988-993 (2001).
Nelis et al. "Enzymatic detection of coliforms and *Escherichia coli* within 4 hours" Water Air and Soil Pollution, 123:43-52 (2000).
Van Poucke et al. "Rapid detection of fluorescent and chemiluminescent total coliforms and *Escherichia coli* on membrane filters" Journal of Microbiological Methods, 42:233-244 (2000).
Van Poucke et al.. "A 210-min solid phase cytometry test for the enumeration of *Escherichia coli* in drinking water", Journal of Applied Microbiology, 89:390-396 (2000).
Kroll et al. "A Laser-Light Pulse Counting Method for Automatic and Sensitive Counting of Bacteria Stained with Acridine Orange", Journal of Applied Bacteriology, 66:161-168 (1989).
Van Poucke et al. "Solid phase cytometry-based enzymatic detection of coliforms in drinking water within 4 h", Water Supply 17:67-72 (1999).
Thomas et al, "Making Gold Nanoparticles Glow: Enhanced Emission from a Surface-Bound Fluoroprobe," *J. Am. Chem. Soc.* 122: 2655-2656, 2000.
Gray et al., "Identification of micro-organisms after milliflex rapid detection—a possibility to identify nonsterile findings in the milliflex rapid sterility test," PDA J Pharm Sci Technol. 65(1):42-54 (2011).
Freydiere et al., "Detection of salmonellae by using Rambach agar and by a C8 esterase spot test," J Clin Microbiol. 29(10):2357-9 (1991).
Porter et al., "The use of DAPI for identifying and counting aquatic microflora," Limnol Oceanogr. 25(5):943-8 (1980).
Findlay et al., "Automated closed-vessel system for in vitro diagnostics based on polymerase chain reaction," Clin Chem. 39(9):1927-33 (1993).
Sage et al., "A rapid and nondestructive method for microbiological testing in pharmaceutical manufacturing." American Biotechnology Laboratory. 1-5 (2006).
London et al., "An Automated System for Rapid Non-Destructive Enumeration of Growing Microbes," PLoS One 5(1):e8609 (16 pages) (2010).
Nealson, "Isolation, identification, and manipulation of luminous bacteria," *Methods Enzymol* 57:153-166, 1978.
Watanabe et al., "Analysis of synchronous photon emissions from the bacterium Photobacterium phosphoreum during colony formation from a single cell," *J. Biolumin. Chemilumin.* 6:13-18, 1991.
Watanabe et al., "Bioluminescence and cell growth of Photobacterium phosphoreum," *J. Biochem.* 88(3):815-817, 1980.
CCD detectors (http://www.astrosurf.com/re/chip.html) published online Feb. 22, 2001 (from web archive: http://www.web.archive.org/web/20010222014106/http://www.astrosurf.com/re/chip.html), retrieved Apr. 12, 2012 (5 pages).
Texas Instruments TC211 192×165 Pixel CCD Image Sensor description dated Jan. 1990 (13 pages).
U.S. Appl. No. 15/057,393, Straus.

* cited by examiner

FIG. 1. Detecting individual labeling particles using a CCD array.

Testing a blood sample for a protein in a microtiter well format.

FIG. 3. A CCD imaging device for large area imaging.

FIG. 4. A CCD imaging system for non-magnified large area imaging.

FIG. 5. Detecting individual microscopic labeling particles without magnification using electronic, instant film, and unaided visual detection (Example 1).

FIG. 6. An ultra-sensitive lateral flow test for detecting low numbers of bacteria using non-magnified large area imaging (Example 2).

FIG. 7. An ultra-sensitive lateral flow test for detecting low levels of protein using non-magnified large area imaging (Example 3).

FIG. 8. Ultra-sensitive lateral flow test for detecting low levels of protein in serum using non-magnified large area imaging (Example 4).

FIG. 9. Ultra-sensitive lateral flow test for multiplex detection of a protein and a bacterium using non-magnified large area imaging (Example 5).

Ultra-sensitive chemiluminescent lateral flow test for detecting low levels of protein using instant film (Example 7).

FIG. 11. Schematic of a test device that uses capture threads to select target molecule:labeling particle complexes (Example 8).

FIG. 12. An ultra-sensitive test for a protein using the capture thread format (Example 8).

FIG. 13. Sensitive detection of protein molecules using non-magnified large area imaging and solid-phase capture immunoassay (Example 9).

FIG. 14. Sensitive detection of protein molecules using non-magnified large area imaging and liquid-phase capture (Example 10).

Immunoassay for detecting multiple human cytokines using non-magnified large area imaging (Example 11).

Competitive immunoassay for total (bound plus free) cytokine IL-2 using non-magnified large area imaging (Example 12).

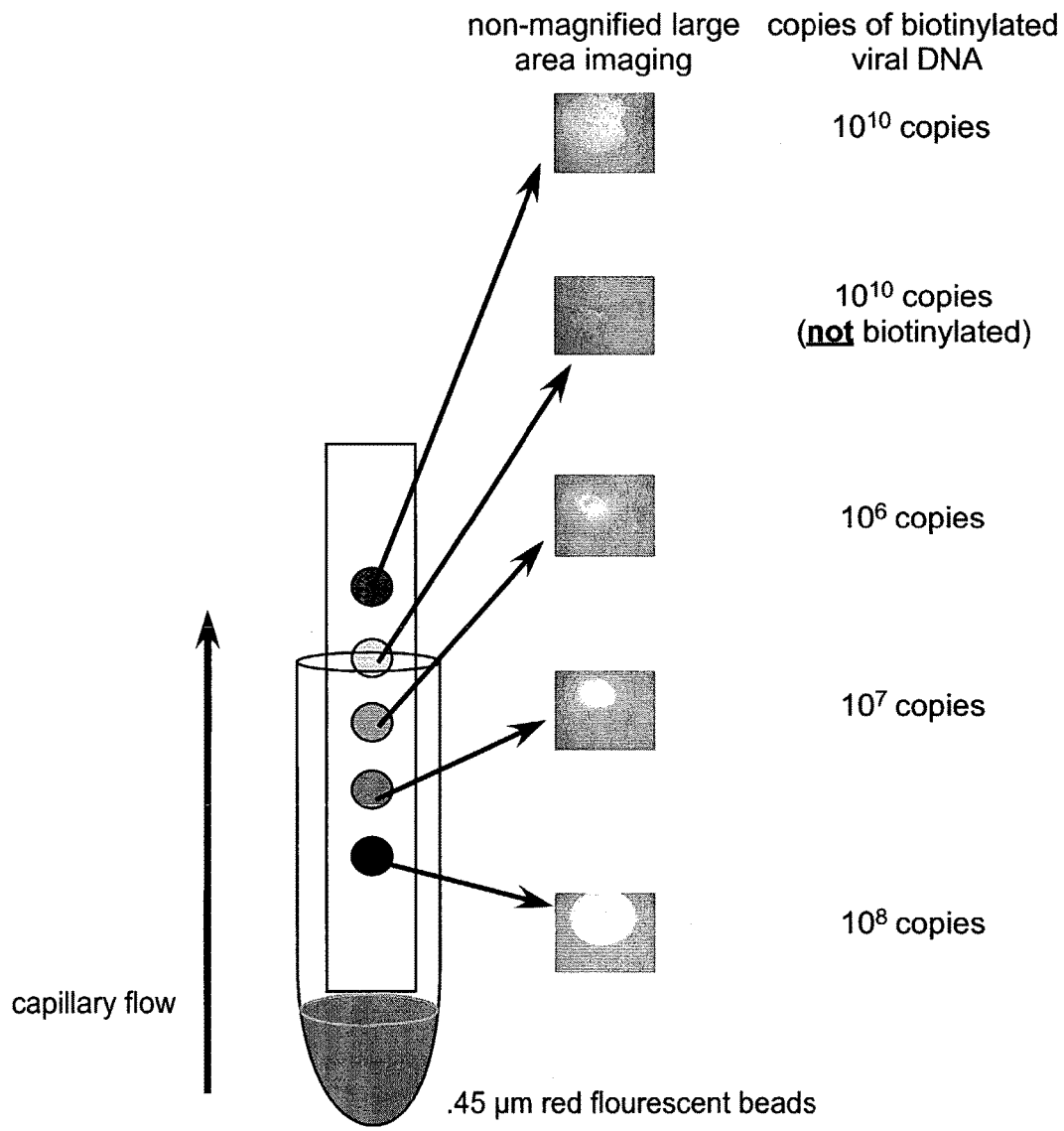
FIG. 17. Sensitive detection of nucleic acid molecules using a dipstick format and non-magnified large area imaging (Example 13).

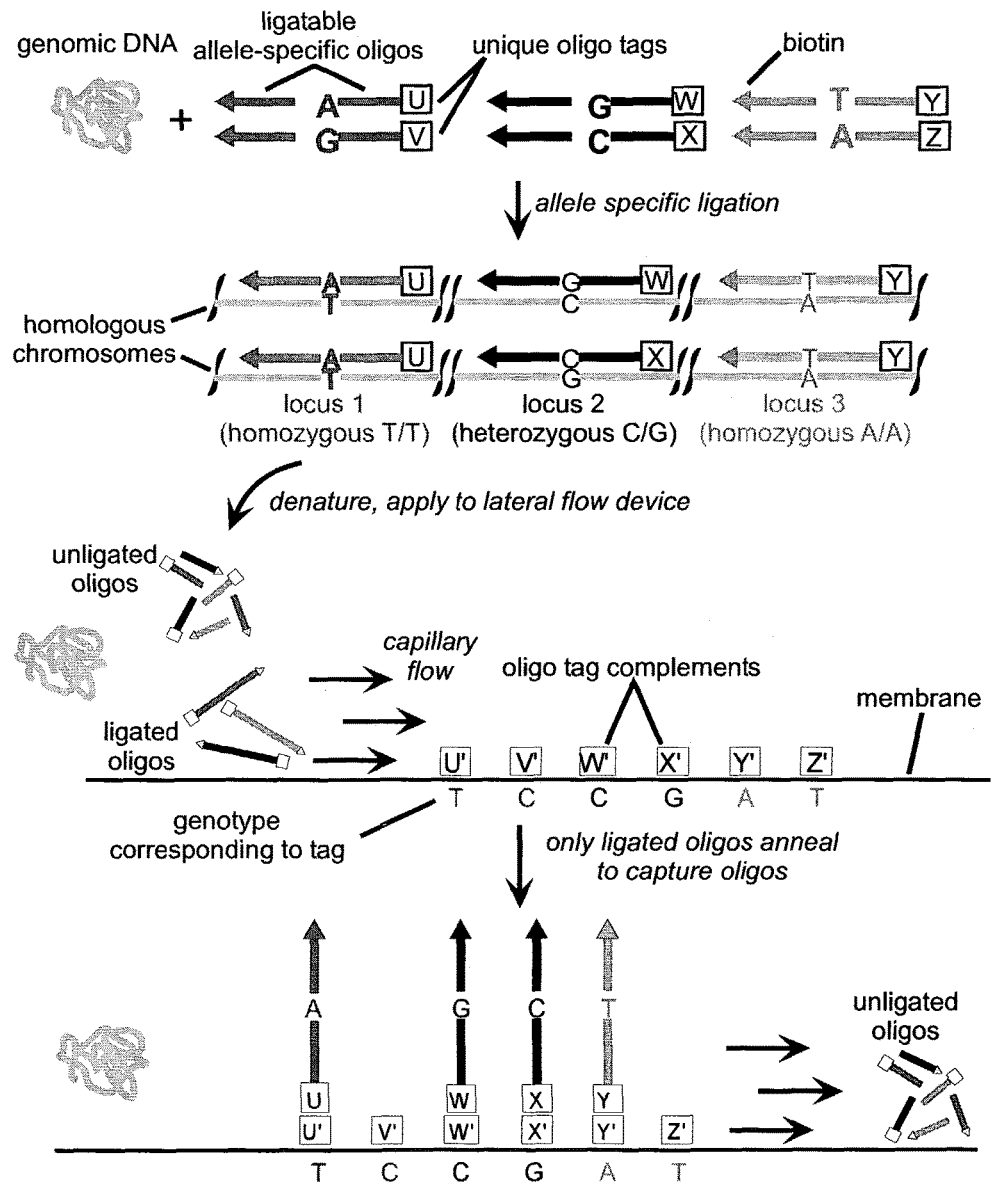
FIG. 18. Non-amplified multiplex SNP analysis using a lateral flow format and non-magnified large area imaging: Oligonucleotide ligation and sample application (Example 15).

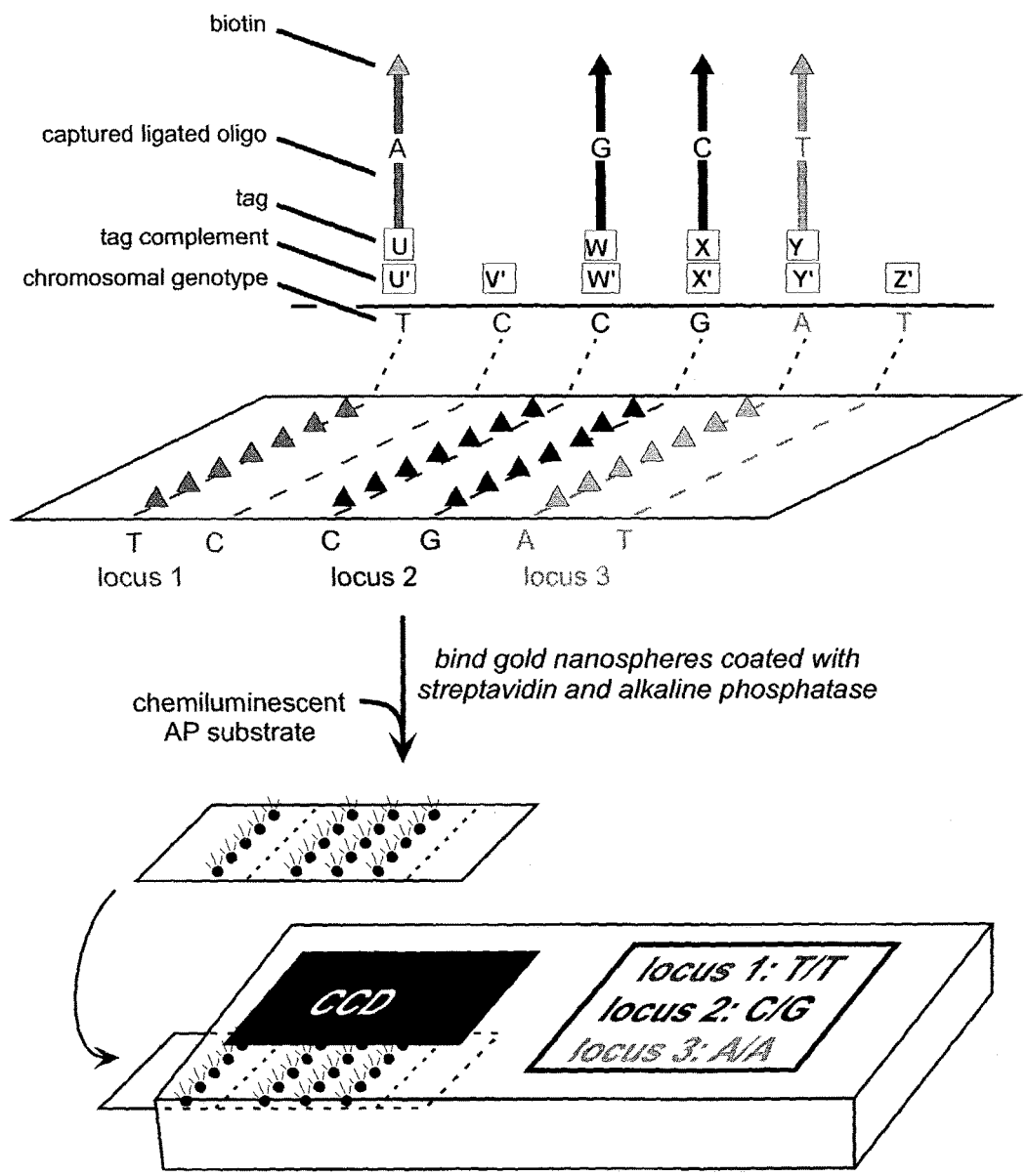
FIG. 19. Non-amplified multiplex SNP analysis using a lateral flow format and non-magnified large area imaging: Detection (Example 15).

SEQUENCE LISTING

```
<160> NUMBER OF SEQ ID NOS: 20

<210> SEQ ID NO 1
<211> LENGTH: 16
<212> TYPE: DNA
<213> ORGANISM: Homo sapiens

<400> SEQUENCE: 1
gggccccccc tcgatc                                                    16

<210> SEQ ID NO 2
<211> LENGTH: 18
<212> TYPE: DNA
<213> ORGANISM: Homo sapiens

<400> SEQUENCE: 2
atcgataccg tcgacctc                                                  18

<210> SEQ ID NO 3
<211> LENGTH: 90
<212> TYPE: DNA
<213> ORGANISM: Homo sapiens
<220> FEATURE:
<221> NAME/KEY: modified_base
<222> LOCATION: 1
<223> OTHER INFORMATION: g at position 1 has a 5' phosphate group
<220> FEATURE:
<221> NAME/KEY: misc_feature
<222> LOCATION: 90
<223> OTHER INFORMATION: n at position 90 is t-NH2

<400> SEQUENCE: 3
ggagaagtct gccgttactg cgctctagaa ctagtggatc tttttttttt tttttttttt    60
tttttttttt tttttttttt tttttttttn                                     90

<210> SEQ ID NO 4
<211> LENGTH: 90
<212> TYPE: DNA
<213> ORGANISM: Homo sapiens
<220> FEATURE:
<221> NAME/KEY: misc_feature
<222> LOCATION: 1
<223> OTHER INFORMATION: n at position 1 is t-NH2

<400> SEQUENCE: 4 ntttttttt tttttttttt tttttttttt tttttttttt tttttttttt cgctctagaa     60
ctagtggatc atggtgcacc tgactcctgt                                     90

<210> SEQ ID NO 5
<211> LENGTH: 90
<212> TYPE: DNA
<213> ORGANISM: Homo sapiens
<220> FEATURE:
<221> NAME/KEY: misc_feature
<222> LOCATION: 1
<223> OTHER INFORMATION: n at position 1 is t-NH2

<400> SEQUENCE: 5
```

```
nttttttttt tttttttttt tttttttttt tttttttttt tttttttttt cgctctagaa    60
ctagtggatc atggtgcacc tgactcctga                                      90
```

```
<210> SEQ ID NO 6
<211> LENGTH: 39
<212> TYPE: DNA
<213> ORGANISM: Homo sapiens

<400> SEQUENCE: 6
```

```
cgctctagaa ctagtggatc tggtgcacct gactcctga                            39
```

```
<210> SEQ ID NO 7
<211> LENGTH: 38
<212> TYPE: DNA
<213> ORGANISM: Homo sapiens

<400> SEQUENCE: 7
```

```
tctcgaggtc gacggtatct ggtgcacctg actcctgt                             38
```

```
<210> SEQ ID NO 8
<211> LENGTH: 38
<212> TYPE: DNA
<213> ORGANISM: Homo sapiens

<400> SEQUENCE: 8
```

```
catcgatacc gtcgacctcg ctgtgctgac catcgacg                             38
```

```
<210> SEQ ID NO 9
<211> LENGTH: 39
<212> TYPE: DNA
<213> ORGANISM: Homo sapiens

<400> SEQUENCE: 9
```

```
gcaagttcag cctggttaag gctgtgctga ccatcgaca                            39
```

```
<210> SEQ ID NO 10
<211> LENGTH: 45
<212> TYPE: DNA
<213> ORGANISM: Homo sapiens

<400> SEQUENCE: 10
```

```
gccttttgct cacatgttct tcaccattaa agaaaatatc atctt                     45
```

```
<210> SEQ ID NO 11
<211> LENGTH: 44
<212> TYPE: DNA
<213> ORGANISM: Homo sapiens

<400> SEQUENCE: 11
```

```
aaggcgatta agttgggtaa cggcaccatt aaagaaaata tcat                      44
```

```
<210> SEQ ID NO 12
<211> LENGTH: 20
<212> TYPE: DNA
<213> ORGANISM: Homo sapiens
<220> FEATURE:
<221> NAME/KEY: modified_base
<222> LOCATION: 1
<223> OTHER INFORMATION: G at position 1 has a 5' phosphate group
<220> FEATURE:
<221> NAME/KEY: modified_base
<222> LOCATION: 20
<223> OTHER INFORMATION: G at position 20 has been biotinylated

<400> SEQUENCE: 12
```
ggagaagtct gccgttactg                                              20

<210> SEQ ID NO 13
<211> LENGTH: 20
<212> TYPE: DNA
<213> ORGANISM: Homo sapiens
<220> FEATURE:
<221> NAME/KEY: modified_base
<222> LOCATION: 1
<223> OTHER INFORMATION: A at position 1 has a 5' phosphate group
<220> FEATURE:
<221> NAME/KEY: modified_base
<222> LOCATION: 20
<223> OTHER INFORMATION: T at position 20 has been biotinylated.

<400> SEQUENCE: 13
agaaagggac tgaagctgct                                              20

<210> SEQ ID NO 14
<211> LENGTH: 23
<212> TYPE: DNA
<213> ORGANISM: Homo sapiens
<220> FEATURE:
<221> NAME/KEY: modified_base
<222> LOCATION: 1
<223> OTHER INFORMATION: T at position 1 has a 5' phosphate group
<220> FEATURE:
<221> NAME/KEY: modified_base
<222> LOCATION: 22
<223> OTHER INFORMATION: A at position 22 has been biotinylated

<400> SEQUENCE: 14
tggtgtttcc tatgatgaat ata                                          23

<210> SEQ ID NO 15
<211> LENGTH: 20
<212> TYPE: DNA
<213> ORGANISM: Homo sapiens

<400> SEQUENCE: 15
gatccactag ttctagagcg                                              20

<210> SEQ ID NO 16
<211> LENGTH: 19
<212> TYPE: DNA
<213> ORGANISM: Homo sapiens

<400> SEQUENCE: 16
gataccgtcg acctcgaga                                               19

<210> SEQ ID NO 17
<211> LENGTH: 19
<212> TYPE: DNA
<213> ORGANISM: Homo sapiens

<400> SEQUENCE: 17
gaggtcgacg gtatcgatg                                               19

<210> SEQ ID NO 18
<211> LENGTH: 20
<212> TYPE: DNA
<213> ORGANISM: Homo sapiens

<400> SEQUENCE: 18
cttaaccagg ctgaacttgc                                              20

```
<210> SEQ ID NO 19
<211> LENGTH: 21
<212> TYPE: DNA
<213> ORGANISM: Homo sapiens

<400> SEQUENCE: 19
aagaacatgt gagcaaaagg c                                           21

<210> SEQ ID NO 20
<211> LENGTH: 21
<212> TYPE: DNA
<213> ORGANISM: Homo sapiens

<400> SEQUENCE: 20
gttacccaac ttaatcgcct t                                           21
```

RAPID AND SENSITIVE DETECTION OF MOLECULES

CROSS-REFERENCE TO RELATED APPLICATIONS

This application claims priority from U.S. Provisional Application No. 60/317,658, filed Sep. 6, 2001, hereby incorporated by reference.

BACKGROUND OF THE INVENTION

The invention relates to the identification of microscopic and submicroscopic targets in medical, industrial, or environmental samples.

Overview

Detecting, enumerating, and identifying low levels of molecular targets is a cornerstone of routine medical, industrial, and environmental diagnostics. For example, samples are analyzed to detect molecules from infectious agents, cancer cells, hormones, manufacturing contaminants, and pollutants.

Although numerous disparate and powerful methods for routine detection of low levels of molecules have been commercialized there are still gaps in the testing repertoire. Some of these gaps became apparent following the bioterror attacks in 2001. For example, there is an unmet need for rapid, ultra-sensitive, cost-effective, and user-friendly tests to screen simultaneously for multiple types of agents at the point of exposure. Both healthcare and industry are hampered by the lack of rapid, sensitive, and easy-to-use diagnostic tests that can be conducted on-site by non-medical personnel.

The discussion that follows focuses on routine medical diagnostics; similar methods are used for industrial and environmental applications.

Immunological Methods

Immunological tests, or immunoassays, are ubiquitous in medical diagnostics. Based on the interaction of antibodies and the corresponding targets (called antigens), immunoassays are used to detect a broad range of molecules ranging in size from small (e.g., a drug of abuse) to large (e.g., an HIV protein). Serological tests are immunological assays that, rather than testing directly for antigens, test for a host immunological response to previous exposure to the antigen—i.e., they test for the presence of host antibodies to the antigen. Numerous immunoassay systems are available ranging from large automated central lab systems to over-the-counter pregnancy tests. The tests cover a broad range of formats including agglutination assays, precipitin assays, enzyme-linked immunoassays, direct fluorescence assays, immuno-histological tests, complement-fixation assays, serological tests, immuno-electrophoretic assays, and rapid "strip" tests (e.g., lateral flow and flow through tests). Immunological tests can be extremely simple and rapid. Thus, many of the most desirable tests, those that can be conducted in a physician's office or at home by the patient, are immunological tests. One drawback of commercialized rapid immunological tests is that they are insensitive.

The need for commercially accessible sensitive immunoassays will increase in coming years. One of the first major payoffs of the human genome and proteome projects will be numerous new markers for diagnosing disease states, such as cancer, cardiovascular disease, and neurological disease. These markers may occur in trace amounts in clinical samples, such as blood, urine, and solid tissues. Commercialized rapid immunoassay tests, which are appropriate for high abundance protein markers (such as PSA, myoglobin, and antibodies, for example), may be inadequate for detecting the substantial fraction of proteins present at low concentrations.

Genetic Methods

Genetic methods are general and powerful tools for detecting and identifying nucleic acid molecules from organisms and viruses. Revolutionary new methods for ultra-sensitively detecting and distinguishing the nucleic acid content of cells and viruses based on nucleic acid amplification have recently been developed. For example, commercial tests can detect the nucleic acids from a small number of sub-microscopic HIV virus particles (e.g., 50 particles/ml). Amplification technologies include the polymerase chain reaction (PCR), ligase chain reaction (LCR), nucleic acid sequence-based amplification (NASBA), Transcription Mediated Amplification (TMA), and rolling circle amplification (RCA).

Nucleic acid amplification-based tests have several drawbacks that have hampered their exploitation in routine clinical and commercial diagnostics. The tests are generally much more expensive than microbial culture tests; require high user expertise; involve demanding sample preparation protocols; generally require a time-consuming amplification step; suffer from vulnerability to contamination and false positives; have enzymatic steps that are sensitive to inhibitors found in many clinical samples and lead to false negatives; and often have reproducibility problems in multiplexed applications. Furthermore, like microbial culture methods these methods are not well-suited to detect important classes of non-nuceic acid targets (e.g., toxins, hormones, drugs-of-abuse, and proteins).

Biochemical, Chemical, and Physical Methods

Other technologies for sensitive detection of microscopic and sub-microscopic targets include flow cytometry, mass spectroscopy, biosensors, absorbance spectroscopy, fluorescence polarization, fluorescence fluctuation spectroscopy, electrophoresis, and chromatography, among many others. Because of the expense and expertise typically required, most of these methods have remained in the province of the research laboratory.

One method that has proved useful in clinical diagnostic laboratories is flow cytometry. Flow cytometric methods are used for quantitatively detecting particular cell types on the basis of the ability to bind labeled probes (e.g., stains, antibodies, or nucleic acids). Individual cells or particles are forced to flow through a narrow channel, one at a time, past a laser beam. Fluorescence emission and size/shape information is gathered by analyzing the spectrum and light scattering caused by the organism/particle. Thousands of individual cells or particles can be analyzed per minute. For example, flow cytometry is used to quantify the population sizes of classes of lymphocytes in patients with AIDS. A highly multiplexed flow cytometric method that can detect and identify non-cellular molecules such as proteins or nucleic acids has been commercialized by Luminex (U.S. Pat. No. 5,981,180). Drawbacks of the flow cytometric method include the expense, required operator skill, inability to analyze large sample volumes (which limits sensitivity).

Biosensor technologies also hold promise for sensitive molecular detection. Biosensors use physical methods to convert a biological event, for example binding of an antibody to an antigen, to a detectable signal. One popular biosensor used for molecular detection uses surface plasmon resonance (Mullett, W. M., et al. (2000). Methods 22: 77-91). Thermo BioStar's optical immunoassay (Schultze, D., et al. (2001). Eur J Clin Microbiol Infect Dis 20: 280-3)

uses the principle of optical interference to detect binding of antigens to antibodies. The BARC biosensor technology uses magnetoresistive detection (as used for hard disk storage) of analytes tagged with single magnetic microparticles (Edelstein, R. L., et al., Biosens Bioelectron 14: 805-13, 2000).

Point-of-Care and On-Site Methods

Point-of-care tests allow professionals and consumers to perform diagnostic tests outside of dedicated central laboratories. Point-of-care diagnostics is one of the fastest growing segments in in vitro diagnostics. Typical point-of-care testing locations include the patient's bedside in hospitals; physician office labs; nursing homes; public and private health clinics; college health centers; correctional facilities; emergency vehicles; the workplace and home. Numerous point-of-care tests have been introduced in recent years and some have been extraordinarily successful. Commercialized point-of-care tests fall into several categories, those which test for: (1) metabolites (e.g., glucose and urea), inorganic molecules, drugs, and blood gases; (2) tests for macromolecules and hormones; and (3) tests for disease-causing agents (e.g., bacteria, viruses, parasites).

While very successful for analytes that occur at relatively high concentrations (e.g., blood glucose), developing point-of-care tests for low abundance target molecules has been problematic. This difficulty is largely attributable to combining two mutually antagonistic product requirements: (1) the need for sophisticated technology to meet demanding test specifications including ultra-sensitivity and (2) the need for low cost, user-friendly, and portable tests that can be operated by unskilled operators.

Some commercialized or emerging ultra-sensitive point-of-care tests are adaptations of formats used for less sensitive commercialized tests. For example, Response Biomedical Corp. has commercialized a 10-minute strip test (or lateral flow test) based on its RAMP platform, which uses fluorescently dyed microbead labels (Brooks, D. E., et al. (1999). Clin Chem 45: 1676-1678.). Similarly, Biosite's rapid strip tests detect drugs-of-abuse, cardiac markers, and infectious agents (Landry, M. L., et al. (2001). J Clin Microbiol 39: 1855-8.).

Point-of-care tests based on nucleic acid amplification have been difficult to develop because of their complexity and expense. One system is Cepheid's Smart Cycler system. Another nucleic acid amplification test for *B. anthracis* has been developed by the Mayo Clinic in collaboration with Roche (Light Cycler; Makino, S. I., et al. (2001). Lett Appl Microbiol 33: 237-40.). These systems carry both the advantages and disadvantages inherent to PCR methods. Amplification methods can deliver impressive analytical sensitivity and can be moderately rapid, for example, the Smart Cycler can deliver results in an hour (Belanger, S. D., et al. (2002). Journal of Clinical Microbiology 40: 1436-40). The analytes are limited to those containing nucleic acid (ruling out tests for protein toxins and small molecules, for example); false negatives can result from sample inhibition; highly multiplexed tests are problematic; the tests require trained personnel; and the tests are expensive.

Biosensor-based point-of-care technologies also hold promise as they can combine impressive technical specifications with low-cost and user-friendliness. For example, Thermo Biostar's OIA technology, which can test for pathogens such as influenza virus, relies on a biosensor with an optically activated surface that changes color upon binding of viral antigens because of changes in optical interference (Rodriguez, W. J., et al. (2002). Pediatr Infect Dis J 21: 193-6.).

Some of the emerging technologies focus on improved multiplexing. For example, Biosite is developing a highly parallel capillary microfluidic immunoassay system. Somalogic's technology uses aptamer arrays to analyze samples for hundreds or even thousands of analytes (Brody, E. N., et al. (1999). Mol Diagn 4: 381-8). Nanogen's NanoChip (Ewalt, K. L., et al. (2001). Anal Biochem 289: 162-72) electronic arrays are also being applied to detecting agents of bioterrorism. While tests that screen for hundreds of analytes are of clear value for drug discovery, it is less clear whether this level of multiplexing will be important for point-of-care tests.

Various new labeling/detection strategies for improving the sensitivity of point-of-care tests are also being directed towards tests for biowarfare agents. Orasure's new quantitative drugs-of-abuse tests use UPT (up-converting phosphor technology) particles (Niedbala, R. S., et al. (2001). Anal Biochem 293: 22-30.). The Navy's BARC technology uses magnetic particles and detectors to sensitively analyze samples for specific analytes (Edelstein, R. L., et al. (2000). Biosens Bioelectron 14: 805-13.). Other new labeling methods including quantum dot nanocrystals (Quantum Dot; Wang, C., et al. (2001). Science 291: 2390-2) and resonance light scattering particles (Genicon; Yguerabide, J., et al. (2001). J Cell Biochem Suppl Suppl: 71-81) could also potentially improve the sensitivity of point-of-care tests.

Unmet Needs for Molecular Diagnostics

There is a critical unmet need for efficient biowarfare agent detection by first-responders at the point-of-exposure and by routine automated scanning of building air and water supply. Similarly, because of the lack of sensitive on-site testing, clinic patients can not be sensitively tested on-site for sexually-transmitted disease pathogens, and post-surgical patients can not be quickly and sensitively screened for blood infection. The need for new technologies to address this gap may become even more acute as new diagnostic markers for diseases (including cancer, infectious disease, and cardiovascular disease) inevitably emerge from the genome and proteome projects.

SUMMARY OF THE INVENTION

The invention provides efficient methods for rapidly and sensitively identifying molecular targets in medical, industrial, and environmental samples. The invention labels target molecules and then images them using large area imaging. Diagnostic tests based on the invention can be rapid, ultra-sensitive, quantitative, multiplexed, and automated. The tests minimize sample preparation and do not require nucleic acid amplification or cell culture. A broad range of infectious agents (e.g., bacteria, viruses, fungi, and parasites) and molecules (e.g., proteins, DNA, RNA, hormones, and drugs) can be detected by the tests. Tests based on the invention can deliver the high level sensitivity of nucleic acid amplification tests, the user-friendliness and speed of immunoassays, as well as the cost effectiveness and quantification offered by microbiological tests. The invention addresses an important unmet needs in point-of-care or on-site diagnostics by enabling rapid, ultra-sensitive, cost-effective, and portable tests. Thus, the invention embodies the best attributes of the current diagnostic technologies, while filling gaps in the diagnostic repertoire.

The ability of the invention to detect low levels of target molecules rapidly and cost-effectively results from the advantages of combining high intensity labeling, formats that facilitate rapid reaction kinetics, and large area imaging based using either instrumentation made from off-the-shelf commercial components or no instrumentation at all. Table 1 lists some of some of the advantages of the invention.

TABLE 1

Selected advantages of the invention

Rapid results (<15 min)
Ultra-sensitive
Easy-to-use
Cost-effective
Multiple targets analyzed simultaneously
Scans for proteins, nucleic acids, viruses, bacteria, and parasites
Analyzes large or small volumes
Automated quantitative analysis
Portable (some embodiments)
Minimal sample preparation The invention detects low levels of target molecules by labeling them with target-specific particles or complexes that generate high-intensity signals. These complexes have two functions, affinity for specific targets and signal generation. These functions are fulfilled by the two moieties on the complexes: category-binding molecules, which bind specifically to the target molecules and signaling moieties, which are used to detect the particles. Labels that generate high intensity signals with a characteristic signature (e.g., specific wavelengths of emitted light) enable rapid and ultra-sensitive detection and also allow efficient discrimination of true positives from artifacts (e.g., fluorescent dust particles). A variety of signal generating complexes can be used including fluorescently dyed, light-scattering, quantum dot, phosphor, and enzyme-coated particles. These particles, in turn, can generate a variety of types of signals including fluorescent, chemiluminescent, and colorimetric. Similarly, a variety of category-binding molecules can be used including antibodies, nucleic acids, ligands, and aptamers.

Because the invention detects molecules, the range of targets is broad including both soluble molecules and molecules that are part of larger targets such as viruses, bacteria, or cells from animals or plants. The range of diagnostic questions that can be addressed by the invention also is broadened by the ability to use various types of target-specific molecules including antibodies, nucleic acids, aptamers, and ligands.

Detecting small numbers of target molecules in large volumes is a requirement when testing some clinical, environmental, and manufacturing samples. The invention's ability to survey large samples for low levels of target molecules rests, in part, on its ability detect individual microscopic signal generating particles without magnification. Non-magnified detection allows a large area to be surveyed for small numbers of the particles in a single image. Imaging a large area, in turn, is a key to the invention's ability to analyze large sample volumes efficiently. Detecting labeled particles in large volumes using high power microscopy or microfluidics can require challenging concentration steps or analysis of thousands of images. Methods that scan for small numbers of particles using microscopic beams become very time consuming and expensive when applied to large areas. Detection may also occur using magnification of not greater than 5×, 2×, or 1×.

Enumerating individual microscopic labels adds robustness to the results of tests based on the invention. In contrast to many large area imaging methods for analyzing molecular targets, the invention generally compares individual signals directly to small neighboring regions. This comparison improves the signal to background ratio for samples containing few labeled target molecules compared to methods that integrate the total signal and background in a large area.

Another advantage of detecting individual labeling particles is that the sensitivity of the tests can be increased without sacrificing speed by increasing the sample volume with a proportionate increase in the size of the test format (see results section of Example 8 on page 53 for an explanation).

Enumerating individual signals in a large area image also decreases the chance of false positive results. (False positive results are positive test results that occur when the actual target molecule is not present). This enumerating method is an advantage compared with methods that detect a single integrated signal, such as methods that measure the total amount of a molecule (e.g., ATP, antigens, or nucleic acids) in the sample. Any artifact that causes a signal can generate a false positive when using methods that rely on signal integration. Consider a sample that contains 482 positive signals, each of which generates 100 fluorescent units. The result of an integrative method is a single number (48,200 fluorescent units). Artifacts that generate a similar number of fluorescent units, for example, a large fluorescent dust particle may be indistinguishable. In contrast, the present invention can easily distinguish between a single large fluorescent dust particle and 482 positive signals.

Tests constructed using the invention can detect target molecules over a broad range of concentrations, from very low levels to high levels. This property of the invention, its large dynamic range, allows users to forgo the sample preparation steps (e.g., multiple dilutions) that are often required by technologies that have small dynamic ranges.

Tests based on the invention can exploit a variety of useful formats ranging from single-use strip tests that are simple, non-instrumented, and cost-effective, to sophisticated automated benchtop systems for continuous unattended environmental monitoring. Especially important is the compatibility of the invention with formats that maximize the rates of reaction during the test (e.g., the rate of binding the target molecules to the target-specific label). For example, binding reactions occur rapidly in porous membranes used by some embodiments of the invention.

Various detection methods can be used by the invention including visual, film-based, and electronic detection. The range of detection methods is an advantage for addressing a broad spectrum of diagnostic problems and testing venues. For example, for portable systems, minimizing sample and weight is an advantage. Embodiments of the invention that minimize or eliminate instrumentation are particularly useful for portability.

In certain embodiments, the labeling particles have photonic signaling character, and a colloidal or soluble substance is added to absorb the signal emitted by labeling particles that are not in the detection zone.

Other features and advantages will be apparent from the following description and the claims.

By target molecule is meant a molecule that is potentially present in a sample and whose presence is tested for by the invention. Target molecules may be distinct molecules, or they may be physically associated with other molecules, cells, or material in the sample. For example, a test for detecting the fungal pathogen *Candida albicans* might detect three different DNA sequences that are unique to the genome of the organism. These three sequences are considered to be distinct target molecules even though they are physically associated in the genome of the fungus.

By category of target molecule is meant multiple target molecules that have in common one or more features and that are considered identical for the purposes of a test constructed using the invention. For example, the category of one test could be envelope protein from the virus that causes AIDS. For example, consider a test designed to detect the envelope protein of all HIV viruses, without differentiating the HIV-1 and HIV-2 variants. In this case, the category of the target molecule includes the envelope proteins of both HIV-1 and HIV-2. The goal of another test might be to distinguish HIV-1 from HIV-2. In this case, the envelope proteins from each type of HIV would be considered a different category. Alternatively, consider the three DNA probes for C. albicans in the definition for target molecules above. If the goal of the test is to detect C. albicans, the three probes are considered identical for the purpose of the test because they share the common feature that they bind specifically to C. albicans. Therefore the three target molecules would be considered to be in the same category of target molecules.

By non-overlapping categories of target molecules is meant categories of target molecules whose union is the null set. That is, no member of any of the categories is a member of any of the other sets. For example, the categories of IL-2, thrombin, PSA, and myoglobin are non-overlapping categories.

Tests that detect and identify multiple categories generally (but not always) detect multiple non-overlapping categories of target molecules. For example, consider a test designed to identify HIV, HCV, and HBV viruses in blood. Such a test would be designed to differentiate three non-overlapping categories of target molecules, one for each of the three types of viruses.

By the categorical complexity of a test is meant the number of non-overlapping categories of target molecules that are detected in the test.

By a category-specific binding site is meant a site on a target molecule that specifically binds to a category-binding molecule under specific-binding conditions and that distinguishes target molecules that are members of a particular category to be identified in a test from target molecules that are not members of that category but might also be present in the test sample. That is, the site is typically present on all members of one category, and typically not on any members of non-over lapping categories. Category-specific binding sites specifically bind to category-specific binding molecules.

Consider, for example, an epitope (an antigenic site) on a HIV viral envelope protein that specifically binds to an antibody category-binding molecule. The target molecule is the viral envelope protein and the category-specific binding site is the epitope on the envelope protein.

If a test scans a sample for a category of target molecules that is characteristic of a taxonomic group, a category-specific binding site is one that is typically present on the target molecules of all members of that taxonomic group, but is typically not present on all members of other taxonomic groups that might be present in the test sample. An example is a site on an HIV membrane protein that binds to a particular monoclonal antibody.

Alternatively, a test might scan a sample for category-specific binding sites that are shared by members of different taxonomic groups. Examples of this type of category-specific binding sites include various macromolecules (e.g., DNA) and genes, mRNAs, and proteins that confer antibiotic resistance, confer virulence, or indicate viability. A category-specific binding site is often a part of a larger molecule or complex. For example, a category-specific genomic sequence can be used as a category-specific binding site in a test. Such a category-specific binding site is part of a much larger genome that may contain (1) sections that are not category-specific; (2) sections that are category-specific binding sites but for which the test does not scan; and (3) other sections that are distinct category-specific sequences for which the test does scan.

Binding sites that are present in, e.g., 80%, 90%, 95%, or more than 99% of the target molecules that are members of a category but that are absent in, e.g., 80%, 90%, 95%, or more than 99% of the target molecules that are members of all other categories of the same class, are considered category-specific binding sites. Note that a category-specific binding site can be trivially or exceptionally absent from a target molecule that is a member of the category. Similarly, a category-specific binding site can be trivially or exceptionally present in a target molecule that is not a member of a category. For example, consider a protein site that occurs in essentially all E. coli bacteria but in no other bacterial species. If, as might be the case in less than one cell out of millions of bacteria, a mutation causes the protein to not be produced, the marker will not be present in that strain of E. coli. This protein site is still considered a category-specific binding site. Alternatively, the gene for the same protein is transferred to a strain of a different species of bacteria by recombinant DNA technology or by natural means (e.g., by viral transduction). In this case, a bacterial strain that is not a member of the E. coli group would express what would still be considered an E. coli-specific binding site.

By category-binding molecule is meant a molecule or molecular complex that specifically binds to a category-specific binding site. Examples of category-binding molecules are nucleic acid probes that hybridize to genomic DNA; nucleic acid aptamers that have been selected or "evolved" in vitro to bind specifically to sites on proteins; antibodies that bind to cellular antigens or serum proteins; and ligands such as epidermal growth factor or biotin that bind specifically to hormone receptors or to binding molecules, such as avidin. Two category-binding molecules are said to be distinct if they bind to distinct and non-overlapping category-specific binding sites. Category-binding molecules may be referred to according to their molecular composition, e.g., a category binding oligonucleotide, probe, antibody, ligand, etc.

By capture molecule is meant a category-binding molecule that is stably bound to a surface, membrane, or other matrix that is not a particle.

By a category-binding molecule that specifically binds to a category of target molecules is meant a category-binding molecule that binds under defined binding conditions to essentially all target molecules that are members of a category scanned for by a test, but to essentially no other molecules that are likely to be present in the sample. The number of category-binding molecules that are bound by target molecules in a category scanned for as compared to the number bound by target molecules not in such a category, are typically two-fold, five-fold, ten-fold, or greater than fifty-fold greater.

By binding conditions is meant the conditions used in a test to achieve specific binding of category-binding molecules to category-specific binding sites. For example, when the category-binding molecules are category-specific DNA probes, the binding conditions for a particular test might be stringent DNA hybridization conditions. The appropriate stringent DNA hybridization conditions depend on the nature of the probes, as is well known by those familiar with the art. For example, for typical DNA probes of length greater than 500 bases, an appropriate binding condition (usually referred to as a "washing condition" in the hybridization vernacular) is 65° C. at 0.2×SSC. For binding an antibody to an antigen, typical binding conditions are room temperature in PBS-TB.

By a family of category-binding molecules is meant a set of category-binding molecules that specifically bind to a particular category of target molecules. A polyclonal antibody preparation raised to Hepatitis C virus core protein constitutes a family of category-binding molecules since it comprises multiple distinct antibodies that bind specifically to the same category of target molecule—HCV core protein. Polyclonal antibodies generally constitute families of category-binding molecules since they usually include multiple distinct category-binding molecules that bind to the same category of target molecule. Note that, unless affinity purification is used, polyclonal antibody preparations typically also contain antibodies that do not bind to the chosen category of target molecule and may contain antibodies that bind to other categories because the antibody repertoire of an animal is determined by the animal's infection history. Therefore, polyclonal antibodies are preferably purified by affinity methods.

Category-binding molecules in a family might bind to some target molecules in the category but not to others. For example, consider HIV-1 envelope protein-specific antibodies that do not cross-react with HIV-2 envelope protein, and HIV-2-specific antibodies that do not cross-react with HIV-1 envelope protein. If HIV is to be a detected as a category in a test without differentiating between HIV-1 or HIV-2, a mixture of the two types of antibodies could be labeled with signaling moieties with the same signal signature. The same signal is obtained whether HIV-1 or HIV-2 is present when this family of category-binding molecules, which is a mixture of the two antibody preparations, is used in a test. (Note that if antibodies are used to capture the HIV target molecules at a site in the detection zone in this example, a mixture of anti-HIV-1 and anti-HIV-2 capture antibodies is used at the site).

Another example of a family of category-binding molecules is a set of 80 category-specific genomic DNA sequences that occur in all *E. coli* O157:H7 strains but that do not occur in members of other groups of bacteria. This family of category-binding molecules can hybridize as a group to suitably prepared *E. coli* O157:H7 cells but does not hybridize to other categories of cells.

By non-overlapping families of category-binding molecules or is meant families of category-binding molecules in which each family binds specifically to one, and only one, category of target molecules in a set of non-overlapping categories of target molecules. That is, a set of non-overlapping families of category-binding molecules map to a congruent set of non-overlapping categories of target molecules. For example, in a test that scans for the target molecules that characterize the 4 USP objectionable organisms *E. coli, Salmonella, Pseudomonas* spp., and *Staphylococcus aureus*, there are four non-overlapping categories of target molecules. Such a test might incorporate four different non-cross-reacting polyclonal antibodies, each specific for one of the target molecule categories. Thus, the test comprises four non-overlapping families of category-binding molecules. The non-overlapping families of category-binding molecules in a test are called an ensemble of category-binding molecules (see definition below).

By an ensemble of category-binding molecules is meant a set of one or more non-overlapping families of category-binding molecules that are combined in a mixture for a particular test. Tests that scan for multiple non-overlapping categories of target molecules comprise one family of category-binding molecules per category. The entire set of category-binding molecules, that comprise these families, is referred to as an ensemble. For example, consider a test that scans for the presence of five types of upper respiratory viruses (RSV, influenza A, influenza B, parainfluenza, and adenovirus) using five virus-specific monoclonal antibodies. The five monoclonal antibodies constitute five non-overlapping families of category-binding molecules. The combined set of antibodies is an ensemble of category-binding molecules.

By the category-binding molecule complexity of an ensemble is meant the number of distinct category-binding molecules in an ensemble. For example, if an ensemble of category-binding molecules consisted of 234 oligonucleotide probes, the category-binding molecule complexity of the ensemble would be 234.

By the family complexity of an ensemble is meant the number of non-overlapping families of category-binding molecules in an ensemble. The family complexity is the same as the minimum number of target molecules required to bind a category-binding molecule from each of the families in an ensemble. The family complexity of a test corresponds to the categorical complexity of a test—i.e., the number of distinct categories for which the sample is scanned. In general, the family complexity also corresponds to the number of distinct signal signatures used in a test. Consider an ensemble of target molecule-specific antibodies designed to detect four human cytokine proteins: granulocyte macrophage colony-stimulating factor (GM-CSF); interleukin-2 (IL-2); interleukin-4 (IL-4); and tumor necrosis factor-$\alpha$ (TNF-$\alpha$). The family complexity of the ensemble is four, since no subset of target molecules smaller than four could suffice to bind each of the antibodies in the ensemble. As another example, consider an ensemble of DNA probes consisting of three families of probes. One family consists of a set of 12 *E. coli*-specific category-binding DNA sequences, another family consists of a set of 10 rotavirus category binding DNA sequences, and another family consists of a set of 15 Giardia category binding DNA sequences. The family complexity of this probe ensemble is three since three categories of target molecules (*E. coli*, rotovirus, and Giardia specific target molecules) are required to bind to all of the probes in the ensemble.

By signal element is meant a molecule or particle that directly generates a detectable signal. The phrase "directly generates" refers to the fact that signal elements are the immediate source or critical modulator of the detectable signal. Thus, if the signal is photons that arise from a fluorophore, the fluorophore is the immediate source of the photons and, therefore, is a signal element. If the signal is photons scattered by an RLS particle, the RLS particle is a signal element. Alternatively, if the signal is the light transmitted or scattered from a chromogenic precipitated product of the enzyme horseradish peroxidase, the chromogenic product is the signal element.

A characteristic of a signal element is that such an element cannot be divided into parts such that each part generates a signal that is comparable (in character, not necessarily in intensity) to the whole. Thus, a 2 nM diameter quantum dot is a signal element, as dividing it changes the character (emission spectrum) of the resulting nanocrystals. A 5 µm particle impregnated with a fluorescent dye such as fluorescein, is not a signaling element, since it could be divided into parts such that each part has signaling characteristics comparable to the intact particle. The molecule fluorescein, in contrast, is a signaling element. The detectable products of signal generating enzymes (e.g., luciferase, alkaline phosphatase, horseradish peroxidase) are also considered signal elements. Such signal elements (or their precursors when there is a chemical conversion of a precursor to a signal element) may be diffusible substances, insoluble products, and/or unstable intermediates. For example, the enzyme alkaline phosphatase converts the chemiluminescent substrate CDP-Star (NEN; catalog number NEL-601) to an activated product, which is a photon-emitting signal element.

By signaling moiety is meant a molecule, particle, or substance comprising or producing (in the case of enzymes) one or more signal elements and that is or can be conjugated to a category-binding molecule. The signaling moiety can be attached to the category-binding molecule either covalently or non-covalently and either directly or indirectly (e.g., via one or more adaptor or "chemical linker" moieties or by both moieties being conjugated to the same particle). Examples of signaling moieties include carboxylated quantum dots; a fluorophore such as Texas Red that is modified for binding to a nucleic acid probe or an antibody probe; streptavidin-coated fluorescent polystyrene particles (which can be conjugated to biotinylated category-specific binding proteins); a rolling-circle replication product containing repeated nucleic acid sequences each of which can hybridized to several oligonucleotides tailed with fluorescently modified nucleotides and which contains a category-specific binding oligonucleotide at the 5' end. A signaling moiety can comprise physically distinct elements. For example, in some cases the signaling moiety is an enzyme (e.g., alkaline phosphatase) that is conjugated to a category-binding molecule (an antibody, for example). Signal is generated when a substrate of alkaline phosphatase (e.g., CDP-Star, or BM purple from NEN and Roche, respectively) is converted to products that are signal elements (e.g., an unstable intermediate that emits a photon, or a precipitable chromogenic product). It is not unusual for the category-binding molecules, enzymatic signaling moieties, and substrate to be applied to the reaction at distinct times.

By signaling moiety complex is meant a physical entity that comprises more than one signaling moiety and more than one category-binding molecule. The physical association of the signaling moieties and category-binding molecules in a signaling moiety complex must be stable (e.g., the signaling moieties and category-binding molecules should have mean half-lives of association with the complex of at least one day in PBS at 4° C.). As an example of a signaling moiety complex, consider a polystyrene microparticle that is coated with thousands of molecules of two types: a target molecule-specific antibody and alkaline phosphatase. Such a signaling moiety complex binds to the target molecule via the conjugated antibody category-binding molecule. When incubated with a chromogenic alkaline phosphatase substrate (the signal element; e.g., BM purple, Roche), a colored spot can be generated which can be detected by eye. Alternatively, the same signaling moiety complex, when incubated with either a chemiluminescent or a fluorescent alkaline phosphatase substrate, generates either a chemiluminescent or fluorescent signal. Further examples of signaling moiety complexes include: nanogold particles conjugated to fluorescein-labeled antibodies and latex particles conjugated to both oligonucleotide category-binding molecules and acridinium esters that chemiluminescence upon addition of hydrogen peroxide.

By particle is meant a matrix which is less than 50 microns in size. The size of a population or batch of particles is defined as the mean measurement of the longest pair of orthogonal dimensions for a sample of the particles. The longest pair of orthogonal dimensions is the pair of orthogonal dimensions of a particle, the sum of the lengths of which is the maximum for all such sums for the particle. If a sample of two particles has a longest pair of orthogonal dimensions of 1 micron×2 micron and 2 micron×3 micron, respectively, the mean measurement of the longest pair of orthogonal dimensions is 2 microns [(1+2+2+3)/4=2 microns]. The mean measurement of the longest pair of orthogonal dimensions for a sample of particles is, e.g., less than 50 microns, less than 20 microns, or less than 5 microns.

Many particles have some characteristics of a solid. However, molecular scaffolds or complexes, which may not be rigid, are also defined as particles. For example, dendrimers or other branching molecular structures are considered to be particles. Similarly, liposomes are another type of particle. Particles can be dyed with or conjugated to signal elements. Particles are often referred to with terms that reflect their dimensions or geometries. For example, the terms nanosphere, nanoparticle, or nanobead are used to refer to particles that measures less than 1 micron along any given axis. Similarly, the terms microsphere, microparticle, or microbead are used to refer to particles that measure less than one millimeter along any given axis. Examples of particles include latex particles, polyacrylamide particles, magnetite microparticles, ferrofluids (magnetic nanoparticles), quantum dots, etc.

By labeling particle is meant a particle that can specifically bind to target molecules and generate a signal. Labeling particles are conjugated to both signaling moieties and to category-binding molecules.

By target molecule:labeling particle complex is meant a labeling particle to which one or more target molecules are specifically bound.

By labeling ratio is meant the ratio of target molecules to labeling particles during a contacting step. For example, if $1 \times 10^7$ labeling particles are contacted with a sample containing $1 \times 10^6$ target molecules, the labeling ratio is 0.10. For the purposes of calculating labeling ratios, only the target molecules that can specifically bind to labeling particles are considered. For example, target molecules that are physically inaccessible (e.g., sequestered in a cellular compartment) are not included in the calculation.

By signal character of a signal element or signal moiety is meant the aspect or aspects of a signal generated by the signal element signaling moiety that is useful for distinguishing it from other signal elements or signaling moieties. For example, the signal character of a signaling moiety labeled with fluorescein and rhodamine is fluorescence. The character of a radio transponder is radio frequency. Examples of photonic signaling character are fluorescence, light scattering, phosphorescence, reflectance, absorbance, chemiluminescence, and bioluminescence. All but the latter two examples of photonic signaling character depend on external illumination (e.g., a white light source, a laser light source, or daylight). In contrast, chemiluminescence and bioluminescence are signaling characters that are independent of external light sources.

By the class of a signal element or signaling moiety is meant the distinct quality of the signal that is useful for distinguishing it from other signal elements or signaling moieties. For example, a liposome that is labeled with red dye is distinguished from differently colored liposomes. The color red is its class. For a micro-transmitter that broadcasts a particular radio-frequency signal, the quality of the radio-frequency signal that differentiates the micro-transmitter from other micro-transmitters constitutes the signal element class.

By signal signature is meant the distinctive signaling quality of the combination of signaling moieties that bind to a category of target molecules in a test. A target molecule that is bound to four types of antibodies, one of which is conjugated to a fluorescein molecule, and three of which are conjugated with rhodamine molecules has a signal signature that is described by the combined weighted absorbance and emission spectra of fluorescein and rhodamine.

By signal complexity of a test or an ensemble of labeled category-binding molecules is meant the number of categories of target molecules that can be distinctly labeled in the test or by binding to the ensemble. Alternatively, the signal complexity is defined as the number of distinct signal signatures that would be expected to occur if a member of each category of target molecule were present. For some tests, the signal complexity of an ensemble of category-binding molecules is the same as the number of categories for which the test scans. Other tests, which scan for many categories, may only have a signal complexity of one.

By selection force is meant a force that is used to capture, isolate, move, or sequester target molecules. Examples of selection forces include gravity, magnetism, electrical potential, centrifugal force, centripetal force, buoyant density, and pressure. Target molecules can be mobilized by a selection force acting on the target molecule alone. Alternatively, selection forces can act specifically on target molecules that are associated with selection moieties (see definition below).

Examples of the application of selection forces to mobilize target molecules include centrifugation of target molecules; magnetic selection of target molecules bound to magnetic particles; gravitational sedimentation of target molecules labeled with metallic particles; and deposition of target molecules on a porous membrane by vacuum filtration. Further instances of the use of selection forces are included in the examples below.

By selection moiety is meant an atom, molecule, particle, or other entity that can be conjugated to a category-binding molecule and that confers on the category-binding molecule the ability to be selectively captured, isolated, moved, or sequestered by a selection force. When a category-binding molecule:selective moiety complex is specifically bound to a target molecule, the target molecule can also generally be selectively captured, isolated, moved, or sequestered by the selection force. Selective refers to the preferential conferring of susceptibility to mobilization by the selection force on selection moieties and associated entities over entities not associated with selection moieties.

Paramagnetic particles and ferritin are examples of selection moieties. A dense silica particle that sinks in solution is another type of selection moiety. Such particles, when coated with category-binding molecules and bound to a microbial target molecule will cause the target molecule to sink in aqueous solution, thus enabling separation of the bound target molecule from other sample unbound constituents.

By selective character is meant the aspect or aspects of a selection moiety that is useful for capturing, selecting, or moving the selection moiety. For example, the selective character of a paramagnetic particle is magnetism. The selective character of a silica particle that rapidly sinks in aqueous solution is mass.

By a roughly planar surface or substrate is meant a surface that can be aligned in parallel to an imaginary plane such that when the distance is measured from points in any 1 mm×1 mm square on the surface to the closest points on the imaginary plane, the absolute value of the mean distance is less than 50 micrometers.

By detection surface is meant the surface of a roughly planar substrate onto which target molecules are deposited in some embodiments of the invention. In embodiments using photonic signaling character, if the detection surface is optically transparent, detection can be effected via either face of the detection surface. If the detection surface is opaque, detection is effected via the face of the detection surface on which the target molecules are deposited.

By detection area is meant the area of the detection surface or detection zone that is simultaneously analyzed by the invention. The detection area is typically greater than 1 mm, e.g., greater than 5 mm, 10 mm, or 15 mm, in its longest linear dimension. For example, the section of a glass slide that is simultaneously imaged by an optical device that includes a collection lens and a CCD chip might measure 0.8 cm×0.5 cm. The detection area is then 0.4 cm$^2$.

By detection zone is meant the volume in which target molecules can be detected. The detection zone has the same dimensions as the detection area but has a depth corresponding to the depth in which a labeling particle can be detected and identified. The depth of the detection zone is therefore dependent on the threshold criteria used to score for positive signal. When optical detection is used, the depth of the detection zone is dependent on the optical depth of field.

By the longest dimension of the detection area is meant the line of maximum length that can be drawn between two points on the perimeter of the detection area. For example, if the detection area is a rectangle measuring 0.3 cm×0.4 cm, the longest dimension of the detection area is the diagonal, 0.5 cm. If the detection area is an ellipse with semi-major axis of length 7 mm and semi-minor axis of length 2.5 mm, the longest dimension of the detection area is 14 mm.

By large area detection or large area imaging is meant a method for detecting microscopic target molecules in which the detection area (the area that is simultaneously analyzed by the detection device) is much larger than the target molecule. The detection area for large area detection has at least one linear dimension that is ≥1 mm. In contrast, the microscopic target molecules are substantially smaller, typically measuring less than 50 µm in at least two orthogonal dimensions. Examples of large area detection include imaging a 9 mm diameter detection area with a CCD camera; imaging a 2 cm×1 cm rectangle by scanning with a CCD line scanner that has a long dimension of 1 cm; imaging a 4 cm×4 cm filter containing microbial target molecules using direct exposure on photographic film; and visual detection of colored spots corresponding to microscopic target molecules on a 1 cm×3 cm test area in a rapid lateral flow strip test.

Several technologies scan samples for microscopic target molecules but do not exploit large area detection. Examples include: flow cytometry; solid phase laser microbeam scanning cytometry; liquid phase scanning (as in Tibbe, et al., Nat Biotechnol 17: 1210-3, 1999); and examining/imaging multiple high power microscopic fields on a slide.

By conjugated or stably associated is meant a physical association between two entities in which the mean half-life of association is least one day in PBS at 4° C. Consider, for example, the complex case of passive protein adsorption to polystyrene particles. There are several different classes of adsorbed proteins. Some proteins are stably associated to the surface with half-lives of many months. Other proteins, such as those that are loosely bound on the outer layer of adsorbed protein, may not be stably associated with the particles and can leach out within hours.

By image intensifier or image tube is meant a device that amplifies a photonic signal, as defined in the glossary of Inoué, Shinya, et al., *Video microscopy: the fundamentals* (Plenum Press, New York, 1997; p. 665): "A device coupled (by fiber optics or lenses) to a video camera tube to increase sensitivity. The intensifier is a vacuum tube with a photocathode on the front end that emits electrons according to the image focused upon it, an electron lens and/or microchannel plate(s) that focuses the electrons onto a phosphor at the back end, and a high voltage accelerator that increases the energy of the electrons. Can be single or multiple stage." A variety of such image intensifiers is described in detail in Chapter 8 of the same reference.

By simultaneously detecting target molecules in a section of the detection area is meant detection of the signal from a section of a roughly planar detection surface in one step. Large area imaging of target molecules in a detection area using a CCD chip, visual detection, or photodiode-based signal integration are examples of simultaneous detection.

By target molecules in the stationary phase is meant target molecules that are non-mobile. For example, target molecules fixed on glass slides are in the stationary phase. Target molecules that are captured by category-binding molecules in fixed positions on the bottom of the well of a microtiter dish are in the stationary phase. Even if such target molecules are not affixed to a surface, and might be moved by hydrodynamic or other forces, target molecules are considered to be in the stationary phase if, during detection/imaging, successive images taken with intervals of more than 10 seconds detect essentially the same target molecules in essentially the same relative positions. Target molecules in flow cytometry applications are not in the stationary phase. However, target molecules captured by antibodies bound to the solid-phase test zone of a lateral flow test are in the stationary phase.

By homogenous assay or homogenous immunoassay is meant an assay or immunoassay in which the reactants are not physically removed from the products of the completed assay.

By identification is meant determining the category of which a target molecule is a member. For example, consider a lateral flow test that scans for several categories of target molecules, each of which is potentially present in a sample. A target molecule belonging to a particular category is captured at the region of the membrane to which the corresponding category-specific antibodies are bound. Since it is known which membrane zones contain which capture antibodies, target molecules are identified by the zone in which capture occurs.

By sample is meant material that is scanned by the invention for the presence of target molecules.

By a ligation-dependent polymorphism probe pair is meant a set of oligonucleotide category-binding molecules (wherein the set contains more than one oligonucleotide) that, when hybridized to a genome, abut at a polymorphic site. One oligonucleotide in the pair comprises sequences that are complementary to the genomic sequences on one side of the genomic polymorphic site, while the other oligonucleotide comprises sequences that are complementary to the other side of the polymorphic site. A set of such oligonucleotides, when hybridized adjacently to a genome, can be efficiently ligated to each other only when the allele, or genotype, at the targeted site matches the abutting sequences of the oligonucleotides of the polymorphism probe. The structure and use of ligation-dependent polymorphism probe pairs is illustrated in FIG. 18 and FIG. 19. Generally, a group of polymorphism probes is synthesized that correspond to each allele at a particular site. Polymorphism probes can comprise various functional moieties including, signaling moieties, selection moieties, chemical spacers or tethers, tags, amplification sites, and haptens. For examples of the use of SNP probes, see Example 14 and Example 15.

By an extension-dependent polymorphism probe is meant a nucleic acid category-binding molecule that is designed to hybridize to a sequence such that the 3' end of probe is within several nucleotides of but base-paired with the polymorphic site to be detected by a test. Template-dependent extension of the extension-dependent polymorphism probe is used to differentially label the probe depending on the allele at the polymorphic site. For example, consider an oligonucleotide designed to hybridize immediately adjacent to a polymorphic site that has either an "A" or a "C" on the template strand, such that the 3' end of the oligonucleotide is immediately adjacent to the polymorphic site. Incubating the hybrid with TTP that is labeled with a green emitting fluorophore and dGTP that is labeled with a red fluorophore in the presence of DNA polymerase under appropriate conditions can lead to differential labeling of the probe depending on the allele of the template strand.

By allele-specific hybridization probe is meant an oligonucleotide category-binding molecule that under specified conditions hybridizes differentially to different nucleic acid alleles. For example, those familiar with the art can determine conditions under which a 12 base oligonucleotide can efficiently hybridize to a DNA fragment that contains an exact match, but under which the same oligonucleotide can not efficiently hybridize to a DNA fragment with a match at 11 of the 12 bases in the oligonucleotide.

By direct visual detection is meant visual detection without the aid of instrumentation other than wearable corrective lenses. For example, direct visual detection can be used to detect the reddish reflective signal of nanogold particles in some rapid lateral flow tests.

By photoelectric detector is meant a man-made device or instrument that transduces photonic signals into electric signals. Examples of photoelectric detectors include CCD detectors, photomultiplier tube detectors, and photodiode detectors, e.g., avalanche photodiodes.

By illuminating is meant irradiating with electromagnetic radiation. Electromagnetic radiation of various wavelengths can be used to illuminate. It includes, for example, radiation with wavelengths in the X-ray, UV, visible, or infrared regions of the spectrum. Note that illuminating radiation is not necessarily in the visible range.

By signal elements or signaling moieties with photonic signaling character is meant signal elements or signaling moieties that are detectable through the emission, reflection, scattering, refraction, absorption, capture, or redirection of photons, or any other modulation or combination of photon behavior. Some examples of signal elements or signaling moieties that have photonic signaling character include: the fluorophore Texas Red (fluorescent signaling character); CDP-Star (chemiluminescent signaling character); luciferase (bioluminescent signaling character); resonance light scattering particles (light scattering signaling character); BM purple (light absorption or chromogenic signaling character); and up-converting phosphors (absorption of two long wavelength photons and emission of one shorter wavelength photon).

By 'number'×'solution name' is meant an aqueous solution comprising the constituents of the solution at number times the concentration of the solution (except for water). For example, 10×EE contains 10 mM EDTA/100 mM EPPS (EE, or 1×EE, contains 1 mM EDTA/10 mM EPPS).

EE is a solution that is 1 mM EDTA/10 mM EPPS. Before mixing them together, the conjugate acids of both components are brought to pH 8.0 with NaOH.

HYB is a solution used for hybridization containing: 1M NaCl, 50 mM EPPS pH 8.0, 2% blocking reagent (Boehringer Mannheim); 0.5% v/v Tween, 20 µg/ml yeast tRNA (Sigma).

UBB (universal binding buffer) is a solution useful for binding mixtures of various types of category-binding molecules (such as antibodies and nucleic acids) containing: 250 mM NaCl, 50 mM EPPS pH 8.0, 2% blocking reagent (Boehringer Mannheim); 0.5% v/v Tween, 20 µg/ml yeast tRNA (Sigma).

BB (blocking buffer) contains 100 mM EPPS pH 8.0/150 mM NaCl/2% blocking reagent (Boehringer Mannheim).

PB is 0.1 M sodium phosphate buffer pH 7.4.

PBS is a phosphate-buffered saline solution containing: 120 mM NaCl, 2.7 mM KCl and 10 mM phosphate buffer (sodium salt) pH 7.4.

PBS-B is 0.1% BSA (IgG Free; Sigma Cat. No. A-7638) in PBS.

PBS-T is 0.05% Triton X-100 (Sigma Cat. No. X-100) in PBS.

PBS-TB is PBS/0.1% BSA/0.05% Triton X-100.

PBT is PBS/0.1% BSA (IgG Free; Sigma Cat. No. A-7638)/0.05% Tween-20 (Sigma Cat. No X-100).

LB is Luria Broth for growing bacteria and is made as described previously (Ausubel 1987, supra).

SSC is 150 mM NaCl/15 mM $Na_3$ citrate adjusted to pH 7.0 with HCl.

MES is (2-[N-Morpholino]ethanesulfonic acid).

MESB is 0.05M MES (2-[N-Morpholino]ethanesulfonic acid), pH 6.1.

EDAC is (1-Ethyl-3-(3-dimethylaminopropyl) carbodiimide.

Ligation buffer is 10 mM $MgCl_2$/50 mM Tris-HCl/10 mM dithiothreitol/1 mM ATP/25 µg/µl bovine serum albumin.

AP is alkaline phosphatase.

BAL is bronchoalveolar lavage.

BSA is bovine Serum Albumin.

CCD is charged coupled device.

CFTR is cystic fibrosis transmembrane conductance regulator.

Cfu is colony forming unit (a measure of bacterial concentration that corresponds to the number of viable bacterial cells).

CMV is cytomegalovirus.

FITC is fluorescein isothiocyanate.

HBV is Hepatitis B virus.

HCV is Hepatitis C virus.

HIV is Human Immunodeficiency virus.

Pfu is plaque forming unit (a measure of virus concentration that corresponds to the number of infectious virus particles).

PNA is peptide nucleic acid.

RSV is respiratory syncytial virus.

$TCID_{50}$ is tissue culture infectious dose at which 50% of flasks demonstrate infection.

XhoL is an oligonucleotide primer having the sequence: 5'-GGGCCCCCCCTCGATC-3' (SEQ ID NO: 1).

XhoR is an oligonucleotide primer having the sequence: 5'-ATCGATACCGTCGACCTC-3' (SEQ ID NO: 2).

Oligonucleotide sequences are presented in the 5' to 3' orientation when written as text, unless otherwise noted.

Unless otherwise noted, microbiological strains described in the specifications are obtained from the American Type Culture Collection (ATCC), Manassas, Va.

Using the invention, fluorescent labeling particles coated with anti-IL-2 antibodies (category-binding molecules) are bound to IL-2 protein molecules (target molecules) in blood. The resulting complexes are bound to capture antibodies on the bottom of the well of a microtiter dish. Unbound labeling particles are removed. Upon illumination, the captured labeling particles fluoresce, emitting photons that impinge on the pixels of a CCD chip. The number and position of the labeling particles is interpreted by automated image analysis. The figure is simplified by not including the optical components and other hardware.

Figure 2:
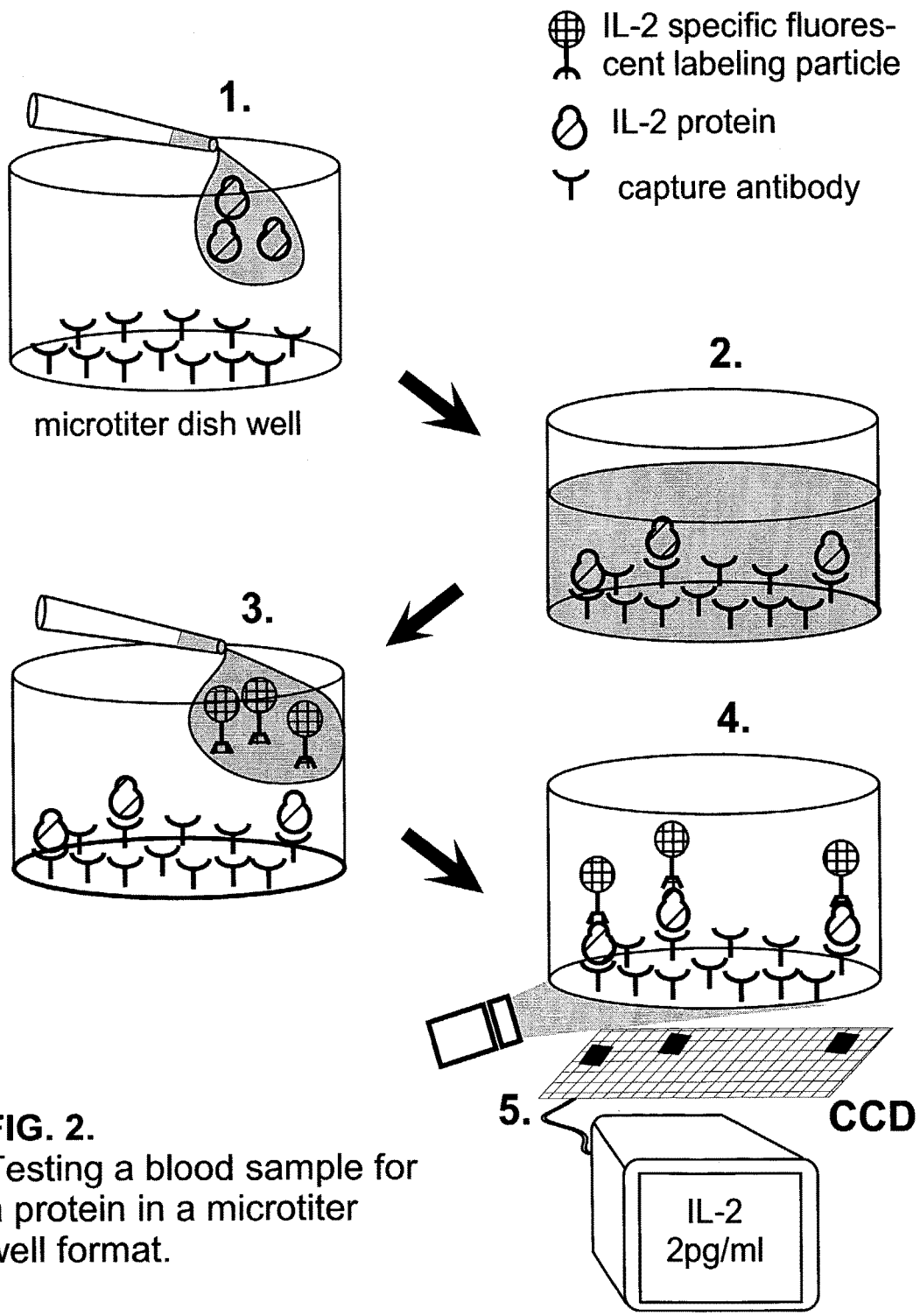

FIG. 2. Testing a blood sample for a protein in a microtiter well format.

The figure shows how imaging individual labeling particles is used to detect a target molecule, in this case a protein.

Figure 3:
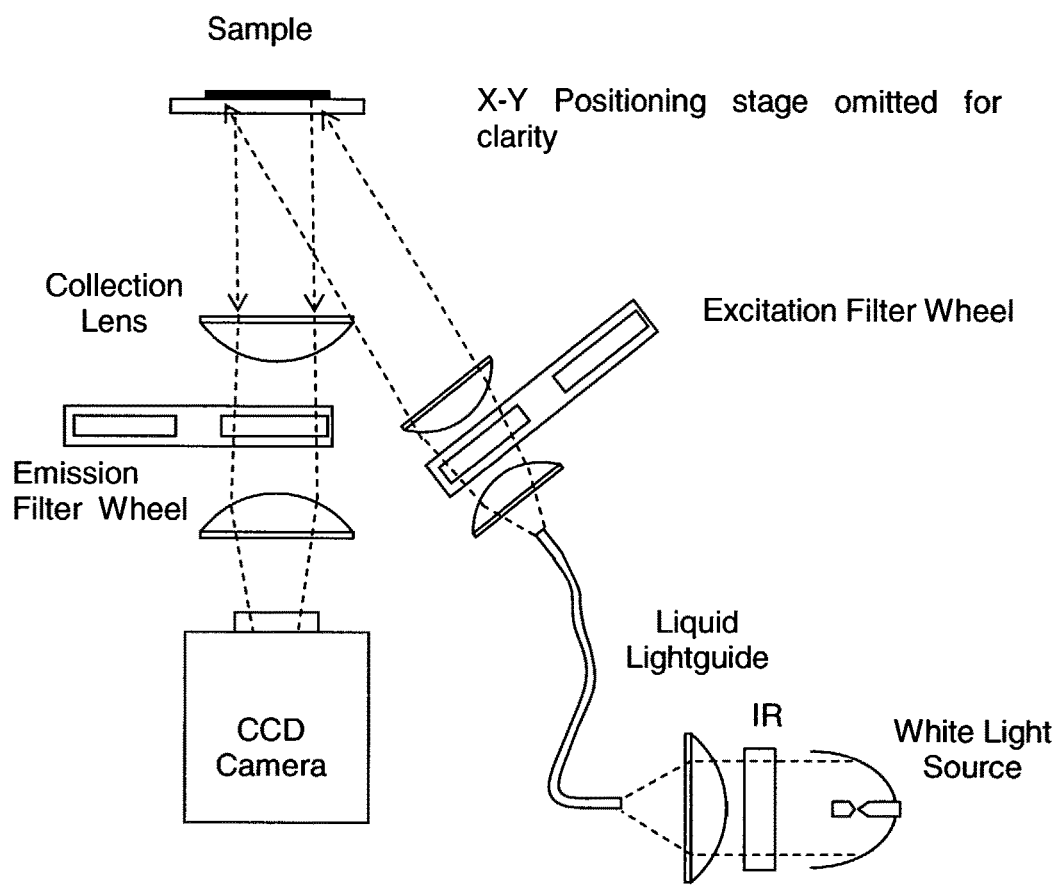

FIG. 3. A CCD imaging device for large area imaging.

The CCD-based imager depicted in the figure was used to collect much of the data described in the examples (see also Step 6 of Detailed Description section). Excitation light is provided by introducing light from a high intensity white light source (1000 Watt Xenon arc lamp, Model A-6000, Photon Technology Incorporated, Monmouth Junction, N.J.) into a liquid light-guide (5 mm core diameter, Model 380, Photon Technology Incorporated, Monmouth Junction, N.J.). The liquid light-guide carries the light to an excitation filter-wheel (BioPoint FW, Ludl Electronics, Hawthorne, N.Y.) and directs the filtered beam (typically 9 mm in diameter) onto the detection surface containing the labeled target molecules. The apparatus can detect labeled target molecules on various detection surfaces (e.g., porous membranes, microscope slides, microtiter dishes, coverslips, and tubes with flat, optically clear, bottoms). The incident light strikes the detection surface inducing fluorescence in the signaling moieties that are bound to target molecules via category-binding molecules and that are deposited on the optically clear surface. A portion of the emitted fluorescent light is collected by a high-collection efficiency lens system and transmitted through an emission filter-wheel (BioPoint FW, Ludl Electronics) to a CCD camera (Orca II, Hamamatsu, Bridgewater, N.J.).

Figure 4:
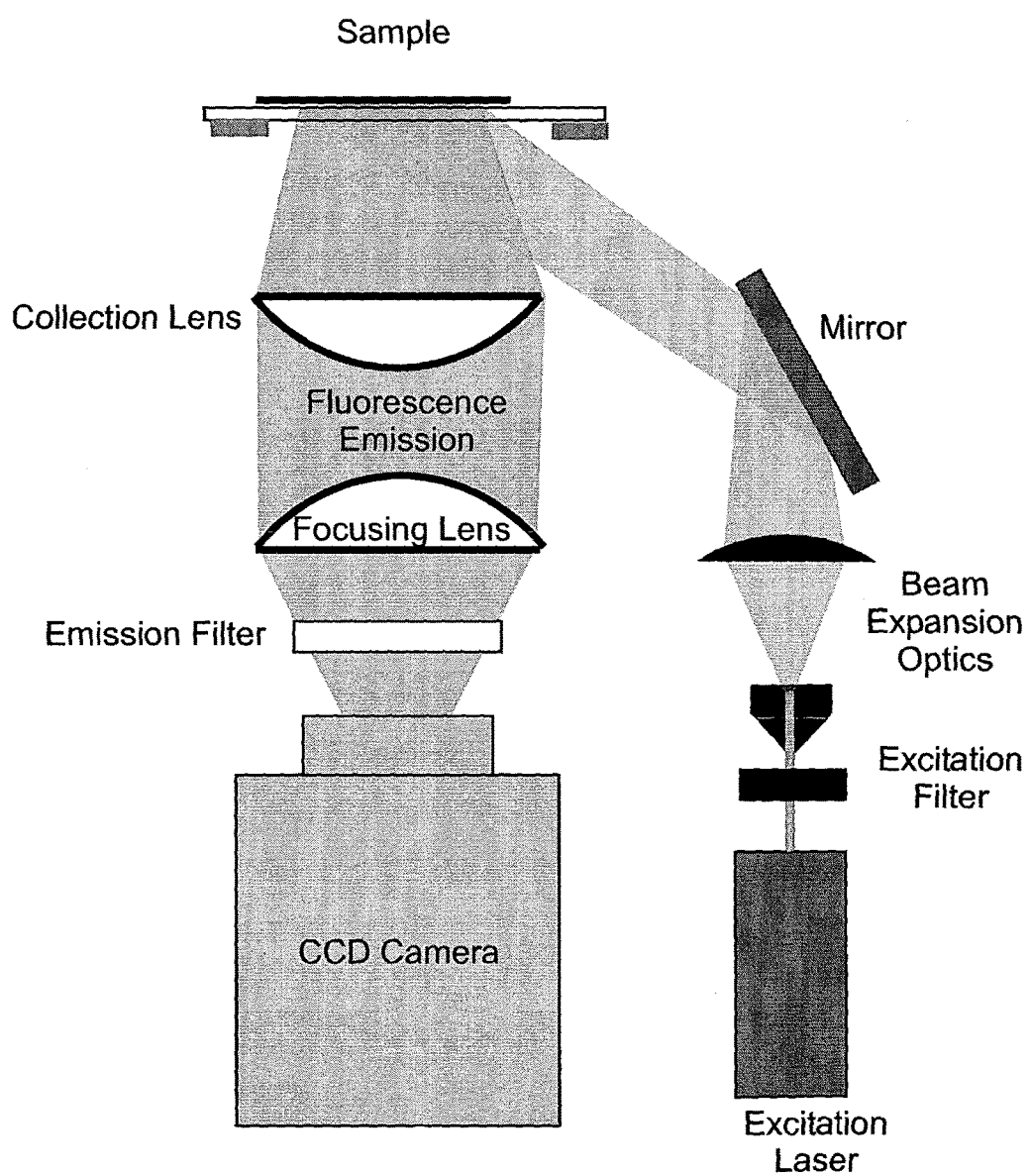

FIG. 4. A CCD imaging system for non-magnified large area imaging

The figure shows a CCD imager with an angular illumination configuration in which light is introduced onto the detection surface (shown here as the bottom of a well of a microtiter plate) at an angle from the side of the collection optics. The angle is chosen to optimize collection efficiency and to avoid obstruction of the incident beam by the collection lens. The advantage of this configuration is that reflections from the bottom surface of the sample holder are not collected by the collection lens and therefore do not contribute to the fluorescence background noise.

Figure 5:
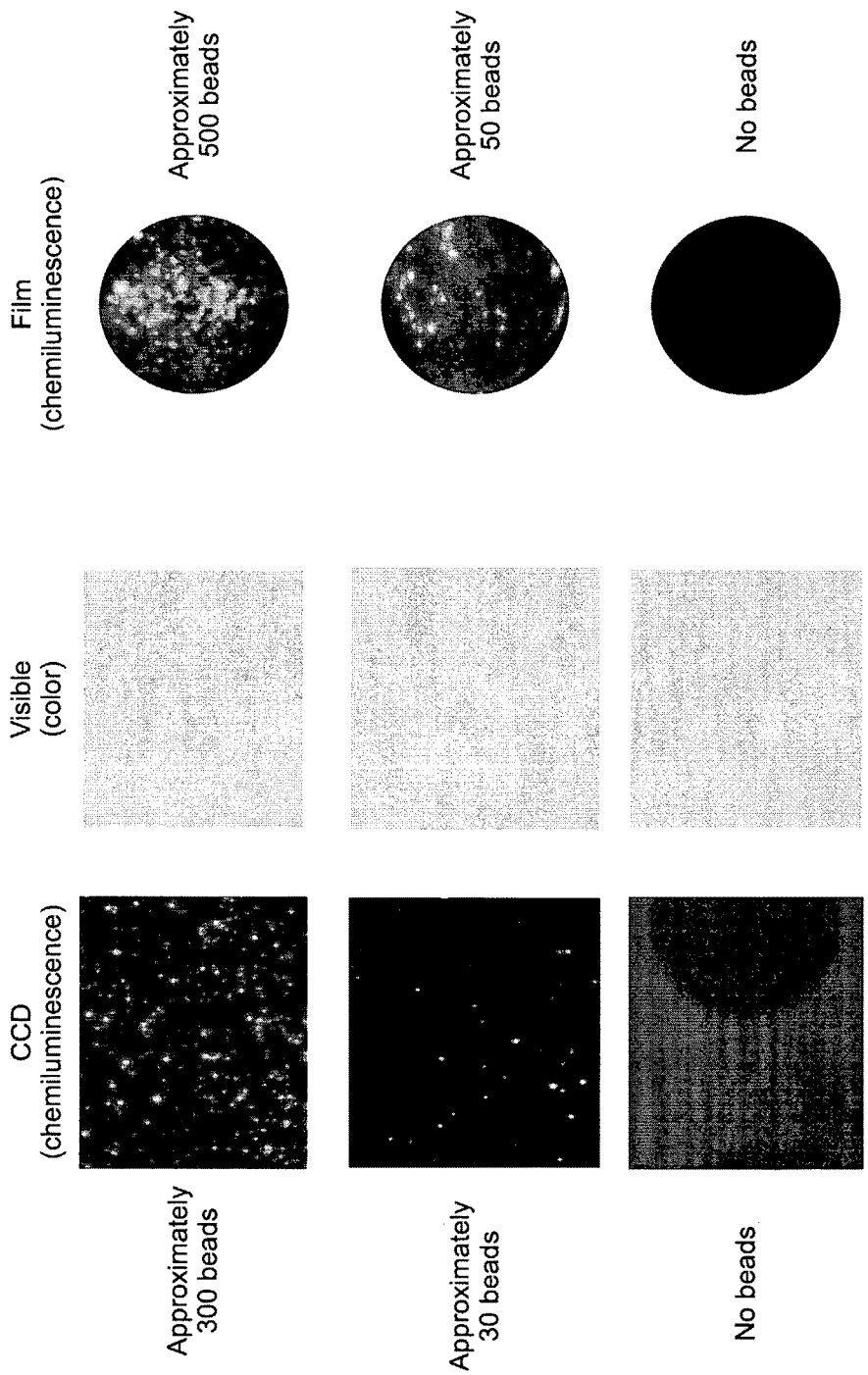

FIG. 5. Detecting individual microscopic labeling particles without magnification using electronic, instant film, and unaided visual detection (Example 1)

This figure demonstrates the invention's ability to detect individual microscopic labeling particles in a large detection area without magnification using a variety of detection methods. Individual labeling particles coated with alkaline phosphatase were detected using instant film, a CCD camera, and unaided visual detection. The same colored spots that were visible by eye are shown in the central panels in an image that was acquired using a digital camera.

Figure 6:
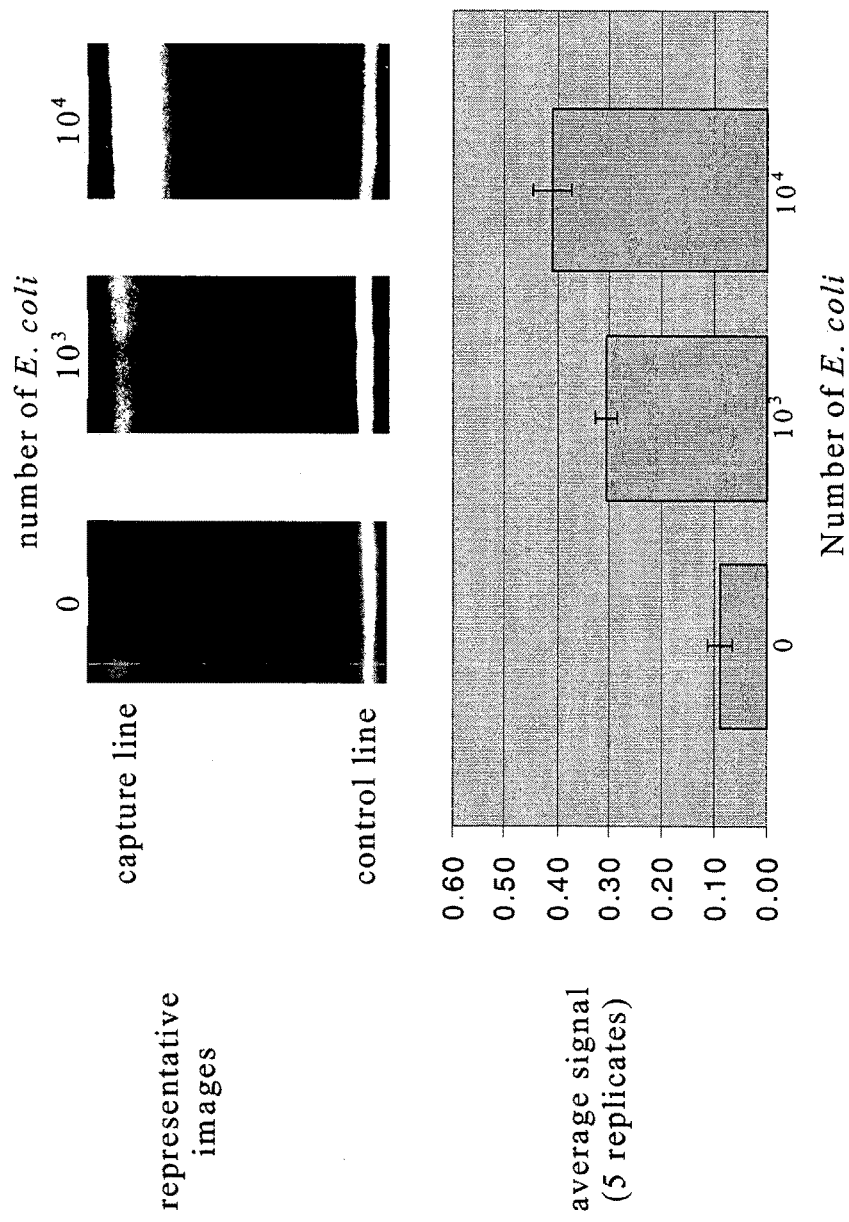

FIG. 6. An ultra-sensitive lateral flow test for detecting low numbers of bacteria using non-magnified large area imaging (Example 2)

The figure shows the results of an ultra-sensitive lateral flow test using non-magnified large area imaging. Images of the capture and control lines are shown from various test strips with different numbers of E. coli added to the assay. The bar graph illustrates that as the number of E. coli increase, the signal from the capture line also increased. This figure demonstrates the ability to detect low numbers of bacteria in a sample.

Figure 7:
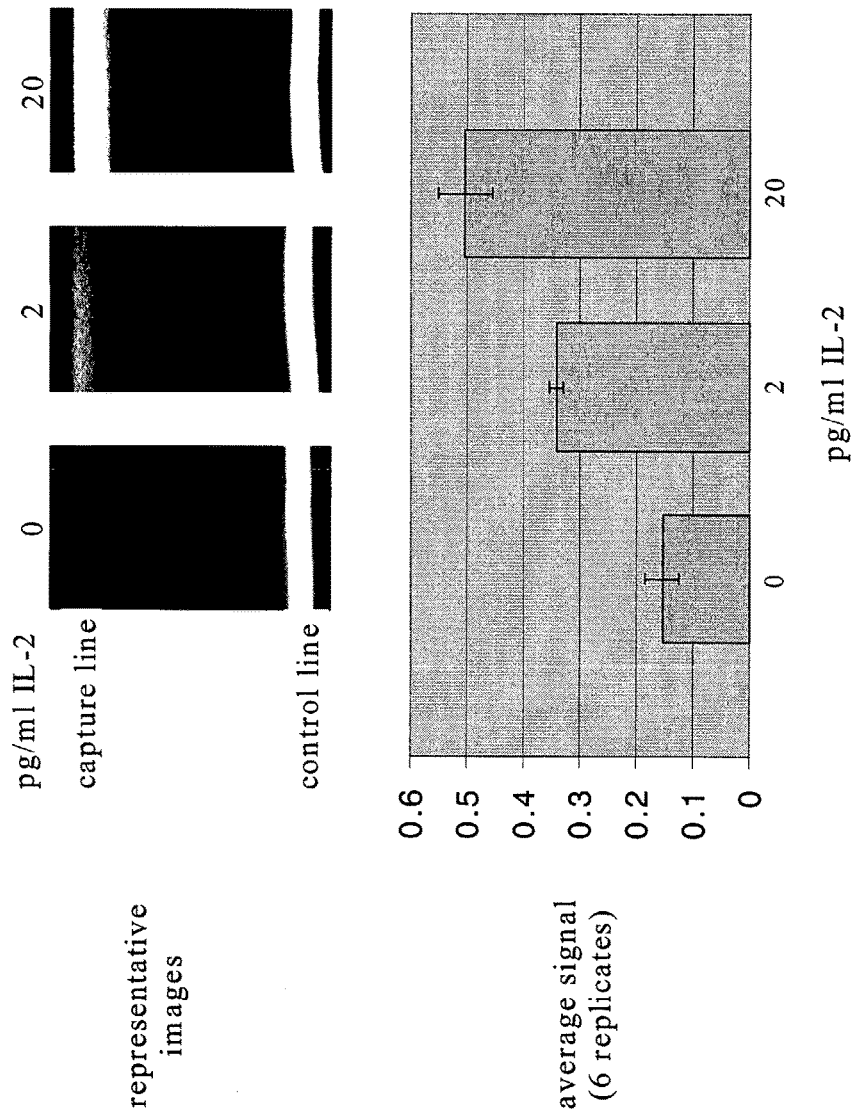

FIG. 7. An ultra-sensitive lateral flow test for detecting low levels of protein using non-magnified large area imaging (Example 3)

The figure shows the results of an ultra-sensitive test for the cytokine protein IL-2 using lateral flow format and non-magnified large area imaging. In the figure, capture and control lines images are seen from various test strips with different concentrations of IL-2 added to the assay. The bar graph illustrates that as the number of IL-2 increase, the signal from the capture line also increased. This figure demonstrates the ability to detect low levels of protein in a sample.

Figure 8:
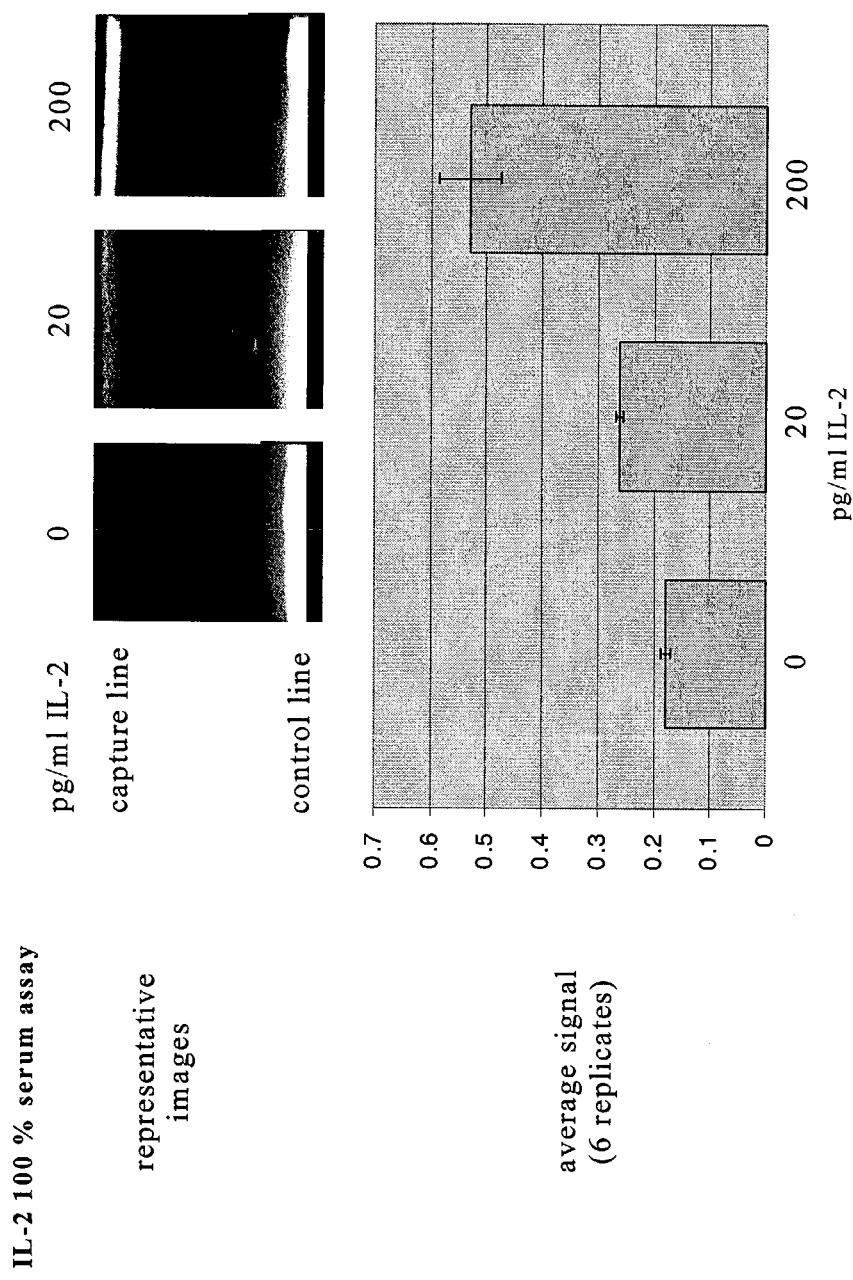

FIG. 8. Ultra-sensitive lateral flow test for detecting low levels of protein in serum using non-magnified large area imaging (Example 4)

The figure shows the results of the lateral flow test for IL-2 in serum. In the figure, capture and control lines images are seen from representative test strips. The leftmost strip shows the negative control. When the negative control is compared to the middle (20 pg/ml) and right (200 pg/ml) strips, it is apparent that as the amount of IL-2 increases, the signal from the capture line also increased. The bottom bar graph shows the signal from the average of five replicates in relation to the amount of IL-2 added. The error bars represent a three standard deviation error between the replicate signals. The data shows that the invention can detect IL-2 at 20 pg/ml of serum demonstrating that the assay detects very low levels of a target protein even in a complex sample.

Figure 9:
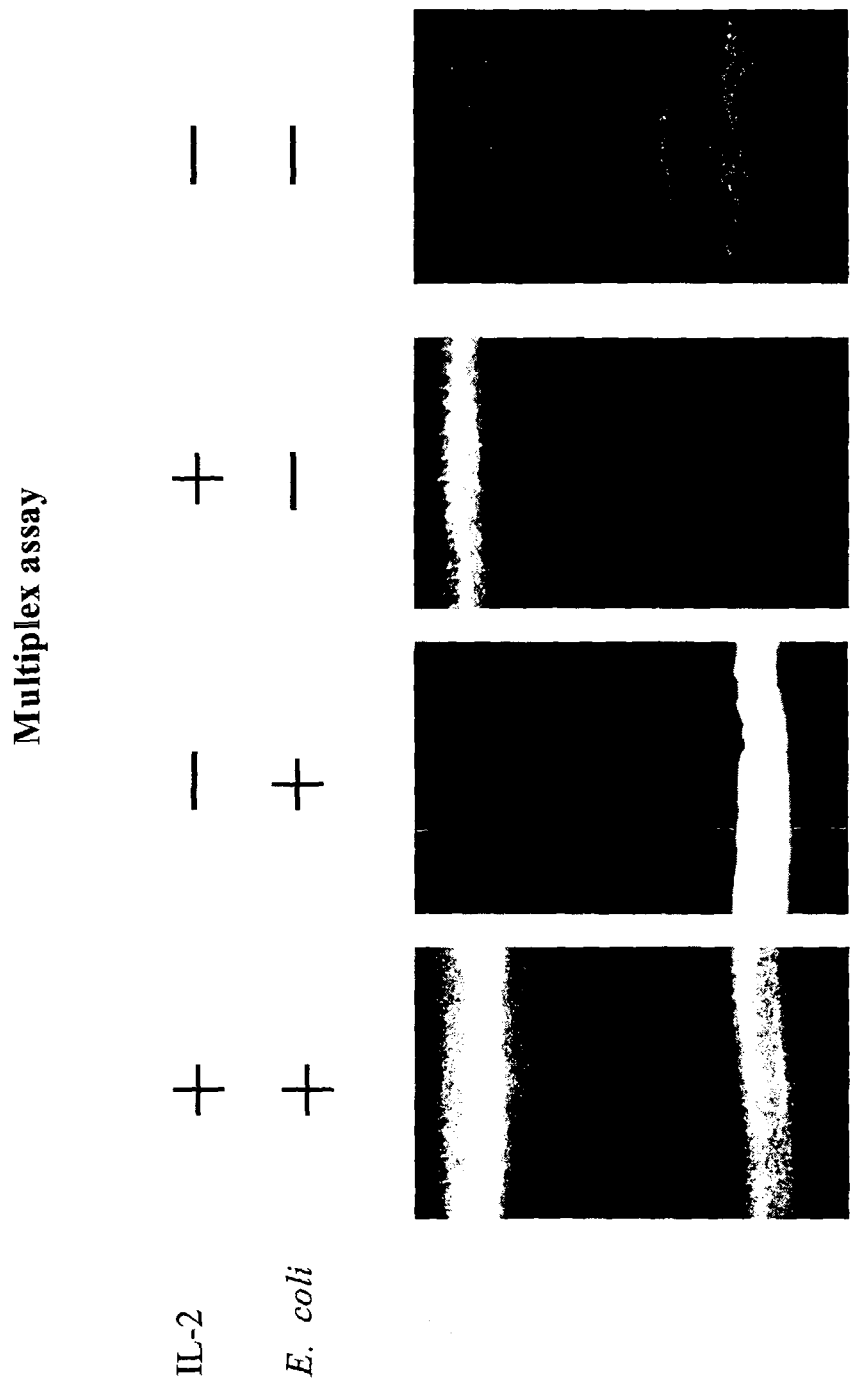

FIG. 9. Ultra-sensitive lateral flow test for multiplex detection of a protein and a bacterium using non-magnified large area imaging (Example 5)

The figure shows the results of a multiplexed lateral flow test using non-magnified large area imaging. The figure shows images of the capture and control lines from test strips onto which were applied samples containing (from left to right) both E. coli and IL-2, E. coli alone, IL-2 alone, and neither E. coli nor IL-2. This figure demonstrates the sensitive lateral flow test and can detect multiple target molecules in the same assay.

Figure 10:
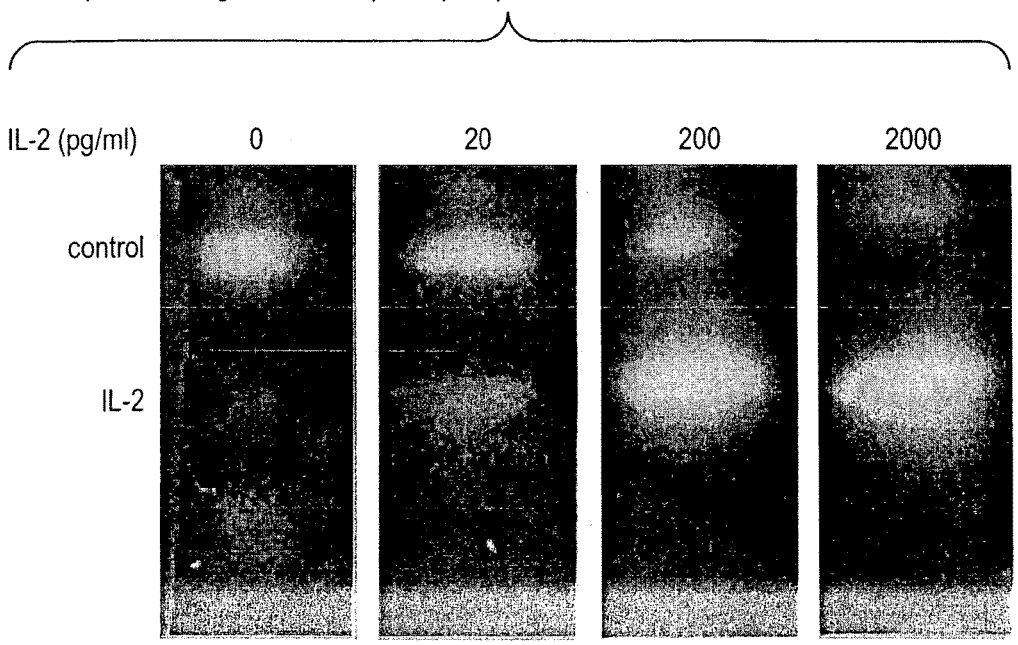

FIG. 10. Ultra-sensitive chemiluminescent lateral flow test for detecting low levels of protein using instant film (Example 7)

The figure shows the results of a lateral flow test using chemiluminescent labeling particles and instant film detection. Capture and control lines from representative test strips are shown. A comparison of the strips onto which were applied samples containing IL-2 (from left to right: 0, 20, 200, and 2000 pg/ml) indicates that as the amount of IL-2 increased, the signal from the capture line also increased. The data show that the invention can detect IL-2 at concentrations as low as 20 pg/ml using instant film. Thus, this test is ultra-sensitive, rapid, easy to perform, and very inexpensive.

Figure 11:
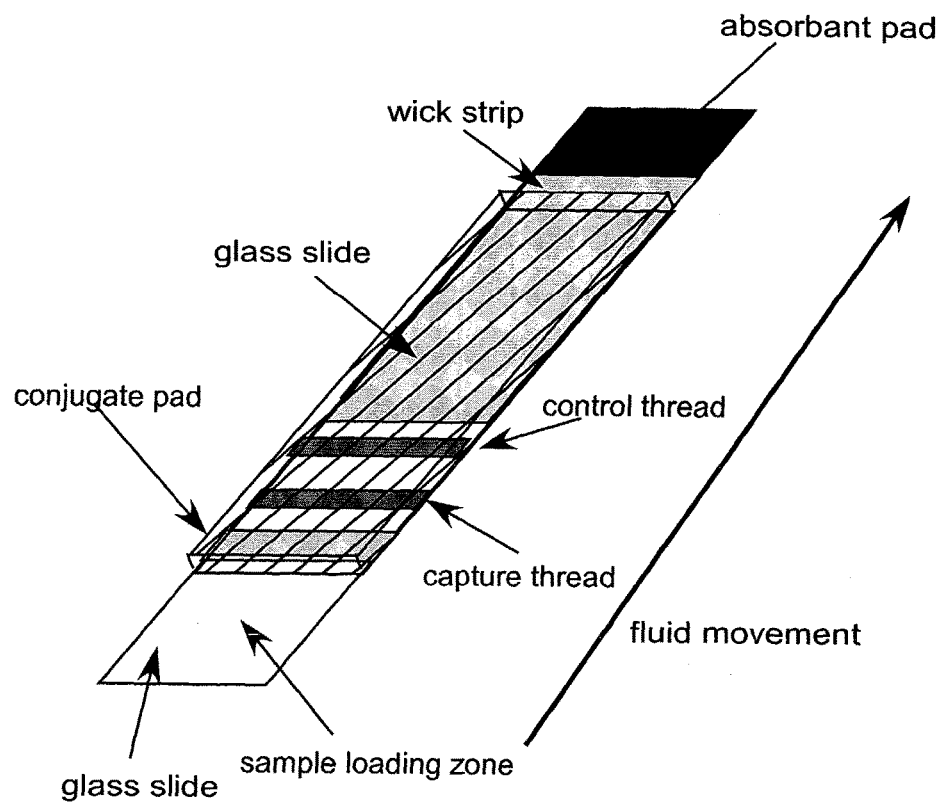

FIG. 11. Schematic of a test device that uses capture threads to select target molecule:labeling particle complexes (Example 8)

The figure shows the construction of the device used in this example. The sample is loaded into the sample zone where it flows laterally into the conjugate pad. The sample, drawn by the absorbent pad at the distal end of the apparatus, solubilizes and mobilizes the detection beads, which flow through the assay threads.

Figure 12:
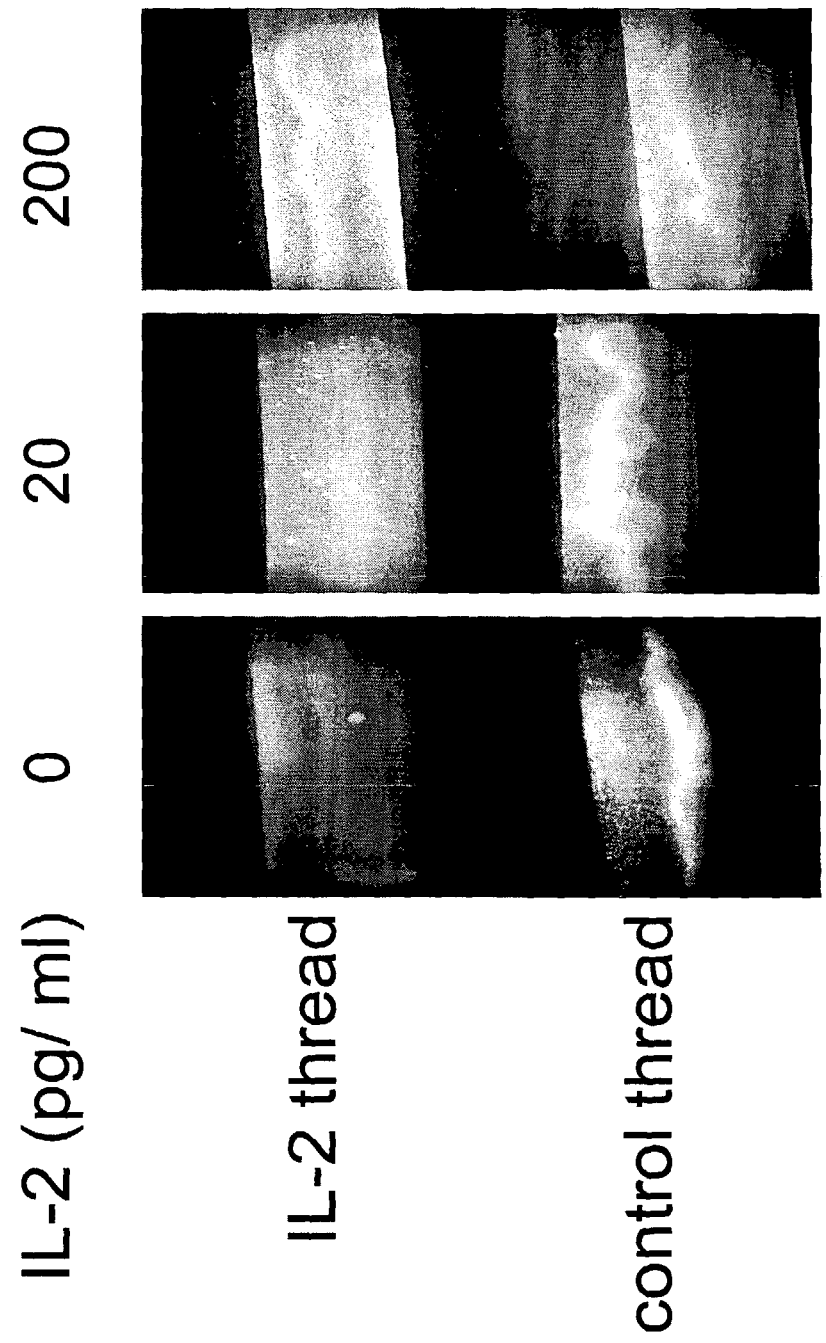

FIG. 12. An ultra-sensitive test for a protein using the capture thread format (Example 8)

The figure shows the results of a capture thread test. The figure shows images of the capture and control threads from tests applied to samples containing IL-2 (0, 20, and 200 pg/ml). The results indicate that the test can detect IL-2 at 20 pg/ml. Furthermore, the concentration dependent speckled appearance of the capture threads suggests that individual labeling particles are being imaged.

Figure 13:
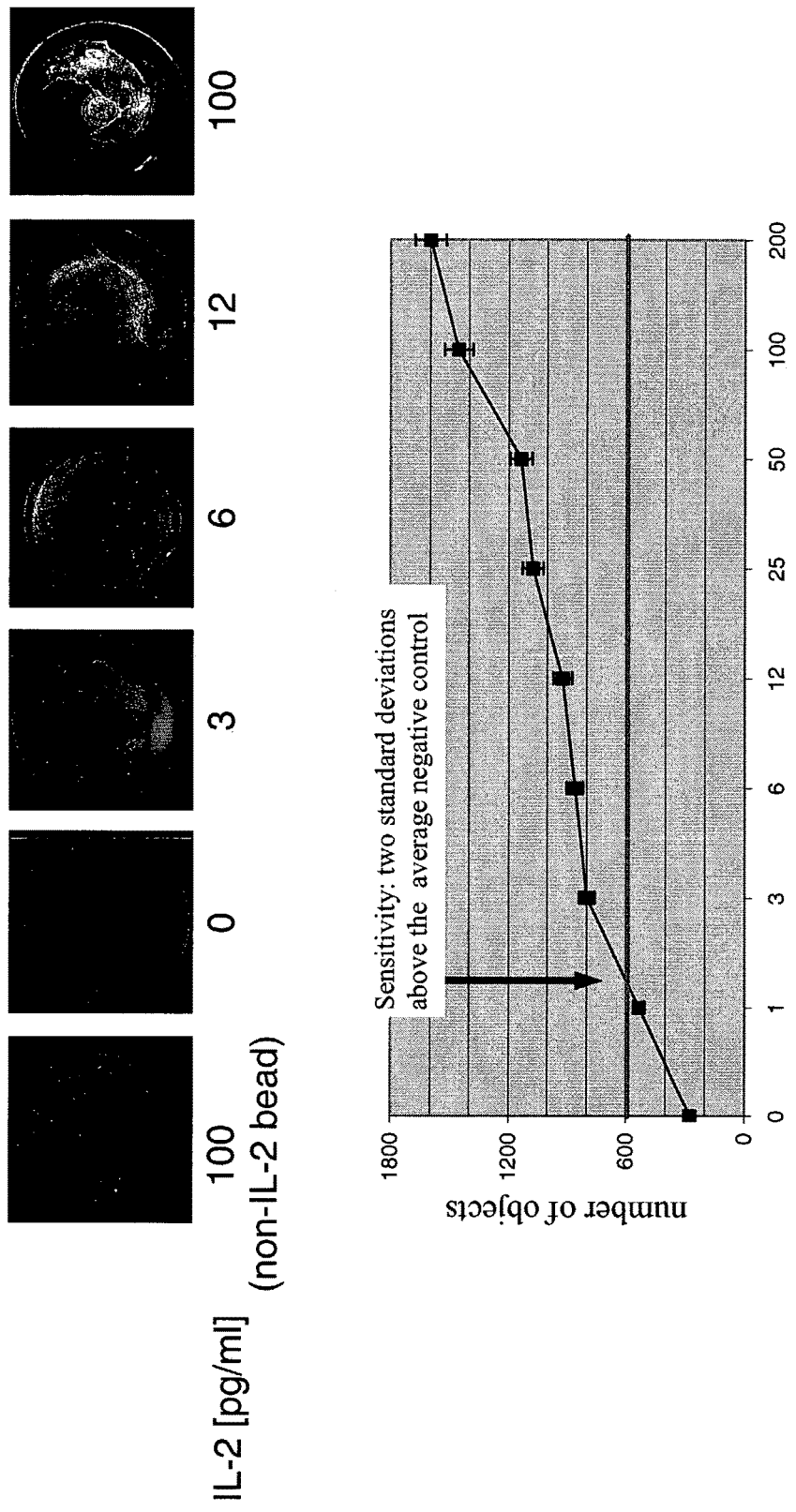

FIG. 13. Sensitive detection of protein molecules using non-magnified large area imaging and solid-phase capture immunoassay (Example 9)

The figure shows the results of a test that scans a sample for the human protein cytokine IL-2 using antibodies bound to the solid-phase to capture the protein. The wells of a micro titer plate were coated with anti-IL-2 antibodies. Dilutions of an IL-2 standard were added to the wells. After an hour of incubation all unbound particles were washed away and anti-IL-2 coated fluorescent particles were added to the wells. After washing, the bound particles were visualized without magnification in the CCD Imager. The negative control (anti-adenovirus particle panel) shows very few particles remain in the well. In the IL-2 panels, an increase in signal is seen as the concentrations of IL-2 standard increases. Signal is due to the interactions of the anti-IL-2 coated wells, the IL-2, and the anti-IL-2 coated particles. The graph shows the sensitivity (defined as two standard deviations above and below the average negative control) of the assay and where the IL-2 concentrations fall in relationships to the sensitivity.

Figure 14:
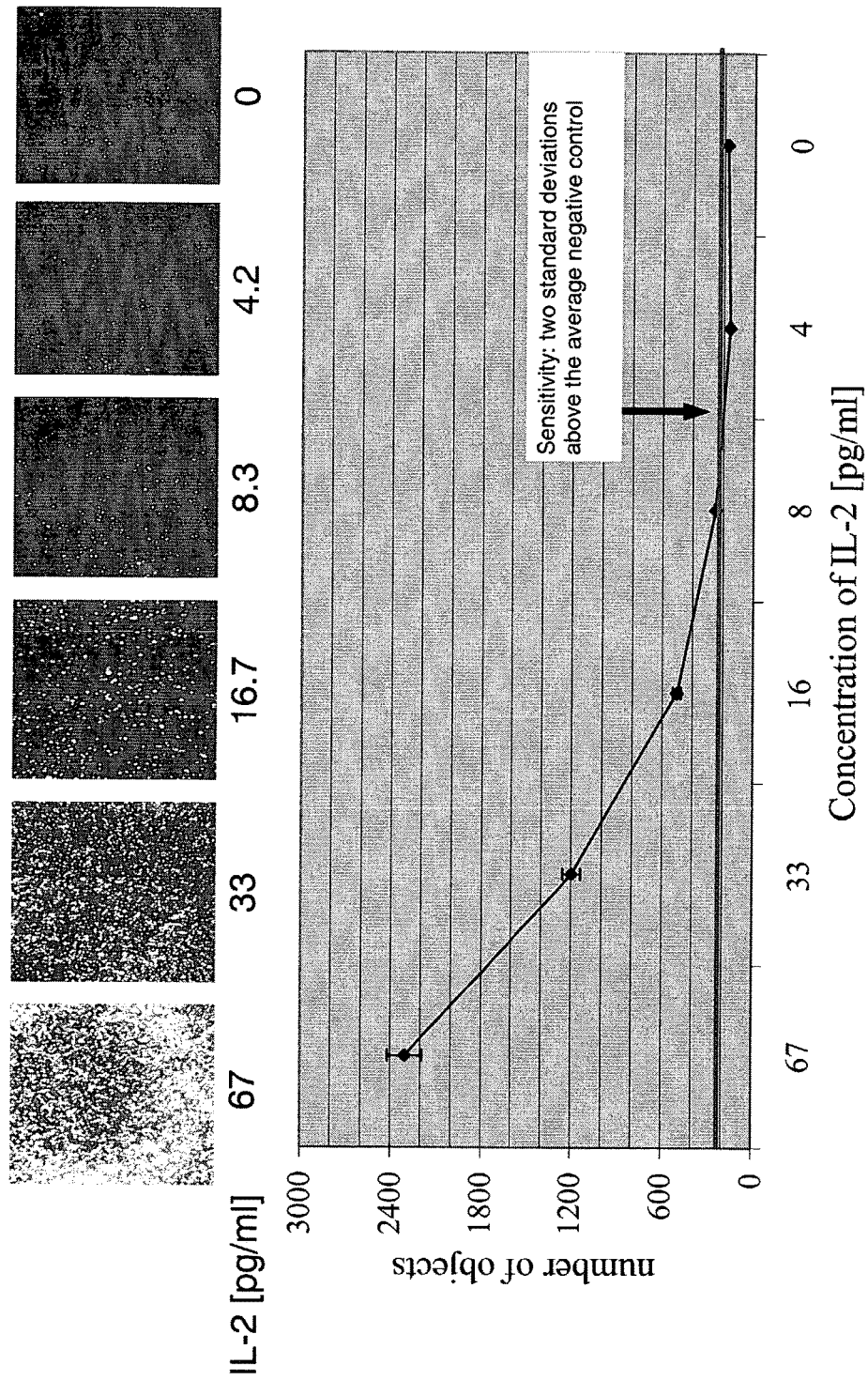

FIG. 14. Sensitive detection of protein molecules using non-magnified large area imaging and liquid-phase capture (Example 10)

The figure shows the results of a test that scans a sample for the human protein cytokine IL-2 using a "dual bead" liquid-phase sandwich method. Dilutions of an IL-2 standard were mixed with anti-IL-2 coated magnetic and fluorescent particles. After incubating 2 hours, the magnetic particles and any bound particles were separated from the other materials, transferred to a micro titer plate, and visualized without magnification in the CCD Imager. The negative control (no IL-2 particle panel) shows few particles remain in the well. In the IL-2 panels, an increase in signal is seen as the concentrations of IL-2 standard increases. The IL-2 panel shows thousands of anti-IL-2 coated fluorescent particles captured by the magnetic particles because of their interaction with IL-2. The graph shows the sensitivity (defined as two standard deviations above the average negative control) of the assay and where the IL-2 concentrations fall in relationship to the sensitivity.

Figure 15:
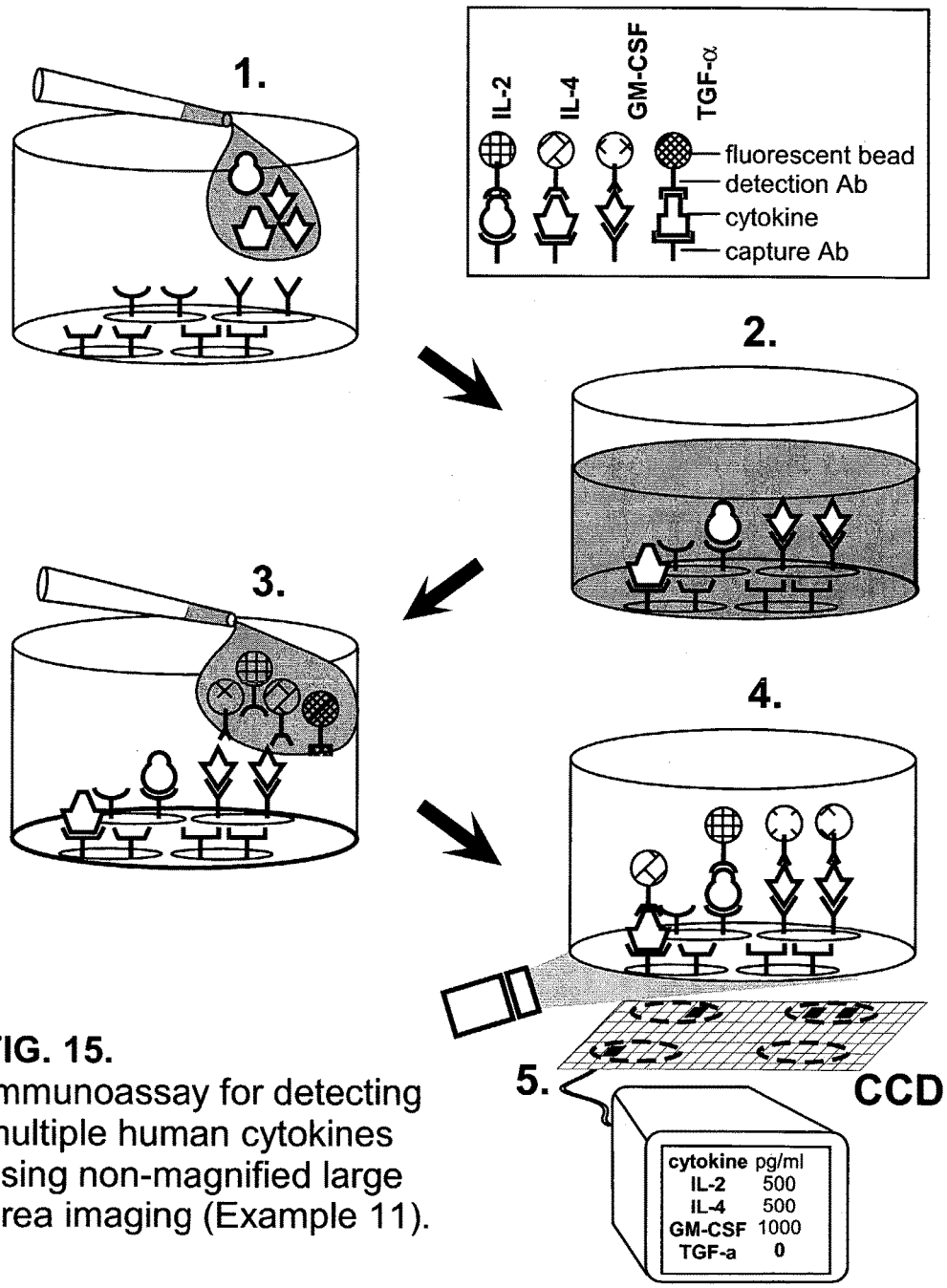

FIG. 15. Immunoassay for detecting multiple human cytokines using non-magnified large area imaging (Example 11)

The figure shows an immunoassay strategy for ultra-sensitive detection of multiple proteins in a microtiter dish.

Figure 16:
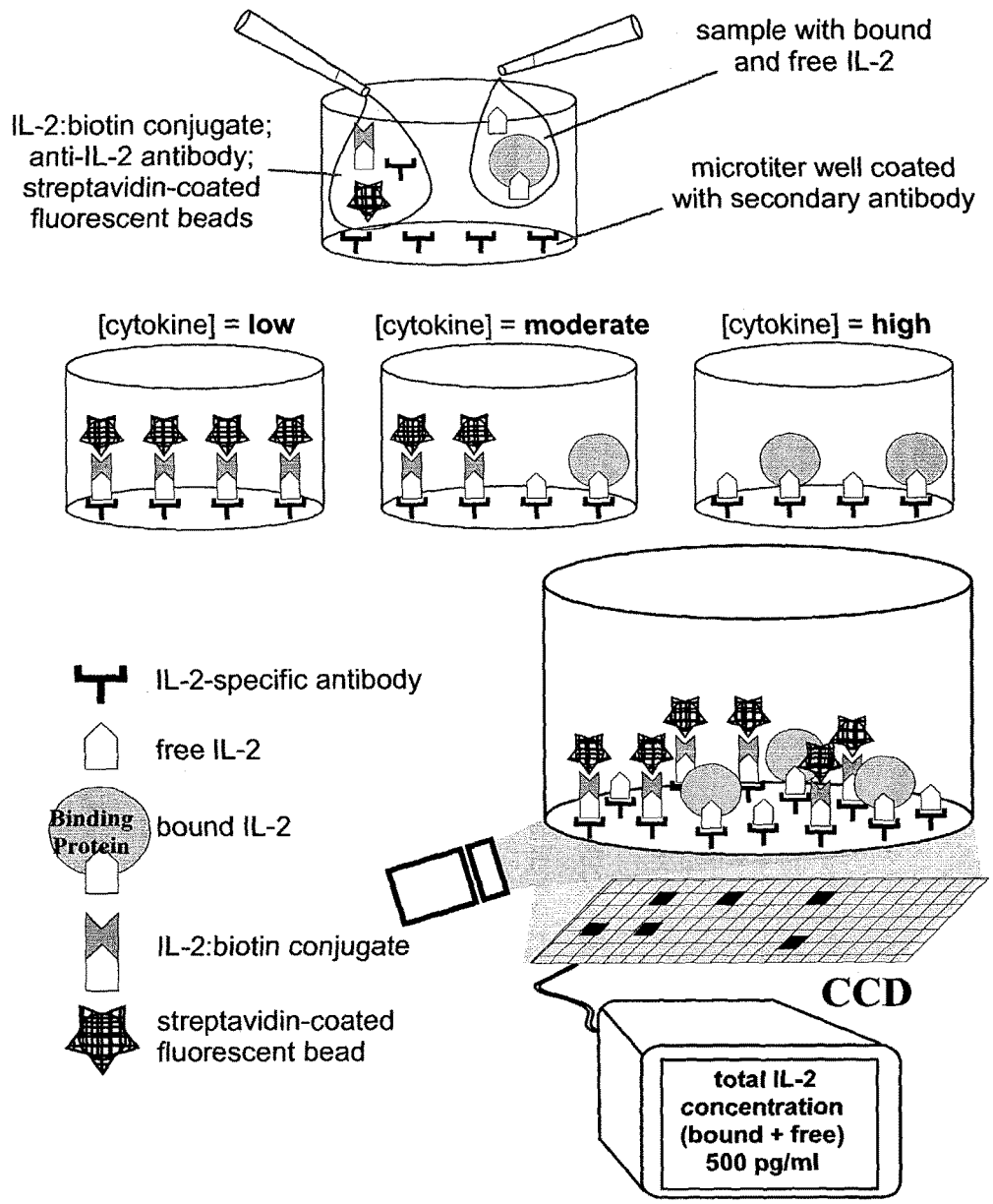

FIG. 16. Competitive immunoassay for total (bound plus free) cytokine IL-2 using non-magnified large area imaging (Example 12)

This figure diagrams a scheme for a competitive immunoassay. A microtiter dish well is coated with an anti-IL-2 capture antibody that binds to an epitope that is exposed in both the free and bound forms of the cytokine. The sample is mixed with an IL-2:biotin conjugate that competes with the cytokine in the sample for binding to the capture antibodies. A streptavidin-coated fluorescent particle, which binds to the IL-2:biotin conjugate, is also included in the mixture. The fluorescent particles bind to the well to the extent that the conjugate competes for the capture antibody sites with cytokine in the sample. Thus, the number of fluorescent particles that are bound reflects the concentration of total cytokine in the sample. Non-magnified large area imaging of the bottom of the well quantifies the extent to which the fluorescent particles bind to the capture antibodies.

FIG. 17. Sensitive detection of nucleic acid molecules using a dipstick format and non-magnified large area imaging (Example 13)

The figure shows the results of an assay that detects viral DNA using a dipstick format and non-magnified large area imaging. Dilutions of biotinylated viral DNA were spotted onto a nylon membrane. As a negative control, non-biotinylated viral DNA was also spotted. After blocking to prevent non-specific binding, the membrane strip was dipped into a solution containing avidin-coated red fluorescent beads. The bead solution migrated up the membrane by capillary action and contacted, in the process, the filter-bound DNA. The membrane was washed and then analyzed by CCD-based non-magnified large area imaging. The bright spots in the images in the figure indicate fluorescent signal obtained from the various DNA spots on a single membrane strip. The number of copies of DNA in each spot is indicated to the right of each image. The cartoon on the left shows how the DNA spots were positioned on the dipstick.

FIG. 18. Non-amplified multiplex SNP analysis using a lateral flow format and non-magnified large area imaging: Oligonucleotide ligation and sample application This figure diagrams the first steps of the test described in Example 15, the final steps of the test are shown in FIG. 19. Pairs of allele-specific oligonucleotides are hybridized to genomic DNA. One pair member is biotinylated (oligonucleotides with yellow triangles in the figure). The other pair member has a terminal nucleotide that corresponds to a single-nucleotide polymorphism and has a unique polymorphism-specific oligonucleotide tag (oligonucleotides with an explicit base—A, T, G, or C—in the figure). After ligation, the oligonucleotides are applied to a lateral flow chromatography strip. The oligonucleotide tag sequences hybridize to the tag complements that are arrayed in stripes on the lateral flow membrane. Only the tag sequences that correspond to polymorphisms present in the genomic DNA are ligated to biotinylated oligonucleotides. Therefore, only the stripes of tag complements corresponding to polymorphisms in the genomic DNA sample will hybridize to biotinylated oligonucleotides.

FIG. 19. Non-amplified multiplex SNP analysis using a lateral flow format and non-magnified large area imaging: Detection This figure diagrams the final steps of the test described in Example 15, the first steps of the test are shown in FIG. 18. As shown in FIG. 18, after lateral flow chromatography, biotin molecules will be associated with stripes on the membrane containing tags that correspond to the genotype of the genomic DNA sample. This pattern of stripes is detected by binding to particles that are co-coated with streptavidin (which binds to the biotin moieties) and alkaline phosphatase. After adding a substrate of alkaline phosphatase that yields a chemiluminescent product, the stripes containing biotinylated oligonucleotides are detected with a CCD imager.

DETAILED DESCRIPTION OF THE INVENTION

Overview of the Invention.

The invention rapidly and cost-effectively scans a minimally processed sample for low levels of target molecules. The powerful features offered by the invention arise from a novel diagnostic approach that combines modern high-intensity labeling, cost-effective imaging technology, and non-magnified large-area detection.

Figure 1:
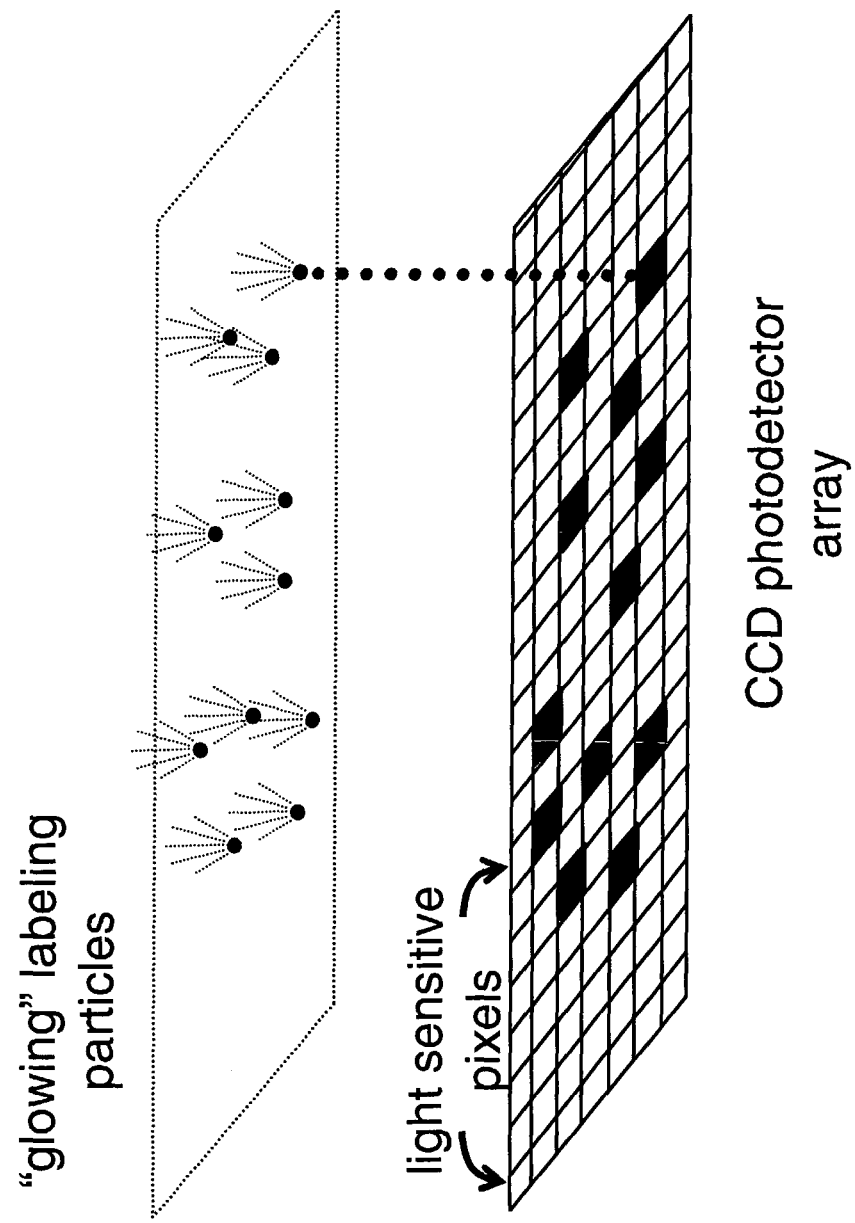
FIG. 1. The principle of non-magnified large-area imaging of individual signal generating particles with a CCD array.

The use of non-magnified imaging to detect a small number of microscopic labels spread out over a large area is shown schematically in FIG. 1. The embodiment depicted in FIG. 1 uses a digital camera (CCD chip) to capture an image of an area that is much larger than the individual labeling particle. The CCD chip comprises an array of photosensitive pixel elements. Light from a "glowing" particle at one position in the detection area impinges on pixel elements at the corresponding position of the CCD chip. The end-user receives information about the number of particles in the sample from a computer that processes the image data (i.e., the number and intensities of the illuminated pixels) acquired from the CCD chip.

In order to understand the principles used by the invention better, it is helpful to consider a specific embodiment. FIG. 1 diagrams a method that quantifies the amount of the human protein cytokine IL-2 in a blood sample. The well of a microtiter dish with an optically clear base is coated with an antibody that binds to a site on the IL-2 molecule. A drop of blood containing IL-2 molecules is added to the well. Fluorescent particles (dyed with the molecule fluorescein) are also added to the well. These particles are also coated with an antibody that specifically binds to IL-2 (although this antibody binds to a site that is distinct from the site to which the capture antibody binds). The IL-2 molecules in the blood bind to both the fluorescent beads and the capture antibody forming a "sandwich" on the bottom of the well.

The result of sandwich formation is that fluorescent beads become anchored to the bottom of the well. When no IL-2 is present, no sandwiches are formed, and no fluorescent beads become anchored to the bottom of the well. The more IL-2 there is in the blood, the more beads become coated with IL-2, and the more beads become anchored to the bottom of the well. The next steps image and enumerate these beads.

Illuminating the bottom of the well (the detection area) with light in the excitation range of fluorescein elicits fluorescence emission by the fluorescent beads that are anchored to the bottom of the well. The fluorescent image of the particles is collected, focusing the emitted light on the surface of a CCD chip without magnification. Fluorescent light from each particle impinges on one pixel or a small cluster of pixels causing a localized electronic signal that is relayed from the CCD chip to a computer where it can be stored in the form of an image file. Image analysis software enumerates the number of beads anchored to the bottom of the well by counting the number of pixel clusters responding to light from the particles.

The invention can be used to construct tests using a number of types of formats, labeling methods, category-binding molecules, and detection methods. However, the tests have several key features in common. The steps and processes that are common to many embodiments of the invention are described below.

The general methods of the invention include the following steps:
Step 1: Formulating a test question, choosing a sample, test format, and category-binding molecule(s)
Step 2: Preparing labeling particles
Step 3: Binding target molecules in the sample to the labeling particles
Step 4: Selecting or capturing target molecule:labeling particle complexes
Step 5: Identifying and quantifying target molecules present in the sample by detecting the selected or captured target molecule:labeling particle complexes
Step 1: Formulating a Test Question, Choosing a Sample, Test Format, and Category-Binding Molecule(s)

Formulating the question to be answered by the test is the first step in creating a new detection method based on the invention. Some examples of important questions that industrial and clinical microbiologists must address are listed in Table 2. Articulating the test question generally defines the sample type that must be tested (e.g., environmental water, urine, or a pharmaceutical finished product). The sample type and volume are important parameters in choosing the test format.

TABLE 2

Examples of questions answered by tests based on the invention

Does the environmental sample contain any
of 6 particular biowarfare agents?
What is the total viral content of an environmental sample?
Does the blood of this patient contain levels of 4
specified proteins that are markers of sepsis?
Does the saliva of this patient contain any of
12 specified drugs-of-abuse?
What level of pharmaceutical drug X is in the
blood of this patient in a clinical trial?
Are any of four specified foodborne pathogens
or 2 toxins present in this food product?
Does a cervical sample contain any of 5 specified
sexually transmitted disease pathogens?

TABLE 2-continued

Examples of questions answered by tests based on the invention

Does the blood of a patient contain any of a panel of 12
proteins correlated with heart disease?
Does the blood of a patient contain any of a panel of 12
proteins correlated with breast cancer?
Does the DNA of a patient have any of 12 alleles that are
correlated with cardiovascular disease?

The test format is chosen based on several factors including the sample volume, sample content (i.e., are there particulates or cells?), number of categories of targets, operator skill level, cost constraints. Examples include familiar lateral flow and microtiter dish formats in addition to novel formats. A range of formats are outlined in the examples below.

Having formulated the test question, the categories of target molecules become clear. These are the molecules detected by the test. For tests that survey a sample for a panel of small molecules (e.g., drugs-of-abuse) or for protein markers of cardiovascular disease the target molecule molecules are simply the drugs-of-abuse or the protein markers, respectively. For tests that survey a sample for more complex targets (such as a bacterial pathogen or white blood cells containing proteins correlated with leukemia), the target molecules are molecules that are characteristic or specific to the target.

Once the categories of target molecules become clear, category-binding molecules are chosen. Category-binding molecules bind specifically to the target molecules. The invention supports a wide variety of category-binding molecules which are appropriate for different target molecules. For example, antibodies can be used as the category-binding molecules for a variety of target molecules (e.g., hormones, carbohydrates, and proteins). For determining the genetic makeup of an individual, DNA oligonucleotides may be used, for example.

Step 2: Preparing Labeling Particles

The invention's ability to detect individual microscopic target molecules without optical magnification or expensive instrumentation depends on specifically labeling the target molecules at high signal intensity. Labeling is achieved by specifically binding labeling particles to the target molecules via an association with category-binding molecules. The labeling particles have two functionalities: signal generation and specific binding. Various particle compositions, signal generating moieties, and category-binding molecules can be used to make labeling particles with these functions.

To make labeling particles that bind to the target molecules chosen in Step 1, category-binding molecules are conjugated to particles using various methods which are known by those familiar with the art (see, for example, Hermanson, G., *Bioconjugate Techniques* (Academic Press, 1996) and specific examples below). Sometimes signaling moieties are conjugated to the particles using the same set of conjugation techniques (e.g., for enzymatic signaling moieties).

Numerous types of signaling moieties are used to allow the particles to emit strong signals of the appropriate type for a given test. For example, microparticles, such as polystyrene beads (e.g., 1 micron diameter) can be dyed with fluorescent dyes to create intensely fluorescent particles. Fluorescently dyed polystyrene microparticles (e.g., 1 μm in diameter) can incorporate millions of fluorophore signaling elements. Alternatively, particles can be conjugated to enzymatic signaling moieties such as alkaline phosphatase, which can catalyze the formation of fluorescent, chemiluminescent, or visibly colored products. Other types of labeling particles include quantum dots and resonance light scattering particles. These small particles can also be complexed with larger particles to increase the signal strength and signal complexity.

The invention's ability to scan simultaneously for numerous disparate categories of target molecules stems from the ability to differentiate the signals derived from the different categories of target molecules. The invention discriminates between categories of target molecules in two general ways. One method, called signal differentiation, labels each category-specific family of category-binding molecules with signaling moieties such that it has a unique signal signature. The ability to generate and detect large numbers of distinct signal signatures (i.e., high signal complexities) enables the construction of tests that scan for numerous categories of target molecules (i.e., highly multiplexed tests). Another method for distinguishing between multiple categories of target molecules, geometric differentiation, relies on depositing different categories of target molecules in different regions of the detection area. Geometric differentiation, which can be independent of the signal signature of signaling moieties, is used, for example, in multiplexed lateral flow tests. Geometric differentiation is discussed in Step 4 below.

The invention can exploit various types of signal character including fluorescence, scattered light, light polarization, thermal radiation, chemiluminescence, and radioactivity. Examples of signaling moieties and detection schemes using various signal characters appear below. There can be multiple signal classes within a signal character. For example, if the signal character is fluorescence, various characteristic emission spectra comprise the signal classes (e.g., red fluorescence, green fluorescence, and blue fluorescence). Alternatively, red fluorescent microparticles that are dyed with different concentrations of the same fluorophore also employ fluorescence as the signal character, but in this case, the different intensities of the particles constitute the classes of signal character, i.e., fluorescence intensity is the quality of the signal character that differentiates one group of particles from another.

Attaining a high signal complexity is key to developing certain tests that scan for numerous types of target molecules (i.e., tests with high categorical complexity).

Achieving High Signal Complexity.

The number of distinguishable labels (or signaling moieties) in a mixture is called the signal complexity. For highly multiplexed tests, it is sometimes advantageous to use signaling moieties with high signal complexity. Three general approaches that can be used with this invention to generate high signal complexity are: (1) distinct labeling, (2) combinatorial labeling, and (3) ratio labeling.

1. For distinct labeling, probes in different probe families are tagged with a single signaling moiety that can be readily detected in the presence of all other signaling moieties in the experiment. Thus far, it has been difficult to achieve distinct labeling at high signal complexities. This difficulty occurs because most labeling methods use optical signals (e.g., chromogenic, fluorescent, or chemiluminescent) or radioactive labeling. Because of the spectral bandwidth of optical signals and the limited range of signals detectable by current instruments, the resolvable signal complexity using optical signals is rather small. For example, the resolution of dozens of fluorophores with distinct emission spectra is currently impossible because of spectral overlap. One method that can be used for distinct labeling is the use of micro-transponders (e.g.,
U.S. Pat. No. 6,001,571). Each micro-transponder emits a distinct radio wave signature. Thus, labeling with micro transponders and other as yet developed methods for distinct labeling have the potential to be used in conjunction with the invention.

2. Another way to achieve the high signal complexity used in the invention is to apply a combinatorial labeling approach. Combinatorial labeling is a technique for achieving high signal complexity using a relatively small number of distinct signaling moieties. With this approach, distinct combinations of signaling moieties are bound to different targets. Currently, fluorophores are a favored class of signal moiety for molecular diagnostics. However, given the complications involved in analyzing multiple distinct fluorophores (arising in large part from overlap of the excitation and emission spectra), it is only currently practical to incorporate about seven or fewer conventional fluorophores. Used in combination, seven fluorophores can be used to generate 127 distinct signals (N fluorophores generate $2^N-1$ combinations). High signal complexity can also be achieved via combinatorial labeling using other types of signaling moieties. For example, particles impregnated with different dyes, particles that fall into different discrete size classes, or transponders emitting distinct radio signals could be used with this approach. Combinatorial labeling using fluorophores has recently been applied with success for human karyotyping (Speicher et al 1996, supra; Schrock et al 1996, supra). Instrumentation and software for analysis of combinatorial labeling experiments is commercially available.

3. High signal complexity can also be obtained using the ratio labeling approach (Fulton, et al 1997, supra). In ratio labeling, as in combinatorial labeling, many distinct types of signaling moieties are generated using a relatively small number of distinct signaling elements. In contrast to combinatorial labeling, the signaling moieties in ratio labeling are distinguished by the ratio of the signaling elements. For example, two fluorophores, X and Y, with different excitation/emission characteristics can be used to dye polystyrene particles. Different relative concentrations of the fluorophores ([X], [Y]) are applied to different sets of particles. For example, eight different concentrations of X and eight different concentrations of Y can be used to dye particles in all combinations ($X_1Y_1$, $X_1Y_2$, $X_8Y_7$, $X_8Y_8$) resulting in 64 classes of distinguishable particles. Ratio labeling simplifies instrumentation, as only a small number of signal types need be used. Signal elements, other than fluorophores and including non-optical signal elements, can also be used to generate high signal complexities using a ratio labeling approach.

Step 3: Binding Target Molecules in the Sample to the Labeling Particles

The method and format for binding the target molecules in the sample to the labeling particles depends on the type of sample, the nature of the target molecules, and the chosen format of the test.

An important attribute of the invention is its compatibility with rapid and simple sample preparation protocols. For many applications, in fact, there is no required sample preparation. This represents a major advantage over other sensitive diagnostic methods, such as nucleic acid amplification-based techniques, which require much more demanding sample preparation procedures to eliminate enzyme inhibitors. Tests that survey samples for soluble molecular markers, for example, often do not require any sample preparation before binding to the labeling particles. For some tests, in which the target molecule is part of a larger complex or sequestered in a larger complex, the larger complex can be dissociated as part of the sample preparation step. For example, for a test that surveys for the presence of viral core protein on the interior the HIV virus, the virus particle could be dissociated using a detergent. Similarly, for genetic analysis, cells containing the nucleic acid target molecules are generally broken open (e.g., by various chemical or physical treatments) and the double stranded DNA denatured to allow for nucleic acid hybridization.

Various formats used by the invention have the advantage of allowing rapid binding of the labeling particles to the target molecules in the sample. For example, contacting large numbers of labeling particles and target molecules in liquid samples forces collisions to occur much more rapidly than in typical ELISA formats, in which the target molecules typically diffuse to one end of the reaction chamber before collision can occur. Rapid binding kinetics are also a feature of test formats (e.g., lateral flow tests) in which contacting occurs inside a porous membrane Step 4: Selecting or Capturing Target Molecule:Labeling Particle Complexes The selection step has several important functions including separating the target molecule:labeling particle complexes from unbound labeling particles, depositing the target molecule:labeling particle complexes in the detection zone (e.g., the focal plane of the optical system for some embodiments) removing the sample material from the target molecule:labeling particle complexes, and (for some test formats) localizing specific categories of labeled target molecules to distinct regions of the detection area.

For assays in which the sample is fixed to a solid substrate before the binding step, the unbound category-binding molecules and signaling moieties are generally removed by washing. Examples include applications that use in situ hybridization and immunocytochemical methods.

Other test formats are carried out in the liquid phase, for example in microtiter wells. For some tests the selection step occurs via binding of the target molecule:labeling particle complexes to capture molecules on the detection surface of a microtiter well. In these tests, diffusion is the means by which the contact is made with the capture molecules. For other applications, the target molecule/category-binding molecule/signaling moiety complexes are deposited on the surface. Methods for depositing the target molecule complexes on a surface include centrifugation, filtration, gravitational settling, magnetic selection, or binding to surface bound category-binding molecules, e.g., capture antibodies. In some cases (e.g., magnetic separation), a distinct moiety, the selection moiety, is used. Magnetic microparticles coated with category-specific antibodies are an example of a selection moiety. The unbound category-binding molecules and signaling moieties generally remain in the liquid phase and can be removed. However, if the detection procedure (e.g., optical imaging) selectively analyzes the solid surface with a narrow depth of field, the unbound material (lying outside of the plane of focus) sometimes need not be removed.

For some applications, combinations of selection procedures are useful. For example, the sample can be filtered through membranes with defined pore sizes before contacting the labeling particles. For example, a filter system that only lets particles between about 0.5 and 5 microns in size could be used to detect the presence of anonymous bacteria. Such a test could be based on a labeling particle that binds to any protein that contains a tyrosine, for example. Selecting for other size ranges could enable tests for anonymous viruses, free proteins, or eukaryotic cells.

Lateral-flow and flow-through formats are arguably the most successful test formats in point-of-care testing. These formats exploit the advantages of capillary flow in bibulous membranes. They generally select the target molecule:labeling particle complexes using capture molecules (i.e., surface-bound category-binding molecules). Unbound labeling particles flow out of the capture zone by capillary action. Another important advantage of membrane-based assays is the ease of multiplexing by using geometric differentiation.

Geometric differentiation is an important method when surveying samples for multiple categories of target molecules (i.e., in multiplexed tests). Geometric differentiation has the advantage, when compared to high signal complexity multiplexed tests (see Step 2), of requiring only a single signal signature for multiplexed tests. In a typical immunoassay that uses geometric differentiation, different category-specific capture antibodies are deposited in distinct areas in the detection zone (e.g., different stripes in a lateral flow test or different spots in a flow through or microtiter well-based test). Thus, different categories of target molecules are captured in different pre-determined areas of the capture zone. Other types of capturing moieties that are analogous to capture antibodies include antigens, ligands, and nucleic acids. Other formats, including those using microfluidic channels and those using "capture threads" (thin strips of material coated with capture molecules) can also be used with geometrical differentiation.

Step 5: Identifying and Quantifying Target Molecules Present in the Sample by Detecting the Selected or Captured Target Molecule:Labeling Particle Complexes This step detects, identifies, and quantifies target molecules in the sample using large area imaging analysis of the target molecule:labeling particle complexes that are anchored in the detection zone. The step itself generally comprises the steps of imaging, image analysis, and report generation.

The invention can detect microscopic labeling particles with no magnification. This powerful feature is supported by high intensity labeling methods and high efficiency optics to direct photons emitted by the microcolony into a small number of pixels of photodetector arrays. Low magnification imaging facilitates the imaging of a large area which, in turn, facilitates scanning large samples.

The imaging method used depends on the type of signal generation chosen in step 2. For example, the imaging process is different depending on the optical property or signaling character that is used for signal generation. For some signal characters (e.g., reflectance, fluorescence, light scattering, or absorbance), the complexes in the detection zone must be illuminated by a light source. For others (e.g., chemiluminescence or thermal radiation), illumination is not required.

Detection of individual labeling particles is naturally quantitative and ultra-sensitive. Quantification can be accomplished by manually counting individual labeling particles in a photographic or digital image or by using automated image analysis of digitized images. Integrating signal intensity over the sample can also be used to quantify the target cells. Signal integration is particularly useful with samples containing high concentrations of target cells. In these cases, resolving coincident signals may not always be possible.

Decoding the signatures of the labeling particles allows identification of numerous categories of target cells. An important goal of this step is to identify the category of target cells in the sample by determining the signature of target molecule:labeling particle complexes.

The CCD camera-based imager, shown in FIG. 1 is a useful device for large area imaging when fluorescence is used as the signal character. This device was used to collect the data for many of the examples below. Excitation light is provided by introducing light from a high intensity white light source (1000 W Xenon arc lamp, Model A-6000, Photon Technology Incorporated, Monmouth Junction, N.J.) into a liquid light-guide (5 mm core diameter, Model 380, Photon Technology Incorporated, Monmouth Junction, N.J.). The liquid light-guide carries the light to an excitation filter-wheel (BioPoint FW, Ludl Electronics, Hawthorne, N.Y.) and directs the filtered beam (e.g., 9 mm or more in diameter) onto the detection surface containing the labeling particles. The apparatus can detect labeling particles in various configurations (e.g., on (or in) porous membranes, microscope slides, coverslips, or tubes or wells with flat, optically clear, bottoms). The incident light strikes the detection surface inducing fluorescence in the target cells. A portion of the emitted fluorescent light is collected by a high-collection efficiency lens system and transmitted through an emission filter-wheel (BioPoint FW, Ludl Electronics) to a CCD camera (Orca II, Hamamatsu, Bridgewater, N.J.). The design and construction of the optical train is based on principles and practices known to workers familiar with the art.

The invention can also incorporate other types of photodetectors and other configurations. The sensitivity of the imaging system can be increased by choosing a more sensitive camera (e.g., a camera cooled to a lower temperature, or a camera that uses a back-thinned chip). Alternatively, the detection sensitivity and resolution can be increased by implementing a line scanning system (e.g., BT Image Array; Hamamatsu). For line scanning, a linear CCD or photodiode array (e.g. 1×500 or 1×1000 pixels) is used to capture the image. The resolution in one dimension corresponds to the number of array elements, while the second dimension is generally captured by moving the sample slide perpendicularly under the linear array. Since there are fewer elements, similar sensitive linear arrays are typically less expensive than area format CCD cameras.

The instrument diagrammed in FIG. 3 can be configured to measure multiple samples by using an X-Y positioning Stage (BioPoint XY, Ludl Electronics) to move the experimental samples over the excitation and collection optics. Image-Pro and Image-Pro add-ins control all instrument components and image acquisition. Filter wheels are managed with the ScopePro add-in (Media Cybernetics, Baltimore Md.), and the StagePro add-in (Media Cybernetics, Baltimore Md.) handles stage positioning, while the camera control is via the Hamamatsu Orca II driver (Hamamatsu, Bridgewater, N.J.). Image-Pro Plus is also used for Image-Processing and analysis as described below.

Embodiments of the invention using white light illumination utilize spectral filters to provide an optimal excitation peak for each of the fluorophores. The white light spectrum is large, allowing a wide variety of fluorophores to be selected to eliminate emission spectra overlaps. Typically spot sizes achievable with white light illuminators, e.g., 2 mm to 5 mm, are appropriate for large area imaging. Since filter changes are relatively simple and can be automated, white light systems are very adaptable, allowing the same apparatus to be used for tests that use distinct sets of fluorophores.

The collection efficiency of the system shown in FIG. 3 is maximized by incorporating a custom designed collection optic consisting of two components: a collection objective and a focusing element. The collection objective has high collection efficiency ($\geq f\#/1.2$) and outputs a relatively collimated beam. The focusing lens captures the light output from the collection objective and focuses it onto the detection surface of the CCD. The optics are designed in two parts to allow a filter wheel to be inserted in the path of the collection lens. For certain embodiments of the invention, e.g., those that do not require filter changes, it may be desirable to include a tapered optical fiber bundle for achieving high collection efficiency. The fiber optic bundle contains fibers that collect light proximally to the sample and channel the light directly to a CCD chip. Alternatively, the invention can detect signals very sensitively using direct proximal detection in which the sample is applied directly or in close proximity to the CCD chip (for highest sensitivity to the back of a back-thinned CCD chip).

In addition to the white-light, multi-spectral system described above, we have also developed a simpler single-color fluorescence imaging system for non-magnified large area imaging. In the system shown in FIG. 4, excitation light is provided by a 532 nm Frequency-Doubled Diode Laser (50 mW, Model #BWT-50E, B&W Tek, Newark, Del.). Since this detection uses a single color, filter wheels are not necessary. A single excitation filter removes harmonic spectra from the laser output (Model HQ532/10x, Chroma Technology, Brattleboro, Vt.), and a single emission filter (Model HQ620/60m, Chroma Technology, Brattleboro, Vt.) allows only specific wavelengths to pass to the CCD camera. This system may also use a less-expensive CCD camera (Model KX-2E, Apogee CCD, Auburn, Calif.) than the one described previously, to capture images. The instrument can easily be adapted to multicolor analysis by incorporating multiple lasers and filter sets.

The CCD cameras incorporated in the invention are generally cooled to a temperature between −5° C. and −50° C., sufficient for integration times from ten seconds to about two minutes (depending on the camera sensitivity) with minimal camera noise build-up. Longer integration times generally give higher sensitivity by allowing the collection of the photons emitted from the fluorophores for an extended period. Long integration times are inappropriate for line scanning; however, there are back-thinned linear arrays available that have very high quantum efficiencies, increasing sensitivity.

The invention can also use interferometer-based spectral imaging for the detection and decoding of signals (Schrock, E., 1997, supra). Using this technique, light emitted or scattered by signaling moieties is split into two paths, passed thorough prisms (so that different wavelengths travel different distances), and allowed to recombine to create an interference pattern. Fourier analysis of the interference pattern generates a spectrograph for each point in the image.

For point-of-care applications including applications requiring portable systems, the invention can be configured to minimize weight and size. For some embodiments, instrumentation can be eliminated completely (e.g., when the labeling particles are visualized by color detection) or greatly simplified (e.g., by using instant film in place of electronic detectors). If desired, images collected on film can be digitized in commercial scanners for data storage and for digital image analysis. Alternatively, photodetectors can be used without an optical system by using proximal imaging (the photodetector is placed essentially against the detection zone). For maximum portability, the light source can be eliminated by using labeling particles with non-illumination dependent signaling character (e.g., chemiluminescence).

For embodiments of the invention that generate digital images, computer software identifies and quantifies the target labeling particles. For a typical assay in which different classes of fluorescent signaling moieties are used, the software superimposes the appropriate fluorophore-specific images, identifies the target cells by determining which signature or combination of signals is emitted by each target labeling particle, and enumerates each category of target labeling particle that is present in the sample. The software may also: (1) correct for illumination non-uniformity; (2) correct for fluorescence cross-talk through a deconvolution matrix; (3) align images using registration marks, e.g., imprinted on the substrate; (4) assign an ID code to each imaged labeling particle in the sample based on comparison to a look up table; (5) record the imaged sample bar code for sample identification; and (6) automatically save output data, images, and bar code to a database that can be queried, e.g., via a web browser interface. Commercially available image analysis packages can be used to provide these functions. Software packages for multicolor image analysis can be used (e.g., Image-Pro, Media Cybernetics; MetaMorph, Universal Imaging; MatLab; The MathWorks).

It is useful to outline here the software packages and methods that were used to analyze the fluorescence data collected in many of the examples that follow. The detection surface is imaged to determine the number of fluorescent objects and/or the total fluorescent signal. The fluorescence was captured from the detection zones by a CCD camera and stored as a TIFF (Tagged Image File Format) image file that contains records of pixel locations and intensities. Three approaches were used to quantify the assay results. The total integrated signal of the imaged detection zone was determined by summing the fluorescent signal from all of the pixels. The integrated signal from the sample was compared to that of negative controls. Measuring the total integrated signal is especially useful for samples containing numerous target molecules. A second approach was to count the fluorescent objects in the detection zone. A third approach was to integrate the intensity of all of the pixels contained within the fluorescent objects (as opposed to summing the intensity of all of the pixels in the image). All image analysis was performed using Image-Pro v 4.0 (Media Cybernetics, Silver Springs, Md.).

Using the IPP Image-Pro macro language, the above utilities can be automated to allow batch processing of several images at one time. In addition, the data can be manipulated with other user-defined IPP scripts. For example, objects below or above a certain size (area) or intensity can be included or excluded, which can be a useful tool for dust exclusion. Other important parameters for image analysis that determine object definition (e.g., acceptance and rejection criteria) vary by application and should be optimized accordingly.

Various aspects of the invention can be automated including linking the steps outlined above. Consider an application for analyzing liquid samples such as pharmaceutical water for injection or a clinical urine sample. Such an automated system could automatically collect samples, contact them with labeling particles, apply a selection step, obtain an image, analyze the image, and report the results. Alternatively, individual functions of the invention can be automated. For example, modules for automatically loading and unloading vessels into the imaging instrument and for automatic focusing can be incorporated into the system.

EXAMPLES

The examples below provide technical details for implementing various embodiments of the invention for use in conjunction with a range of applications and are not intended to be limiting.

Example 1. Detecting Individual Microscopic Labeling Particles without Magnification Using Electronic, Instant Film, and Unaided Visual Detection Background and Objectives:

The invention's ability to quantify low levels of target molecules rests, in part, in its ability to detect and enumerate individual microscopic target molecules in large detection areas without the use of high magnification. The goal of this example is to demonstrate that the invention can accomplish this using various means for detection: a CCD photodetector array, instant film, and simple visual detection.

The labeling particles for these experiments were latex particles that were coated with antibodies and the enzyme alkaline phosphatase. Beads placed on membranes were treated with either chemiluminogenic or chromogenic substrates of substrates of alkaline phosphatase that produce chemiluminescent or colored (purple) products, respectively. The membrane with the chemiluminescent labeling particles was imaged electronically or with instant film, and the membrane with the chromogenic labeling particles was imaged by eye.

Experimental Methods:

Particles coated with antibodies and enzyme molecules were made by adding both biotinylated alkaline phosphatase (5 µl of a 2.9 mg/ml stock; Pierce; cat. num. 29339) and biotinylated goat anti-*E. coli* 0157 antibody (5 µl of a 1.0 mg/ml stock; Kirkeguard and Perry Laboratories; cat. num. 01-95-90) to streptavidin-coated particles ($10^8$ particles; Bangs; 0.95 um, non-fluorescent; cat. num. CP01N). The volume was brought up to 100 µl with PBS. After a 30-minute incubation, the particles were washed twice. A wash consisted of spinning the particles down in a microcentrifuge at 3000 g for 5 minutes, then discarding the supernatant and resuspending the particles in PBS (100 µl). After making the dually coated particles, the beads were diluted to about 50 and 500 beads. Three replicates of each dilution as well as a no bead control were each added to PBS (50 ml) and filtered through a 0.2 µm pore nitrocellulose membrane using a vacuum pump and a plastic funnel cup (Millipore Microfil V User Guide, PF07114, Rev A 3/00). BM Purple alkaline phosphatase substrate (500 µl; Roche; cat. num. 1442074) was added to one set of filters. The other filter set had CDP-star (500 µl; NEN; cat. num. NEL-601) added to them. After a 1-hour incubation the BM purple membranes were washed in water to remove left over BM Purple, and the membranes were allowed to air dry. The CDP-star membranes were mounted in a SpotLight camera (Boston Probes; cat. num. DT10000) according to the manufacturer's instructions and exposed to ASA 2000 film (Boston Probes; cat. num. DT20000) for 2 minutes. The same filters were then observed using non-magnified large area imaging. Image-Pro Plus software, version 4.1 (Media cybernetics) was used to capture and process images from the CCD Imager.

Results.

FIG. 5 shows that the bi-functional particle, that was conjugated to a category-specific binding molecule and an enzymatic signaling moiety, can be detected using either chromogenic or chemiluminescent signal elements. The ability to see single labeling particles even with the naked eye is due to the large numbers of enzyme molecules on each labeling particle. The example demonstrates the potential for the invention to provide ultra-sensitive point-of-care tests that are simple, user-friendly, cost-effective, and non-instrumented.

Example 2. Detecting Low Numbers of Bacteria Using Non-Magnified Large Area Imaging Background and Objectives:

This example demonstrates the use of the invention to detect low numbers of bacteria rapidly using a user-friendly lateral flow assay format and non-magnified large area imaging. Lateral flow assays have been used in the diagnostic industry for over 20 years. These simple assays rely on antigen:antibody interactions to detect the presence of a specific target (or analyte). The lateral flow strips, although simple, lack the sensitivity to compete, in most diagnostic areas, with ELISA immunoassays and nucleic acid amplification methods.

In the example, various dilutions of bacterial lysates (*E. coli* O157:H7) were applied to porous membrane strips that contained a conjugate pad containing labeling particles (fluorescently dyed latex particles coated with *E. coli* O157: H7-specific antibodies), a line of capture antibodies, and a positive control line with capture antibodies that bind to labeling particles lacking target molecules. After performing the test, the capture and control lines were imaged using large area non-magnified imaging.

Experimental Methods:

The lateral flow test strips were assembled by following the directions supplied in the lateral flow kit (Millipore; High Flow Mid Range Assembly Kit, cat. no. HFMI-DAK015). In short, wicking, conjugate, and sample pads were placed onto a lateral flow membrane, which was attached to an adhesive support card. Antibody lines were made by applying two lines of capture antibodies across the membrane strips: one for *E. coli* O157:H7 (the capture line; 10 µl of a 1 mg/ml solution per 8 cm line, BioTrace affinity purified; Kirkegaard & Perry Laboratories, cat. no. 01-95-90) and one for a positive control (the control line; 10 µl of a 1 mg/ml solution per 8 cm long line, Jackson Immuno Research Laboratories, Inc.; biotin anti-goat IgG, cat. no. 115-165-146) onto the membrane (5-10 mm from wicking pad). The lines were allowed to dry (at least 15 min) before use. Streptavidin labeled fluorescent beads (Bangs Laboratories Inc., cat. no. CP01F-5121) were labeled with biotin anti-*E. coli* O157:H7 antibody (BioTrace affinity purified; Kirkegaard & Perry Laboratories, cat. no. 01-95-90) by combining the beads (10 µl of $1.23 \times 10^{11}$/ml, antibody (10 µl of 1.0 µg/ml stock) and PBS (80 µl)) and mixing (1.5 hours/room temp). The beads were then centrifuged (5000 g, 10 min) and resuspended in PBS-B (100 µl). The anti-*E. coli* coated fluorescent beads (2 µl) were added to the conjugate pad of each strip. A stock of formaldehyde fixed *E. coli* O157:H7 cells (Strain DEC 3B, Dr. Tom Whittam, Pennsylvania State University, $10^9$ cells/ml) were serially diluted using PBS. The serial dilutions (100 µl) were then added to a lysing solution (100 µl of 200 mM NaOH/1% SDS) and allowed to sit for 3 min. PBS-B (800 µl) was added to neutralize the lysis solution. Test samples (100 µl of the lysed *E. coli* dilution) were combined with PBS-TB (50 µl) and added to the sample pad of the test strip. The sample moved through the sample pad to the conjugate pad, where the fluorescent beads were integrated into the sample flow. The sample then proceeded into the test membrane, through the capture and control line and finally into the wicking pad. After performing the assay, (~15 minutes). The membranes were then imaged by placing the strips on a CCD-based imager (described in Step 5 of Detailed description section and shown in FIG. 3) so that the bacteria were facing the illumination source and CCD chip. The strips were imaging using non-magnified large area imaging. The images were analyzed using Image-Pro software.

Results:

FIG. 6 shows the results of the lateral flow test for detecting bacteria. The figure shows images of the capture and control lines from representative strips. The leftmost strip shows the results when a negative control sample containing no bacteria was analyzed. When the negative control is compared to the middle and right strip, containing 1000 and 10,000 *E. coli* respectively, it is apparent that as the number of bacteria increases, the signal from the capture line also increased. The bottom bar graph shows the signal from the average of five replicates in relation to the number of *E. coli* added. The error bars represent a three standard deviation error between the replicate signals. The data shows a detection limit of 1000 bacteria, which is 10-100 times more sensitive than commercial tests on the market.

Example 3. Ultra-Sensitive Lateral Flow Test for Detecting Low Levels of Protein Using Non-Magnified Large Area Imaging Background and Objectives:

There is an unmet need for more sensitive rapid tests for protein markers. This example demonstrates the use of the invention to detect low levels of protein (IL-2) rapidly with the user-friendly lateral flow assay format, fluorescent labeling particles, and non-magnified large area imaging. Detecting and quantifying low levels of target proteins in a sample is becoming more important as new markers for human disease (e.g., cancer and cardiovascular disease) are discovered.

Experimental Methods:

The lateral flow test strips were assembled as in Example 2.

Antibodies were applied to membranes to make an IL-2 specific capture line (Pharmingen, cat. no. 554424) and a negative control line (Jackson Immuno Research Laboratories, Inc.; biotin anti-mouse IgG, cat. no. 115-165-146) onto the membrane at a distance of 5 to 10 mm from the wicking pad. The lines were allowed to dry (at least 15 min) before use. Streptavidin labeled fluorescent beads (Bangs Laboratories Inc., cat. no. CP01F-5121) were labeled with a biotin anti-IL-2 antibody (Pharmingen; cat. no. 554426) by combining the beads (10 µl of $1.23 \times 10^{11}$/ml, antibody (10 µl of 1.0 µg/ml stock)) and PBS (80 µl) and mixing (1.5 hours/room temp). The beads were then centrifuged (5000 g, 10 min) and resuspended in PBS-B (100 µl). The anti-IL-2 antibody-coated fluorescent beads (2 µl) were added to the conjugate pad of each strip. A stock solution IL-2 (Pharmingen; Recombinant Mouce IL-2, cat. no. 550069) was serially diluted using PBS-B. Test samples (100 µl of an IL-2 dilution) were combined with PBS-TB (50 µl) and added to the sample pad of the test strip. After performing the test (~15 minutes) the strips were imaged as in Example 2. The images were analyzed using Image-Pro software.

Results:

FIG. 7 shows the results of the lateral flow test for IL-2. In the figure, capture and control line images are seen from representative test strips. The leftmost strip shows the negative control (no IL-2 added). When the negative control is compared to the middle and right strip, samples containing IL-2 at 2 pg/ml and 20 pg/ml, respectively, it is apparent that as the amount of IL-2 increased, the signal from the capture line also increased. The bottom bar graph shows the signal from the average of five replicates in relation to the amount of IL-2 added. The error bars represent a three standard deviation error between the replicate signals. The data shown indicates that the test detects IL-2 at a level of 2 pg/ml, which is 10-100 times more sensitive than commercial tests on the market.

Example 4. Ultra-Sensitive Lateral Flow Test for Detecting Low Levels of Protein in Serum Using Non-Magnified Large Area Imaging Background and Objectives:

Detecting target molecules in the context of complex samples is important for many applications. This example demonstrates the use of the invention to detect low levels of IL-2 in serum rapidly with a user-friendly lateral flow format and non-magnified large area imaging. In the experiment described below, IL-2 in serum was detected using fluorescent labeling particles.

Experimental Methods:

The lateral flow test strips were assembled as in Example 3.

Antibodies were applied to membranes to make an IL-2 specific capture line (Pharmingen, monoclonal anti-IL-2, cat. no. 554424) and control line (Jackson Immuno Research Laboratories, Inc.; biotin anti-mouse IgG, cat. no. 115-165-146) at a distance of 5 to 10 mm from the wicking pad. The lines were allowed to dry (at least 15 min) before use. Streptavidin labeled fluorescent beads (Bangs Laboratories Inc., cat. no. CP01F-5121) were labeled with biotin anti-IL-2 antibody (Pharmingen; cat. no. 554426) by combining the beads (10 µl of $1.23 \times 10^{11}$/ml stock), antibody (10 µl of 1.0 µg/ml stock) and PBS (80 µl) and mixing (1.5 hours at room temp). The beads were then centrifuged (5000 g, 10 min) and resuspended in PBS-B (100 µl). The anti-IL-2 coated fluorescent beads (2 µl) were added to the conjugate pad of each strip. A stock solution of IL-2 (Pharmingen; recombinant mouse IL-2, cat. no. 550069) was serially diluted using serum (Fitzgerald Laboratories; Normal goat serum, cat. no. 88-NG22). Test samples (100 µl of an IL-2 dilution) were combined with PBS-TB (50 µl) and added to the sample pad of the test strip. After performing the test (~15 minutes) the strips were imaged as in Example 2. The images were analyzed using Image-Pro software.

Results:

FIG. 8 shows the results of the lateral flow test for IL-2 in serum. In the figure, capture and control line images are seen from representative test strips. The leftmost strip shows the negative control. When the negative control is compared to the middle (20 pg/ml) and right (200 pg/ml) strips, it is apparent that as the amount of IL-2 increased, the signal from the capture line also increased. The bottom bar graph shows the signal from the average of five replicates in relation to the amount of IL-2 added. The error bars represent a three standard deviation error between the replicate signals. The data shows that the invention can detect IL-2 at 20 pg/ml of serum demonstrating that the assay detects very low levels of a target protein even in a complex sample.

Example 5. Ultra-Sensitive Lateral Flow Test for Multiplex Detection of a Protein and a Bacterium Using Non-Magnified Large Area Imaging Background and Objectives:

The need to test for the presence of a panel of target molecules is common. Examples are tests that survey samples for the various microbes that can cause sexually transmitted disease, panels of drugs-of-abuse, and sets of biowarfare agents. This example demonstrates the use of the invention to detect low levels of E. coli and IL-2 rapidly and simultaneously, using a user-friendly lateral flow assay format, fluorescent labeling particles, and non-magnified large area imaging.

Experimental Methods:

The lateral flow test strips were assembled as in Example 2. Antibodies were applied to membranes to make E. coli O157:H7 (BioTrace affinity purified; Kirkegaard & Perry Laboratories, cat. no. 01-95-90) and IL-2 (Pharmingen, cat. no. 554424) capture lines as well as a control line (Jackson Immuno Research Laboratories, Inc.; biotin anti-goat IgG, cat. no. 115-165-146) at a distance of 5 to 10 mm from the wicking pad. The lines were allowed to dry (at least 15 min) before use. Fluorescent beads for both IL-2 (refer to Example 3 for making IL-2 beads) and E. coli (refer to Example 2 for making E. coli beads) (2 µl of each) were added to the conjugate pad of each strip. Test samples (100 µl of an E. coli or IL-2 dilutions) were combined with PBS-TB (50 µl) and added to the sample pad of the test strip. After performing the test (~15 minutes), the strips were imaged as in Example 2. The images were analyzed using Image-Pro software.

Results:

FIG. 9 shows the results of a multiplexed lateral flow test using non-magnified large area imaging. The figure shows images of the capture and control lines from test strips onto which were applied samples containing (from left to right) both E. coli and IL-2, E. coli alone, IL-2 alone, and neither E. coli nor IL-2. This figure demonstrates that the lateral flow test can detect multiple target molecules in the same assay.

Example 6. Ultra Sensitive Lateral Flow Test for Detecting Low Levels of Virus Using Non-Magnified Large Area Imaging Objective:

This example demonstrates how the invention can be used to detect low numbers of viral particles rapidly with a user-friendly lateral flow format and non-magnified large area imaging. In the experiment described below samples containing dilutions of lysed Influenza virus are detected using fluorescent labeling particles and large area imaging.

Experimental Methods:

The lateral flow test strips are assembled as in Example 2. Antibody lines are made by applying both an Influenza A specific capture line (QED, cat. no. 1302) and control line (Jackson Immuno Research Laboratories, Inc.; biotin anti-mouse IgG, cat. no. 115-165-146) onto the membrane at 5 to 10 mm from the wicking pad. The lines are allowed to dry (at least 15 min) before use. Streptavidin labeled fluorescent beads (Bangs Laboratories Inc.; cat. no. CP01F-5121) are labeled with biotin anti-Influenza A antibody (Virostat; cat. no. 1307) by combining the beads (10 µl of $1.23 \times 10^{11}$/ml stock), antibody (10 µl of 1.0 µg/ml stock) and PBS (80 µl) and mixing (1.5 hours/room temp). The beads are then centrifuged (5000 g, 10 min) and resuspended in PBS-B (100 µl). The anti-Influenza A coated fluorescent beads (2 µl) are added to the conjugate pad of each strip. A stock solution of purified Influenza A (Advanced Biotechnologies Inc: Influenza A/PR/8/34 (H1N1), cat. no. 10-210-000) is lysed (Aoyagi, K., C. Ohue, et al. (1999). *J Clin Microbiol* 37(6): 1802-8) and then serially diluted using PBS-B. Test samples (100 µl of an IL-2 dilution) are combined with PBS-TB (50 µl) and added to the sample pad of the test strip. After performing the test (~15 minutes), the strips are imaged as in Example 2. The images are analyzed using Image-Pro software.

Example 7. Ultra-Sensitive Chemiluminescent Lateral Flow Test for Detecting Low Levels of Protein Using Instant Film Objective:

There is an unmet need for ultra-sensitive point-of-care tests. Ideally, these tests are portable and do not require expensive instrumentation. This example demonstrates detection of low levels of the cytokine protein IL-2 using cost-effective instant film detection, high intensity chemiluminescent labeling particles, and a user-friendly lateral flow format.

Experimental Methods:

The lateral flow test strips were assembled as in Example 2. Antibody lines were made by applying both an IL-2 specific capture line (Pharmingen; cat. no. 554424) and control line (Jackson Immuno Research Laboratories, Inc.; biotin anti-mouse IgG, cat. no. 115-165-146) onto pieces of membrane (5-10 mm from the wicking pad). The lines were allowed to dry (at least 15 min) before use. Streptavidin labeled beads (Bangs Laboratories Inc.; cat. no. CP01F-5121) were labeled with biotin anti-IL-2 antibody (Pharmingen; cat. no. 554426) and biotin alkaline phosphatase (Pierce; cat. no. 29339) by combining the beads (10 µl of $1.23 \times 10^{11}$/ml), antibody (10 µl of 1.0 µg/ml stock), biotin labeled AP (10 µl of an mg/ml stock) and PBS (70 µl) and mixing (1.5 hours/room temp). The beads were then centrifuged (5000 g, 10 min) and resuspended in PBS-B (100 µl). The anti-IL-2 coated AP beads (2 µl) were added to the conjugate pad of each strip. A stock solution of IL-2 (Pharmingen; recombinant mouse IL-2, cat. no. 550069) was serially diluted using serum PBS. Test samples (100 µl of an IL-2 dilution) were combined with PBS-TB (50 µl) and added to the sample pad of the test strip. After performing the test (~15 minutes), the strips were soaked with a chemiluminescent detection reagent (Pierce; Lumiphos, cat. no. 34150). After a short incubation (~5 min), the strips were imaged using instant film (VWR; Polaroid Polapan Type 667, cat. no. GRP0617538). The instant film was then scanned (Hewlett Packard; HP scanjet 7400c, cat. no. C7713A).

Results:

FIG. 10 shows the results the lateral flow test using chemiluminescent labeling particles and instant film detection. Capture and control lines from representative test strips are shown. Comparing the strips onto which were applied samples containing IL-2 (from left to right: 0, 20, 200, and 2000 pg/ml) indicates that as the amount of IL-2 increased, the signal from the capture line also increased. The data show that the invention can detect IL-2 at concentrations as low as 20 pg/ml using instant film. Thus this test is ultra-sensitive, rapid, easy to perform, and very inexpensive.

Variations:

Other films (including normal photographic film and x-ray film) could be used. Exposed film could be digitized using inexpensive commercial scanners yielding images that could be analyzed using image analysis software. Other chemiluminescent reagents, such as horseradish peroxidase, could be used rather than alkaline phosphatase. Numerous other chemiluminescent substrates could be used including CDP-star (Applied Biosystems; cat. no. T2307) or Signal-Signal West Pico (Pierce; cat. no. 34080). Colorimetric assays could also be developed using a chromogenic substrate such as BM purple (Roche; cat. no. 1442074).

Example 8. Ultra-Sensitive, Non-Membrane Based Lateral Flow Assay for Detecting Low Levels of Protein Using Non-Magnified Large Area Imaging Objective:

This example describes rapid and ultra-sensitive detection of a protein with an embodiment of the invention that uses porous "capture threads" rather than traditional lateral flow strips. The format minimizes the expanse of membrane that a particle must negotiate on its route through the detection area. There are two major advantages of the capture thread format, both of which increase the sensitivity of tests: (1) larger sample volumes are efficiently processed and (2) larger labeling particles, which have even more intense signals, can be used.

FIG. 11 shows the construction of the device used in this example. The sample is loaded into the sample zone where it flows laterally into the conjugate pad. The sample, drawn by the absorbent pad at the distal end of the apparatus, solubilizes and mobilizes the detection beads, which flow through the assay threads. In the experiment described below, dilutions of IL-2 were applied to slides containing a conjugate pad containing fluorescent labeling particles specific for IL-2, a capture threads for binding IL-2, and a positive control thread.

Experimental Methods:

The tests were assembled on glass slides as follows (see FIG. 11). Antibody stripes were applied to two pieces (3 mm×25 mm) of a lateral flow membrane (Millipore; Hi-Flow Plus, cat. no. HF13502). The capture thread stripe contained a capture antibody (Pharmingen; monoclonal anti-IL-2, cat. no. 554424, 10 µl of a 1 mg/ml solution per 8 cm) and control antibody (Jackson Immuno Research Laboratories, Inc.; biotin anti-mouse IgG, cat. no. 115-165-146, 10 µl of a 1 mg/ml solution per 8 cm). After drying (15 min), the threads were placed 10 mm (control thread) and 13 mm (capture thread) from the end of a glass slide (VWR; cat. no. 48300-025). A piece of glass fiber mesh (Millipore; glass fiber conjugate pad, part of cat. no. HFMIDAK015) was cut (3 mm×25 mm) and placed 20 mm from the end of the glass slide. A piece of absorbent paper (50 mm×25 mm) was placed at the end of the slide. A second glass slide was placed on top of the capture threads, glass fiber and absorbent paper so that one end of the glass slide was directly on the piece of glass fiber, with the other end overlapping onto the absorbent paper. Streptavidin labeled fluorescent beads (Bangs Laboratories Inc.; cat. no. CP01F-5121) were coated with a biotin anti-IL-2 antibody (Pharmingen; cat. no. 554426) by combining the beads (10 µl of $1.23 \times 10^{11}$/ml), antibody (10 µl of 1.0 µg/ml stock) and PBS (80 µl) and mixing (1.5 hours/room temp) with rotation. The beads were then centrifuged (5000 g, 10 min) and resuspended in PBS-B (100 µl). The anti-IL-2 coated fluorescent beads (2 µl) were added to the conjugate pad of each assay slide. A stock solution of IL-2 (Pharmingen; Recombinant Mouse IL-2, cat. no. 550069) was serially diluted (for final concentrations of 0, 20, 200 pg/ml) using PBS-B. Test samples (1 ml of 0, 20 and 200 pg/ml dilutions) were added to the sample loading zone of the test slide. After performing the test (~15 minutes), the strips were imaged as in Example 2. The images were analyzed using Image-Pro software.

Results:

FIG. 12 shows the results of the test. The figure shows images of the capture and control threads from tests applied to samples containing IL-2 (0, 20, and 200 pg/ml). The results indicate that the test can detect IL-2 at 20 pg/ml. Furthermore, the concentration dependent speckled appearance of the capture threads suggests that individual labeling particles are being imaged.

The test used a volume that is 5 to 10 times the volume that is typically loaded on traditional lateral flow devices, yet the assays were completed in about the same time as when traditional "low volume" lateral flow tests were performed in the previous examples. By increasing the length of the capture threads even larger volumes could be analyzed. The ability to increase sensitivity by elongated the threads is a byproduct of the invention's ability to detect individual labeling particles. When detecting individual labeling particles, increasing the length of the capture line or thread and increasing the sample volume produces more signal without an increase in background (recall that the relevant background intensity can be measured in a region of comparable size to that containing a positive signal). In contrast, tests that measure integrated signal intensity do not improve by increasing the size of the capture line because the background increases in proportion to the signal.

Example 9. Sensitive Detection of Protein Molecules Using Non-Magnified Large Area Imaging and Solid-Phase Capture Immunoassay Overview.

In this example, non-magnified large area imaging was used to detect IL-2 protein target-entities. IL-2 molecules were captured by antibodies that had been adsorbed to the surfaces of antibody-coated microtiter dish wells. Fluorescent particles, coated with a different anti-IL-2 antibody, were then bound to the surface-immobilized IL-2 molecules. Non-magnified large area imaging was used to detect the individual particle:IL-2 complexes.

Experimental Design.

A 96 well plate (optically clear plastic bottom; Greiner America, Inc.; cat. num. 55896) was coated with biotinylated BSA (Sigma; cat. num. A-8549; 50 µl of 200 µg/ml biotinylated BSA in. 2M sodium bicarbonate, pH 10) The plate was incubated overnight at room temperature. The next day the wells were "washed" by adding PBS (200 µl) to each well and then aspirated. The biotinylated BSA-coated wells were then further coated with streptavidin/PBS solution (Jackson Labs; cat. num. 016-000-084; 50 µl of a 100 µg/ml solution) and incubated overnight at room temperature. The next day, the wells were washed as stated above. The biotin: streptavidin coated wells were then coated with biotinylated Rat anti-mouse IL-2 antibody (50 µl of a 0.5 mg/ml solution; Pharmingen; cat. num. 554426). The wells were covered and allowed to shake at room temperature for 3.5 hours. After incubation the wells were washed three times with PBS-B (Sigma; cat. num. A-7638)/0.05% triton X 100 (Sigma/X-100). The wells were then blocked with Block Aid (150 µl; Molecular Probes; cat. num. B-10710) followed by a 40-minute incubation at room temperature. The Block Aid was decanted and ELISA diluent (50 µl; Pharmingen; cat. num. 2728KD) was added to each well. An IL-2 standard (150 pg/ml; Pharmingen; cat. num. 27316E) was serially diluted in ten fold increments with standard diluent (Pharmingen; cat. num. 2708KD), and 50 µl of each dilution was added to separate wells. The plate was allowed to incubate at room temperature for two hours. After incubation antibody coated red fluorescent particles ($10^6$; Molecular probes; 1 µm; sulfate; 580/605 nm; cat. num. F-8851) which were coated by passive adsorption with a rat anti-mouse IL-2 antibody (Pharmingen; cat. num. 18161D) were added to each well. To passively adsorb antibodies to the surface sulfate groups of the beads, particles (62.5 µl; 2% solids; Molecular Probes Cat. No. F8851, 1 µm, red fluorescent (580/605)) were washed by repeatedly (3 repetitions) by centrifugation (5 min; 10,200×g; Eppendorf Centrifuge Model 5417C, Eppendorf Swinging Bucket Rotor Model A-12-11) and resuspension of the particle pellet (1 ml PBS/0.15 M NaCl). The particle pellet was resuspended in PBS (125 µl, for a concentration of 1% solids) followed by drop wise addition of purified antibody (1.25 nmol for a ratio of 1 nmol antibody/mg particles) with vortexing. The suspension was incubated with rotation, for 2 hours at 25° C. followed by overnight incubation at 4° C. Particles were washed (3 repetitions as above, but with resuspension after the centrifugations in PBS-TB), resuspended in PBS-TB (200 µl), and incubated (30 minutes, 25° C.) with rotation. Particles were washed twice as above and resuspended in PBS-TB (125 µl for a concentration of 1% solids). After the addition of the passively coated beads ($10^7$), the wells were allowed to incubate at room temperature for one hour. The plates were washed six times with 1×ELISA wash solution (200 µl; from a dilution of a 20× stock; Pharmingen; cat. num. 2605KC) and then once with water. Fluorescence was detected by imaging on the GPS Imager with Texas Red optical filter set (Chroma excitation 560/55 nm, emission 645/75 nm) for the red fluorescent particles. Image-Pro Plus software, version 4.1 (Media cybernetics) was used to capture and process images from a CCD Imager as in Example 2. Positive signals detected on the Imager were confirmed to be particles by using an Axioplan II fluorescent microscope (Carl, Zeiss Inc., Thornwood, N.Y.) equipped with the same filter sets.

Results.

FIG. 13 shows IL-2 detection in a solid phase capture assay. As the concentration of IL-2 decreases, the number of anti-IL-2 antibody coated fluorescent particles (seen as white spots) also decreases. When compared to the no IL-2 negative control, the sensitivity of the assay (defined as two standard deviations above the average negative control) is about 1.5 pg/ml. This result is comparable to ELISA tests for IL-2.

Example 10. Sensitive Detection of Protein Molecules Using Non-Magnified Large Area Imaging and Liquid-Phase Capture Overview.

In this example, as in the previous one, non-magnified large area imaging was used to detect IL-2 protein target-entities. Here, however, IL-2 molecules were bound to pairs of antibody-coated particles in the liquid phase. As in earlier examples, one particle is fluorescent and one particle is magnetic. Particle:analyte complexes are deposited in a planar detection zone using magnetic force. These complexes are imaged using non-magnified large area imaging as before.

Experimental Procedure.

Anti-IL-2 magnetic particles were made by coupling magnetic particles with active tosyl-groups to monoclonal antibodies raised against IL-2 (Rat anti-IL-2, Pharmingen; cat. num. 18161D). Magnetic particles (30 mg/ml; 100 µl; Dynal, Oslo, Norway, Dynaparticles M-280 Tosylactivated Cat. No. 140.03) were washed in PB (three wash repetitions, 1 ml each) in a microcentrifuge tube (1.5 ml) using a magnetic separation of the particles followed by removal of the supernatant (all magnetic separations in this example, except where noted, were carried out using a device from Polysciences Inc.; cat. no. 8MB4111S). Particles were resuspended in PB (70 µl). Monoclonal antibodies against IL-2 (60 µg; Pharmingen; cat. num. 18161D) were combined with magnetic particles (70 µl) in a microcentrifuge tube (1.5 ml) and vortexed briefly. The reaction was incubated at 37° C. for 20 minutes using rotation (about 30 rpm unless otherwise noted). After 20 minutes BSA (IgG free) was added to a final concentration of 0.1% and incubated overnight at 37° C. with rotation. The magnetic particles were washed twice (1 ml each; using magnetic separation) with PBS-B. The magnetic particles were resuspended in buffer (0.2M Tris pH 8.5 supplemented with 0.1% (w/v) BSA (IgG free)) and incubated for 4 hours at 37° C. with rotation. Finally, the magnetic particles were washed twice (in PBS-B using magnetic separation) and resuspended (the final concentration was 1% solids in PBS-B). After making the magnetic beads, an IL-2 standard (150 pg/ml; Pharmingen; cat. num. 27316E) was serially diluted in ten fold increments. In separate 1.5 ml tubes, 20 µl of each dilution was combined with magnetic particles coated with rat anti-IL-2 antibody and red fluorescent particles ($10^8$ particles; Molecular Probes; 1 µm; sulfate; 580/605 nm; cat. num. F-8851) which were coated (see Example 9 for passive adsorption coating) with biotin labeled rat anti-mouse IL-2 (Pharmingen; cat. num. 554426). The particle:IL-2 suspension (120 µl) was mixed with Block Aid (60 µl; Molecular Probes; cat. num. B-10710) and sonicated for 30 seconds (setting 8; 550 Sonic Dismembrator; Misonix). After sonication, additional Block Aid (60 µl) was added and the tubes were mixed. The tubes were then incubated with mixing for one hour at room temp. After incubation the tubes were washed three times in PBS-TB. A wash consisted of a magnetic separation to draw the magnetic particle:IL-2:fluorescent particle sandwich to one side of the tube followed by an aspiration to remove the supernatant. After each wash, PBS-TB (50 µl) was added. Aliquots were added to an optically clear plastic bottomed plate (Greiner America, Inc.; cat. num. 655896). Fluorescence was detected by imaging on a CCD Imager with Texas Red optical filter set (Chroma/excitation 560/55 nm, emission 645/75 nm) for the red fluorescent particles. Image-Pro Plus software, version 4.1 (Media cybernetics) was used to capture and process images from the CCD Imager. Positive signals detected by CCD imaging were confirmed to be particles by using an Axioplan II fluorescent microscope (Carl, Zeiss Inc., Thornwood, N.Y.) equipped with the same filter sets.

Results.

FIG. 14 shows IL-2 detection on a solid phase assay. As the concentration of IL-2 decreases, the number of anti-IL-2 antibody coated fluorescent particles (seen as white spots) also decreases. When compared to the no IL-2 negative control, the sensitivity of the assay (defined as two standard deviations above the average negative control) is about 1.5 pg/ml.

Example 11. Immunoassay for Detecting Multiple Human Cytokines Using Non-Magnified Large Area Imaging Cytokines are essential mediators of cell-cell communication and are central to orchestrating the cellular dynamics underlying the immune response. Complex combinations and low concentrations of these proteins are characteristic of pathogenic microenvironments. Thus, methods for sensitive multiplexed detection of cytokines are needed for research and clinical analysis. In this example, the invention is used to construct such a test. In the example, individual protein molecules are detected without using magnification. Antibodies attached to a microtiter well are used to capture the protein molecules which are then labeled by binding to high intensity fluorescent particles as in Example 9.

FIG. 15 depicts the scheme of the assay which tests for four cytokines: granulocyte macrophage colony-stimulating factor (GM-CSF), interleukin-2 (IL-2), interleukin-4 (IL-4), and tumor necrosis factor-α (TNF-α). The test developed in this example is formally similar to the previous test (multiplexed viruses) except for the following significant distinction. Because protein molecules (as opposed to viruses) are the targets in this assay, the capture antibodies (linked to the well surface) and detection antibodies (linked to fluorescent particles) must recognize non-overlapping epitopes on the targets.

Coating Fluorescent Particles and Wells with Anti-Cytokine Antibodies.

Standard anti-cytokine antibody pairs (with non-overlapping epitopes) are obtained from commercial sources as detailed previously (Carson, R. T., et al., J Immunol Methods 227: 41-52, 1999).

Antibodies are bound to microtiter dish wells in four adjacent distinct spots per well (1 spot per antibody) by passive absorption. Each anti-viral antibody is spotted (1 µl; 1 µg/µl) in a well of a 96-well microtiter plate (Greiner America; cat. num. 55896) and incubated for 2 hrs at room temperature in a humidified chamber (Boekel Slide Moat; model 240000). Wells are then washed and blocked as in Example 9 (Note that alternatively, an equimolar mixture of the antibodies can be bound as a homogenous mixture to the wells in this example).

Color-coded cytokine-specific fluorescent particles are made by coating fluorescently dyed polystyrene particles with distinct emission spectra with the anti-cytokine detection antibodies (detailed in Carson et al, 1999, supra) as described in the previous example. Fluorescent particles are coded as follows: GM-CSF-specific particles: Yellow-Green; IL-2-specific particles: Orange; IL-4-specific particles: Crimson; and TNF-α-specific particles: Infrared. The 4 types of antibody-coated particles are mixed and prepared as described in the previous example. As in the previous example, it is also possible to use the same type of fluorescent particle for each virus.

Standard Curves.

Standard curves are constructed that relate the concentration of the cytokines to the integrated assay signal. Samples (200 µl; in PBS-TB; run in triplicate) containing 10 fold dilutions of individual cytokines at concentrations ranging from 10 pg/ml to 10 µg/ml are added to individual microtiter dish wells containing spotted capture antibodies. After 30 minutes, the wells are washed with PBS-TB (200 µl; 4×). The combined cytokine-specific particles (200 µl) are added to the wells and spun briefly in a centrifuge (Beckman Allegra 6; GH-3.8 rotor; 1200 g) so as to coat the bottom surface of the well with the particles. After incubating the particles for 10 minutes at room temperature, unbound particles are removed by washing (3 washes of 200 µl PBS-TB; each wash solution is agitated by re-pipetting 5 times). Next, the number, color, and cumulative intensity of the particles bound to each spot is determined. The wells are then imaged and analyzed using a CCD imager as in Example 2 except that multiple images are acquired using the appropriate filter sets (yellow green: excitation Chroma HQ480/40x and emission Chroma HQ535/50m; orange: excitation Chroma HQ535/50X and emission Chroma HG610/75m; crimson: excitation Chroma HQ560/55x and emission Chroma HQ645/75m; and infrared: excitation Chroma HQ710/75x and emission Chroma HQ810/90m). Viruses are identified by the spots to which bound particles adhere. Additional diagnostic robustness is provided by the fact that only particles of the expected color adhere to a particular spot if the assay is successful.

Detecting Cytokines in an Uncharacterized Sample.

A sample (200 µl) containing, or potentially containing, cytokines GM-CSF, IL-2, IL-4, and/or TNF-α is added to a microtiter dish well containing spotted capture antibodies. The sample is processed and analyzed as described above. The concentration of the cytokines is estimated by using interpolation to compare the quantified signal corresponding to the four cytokine-specific capture antibody spots to the established standard curves.

Example 12. Competitive Immunoassay for Total (Bound Plus Free) Cytokine IL-2 Using Non-Magnified Large Area Imaging Competitive immunoassays are used when a target-entity does not have non-overlapping category-specific binding sites (e.g., epitopes). This is generally the case for small molecule analytes such as drugs of abuse (e.g., cocaine), chemical pollutants (e.g., PCBs), or hormones (e.g., Triiodo-thyronine). Competitive immunoassays are also useful when only one epitope on a target molecule is accessible to antibodies, for example, when a small protein hormone or cytokine is bound to, and largely engulfed by, a larger binding protein or receptor.

Competitive immunoassays measure the capture of an analogue of the target-entity, which, in contrast to the target-entities, does have two distinct binding sites and therefore is measurable using basic immunoassay procedures. Target-entities in the sample can compete with the analogue for capture sites. Therefore, the degree of capture of the analogue is a function of the concentration of the target-entity in the sample.

This example describes an assay constructed using the invention that tests for total cytokine IL-2 (i.e., bound IL-2 plus free IL-2) using a competitive immunoassay format. A schematic of the competitive immunoassay is displayed in FIG. 16.

Competitive Immunoassay for IL-2.

The competitive immunoassay for IL-2 is carried out using a commercial kit (Chemicon; cat. #CYT111) and following the manufacturer's recommended protocols with the modifications noted below. The kit is representative of a common variety of immunoassay that causes a solution in a microtiter dish to become colored.

The color intensity indicates the amount of analyte in the sample and is a result of the cumulative action of bound enzyme:antibody conjugates. The test constructed using the invention differs from the classical competitive immunoassay. First, individual targets—in this case the IL-2:biotin conjugate—are imaged by binding to a fluorescent streptavidin-coated particle. Second, bound fluorescent particles are imaged through optically clear well bottoms rather than spectrophotometric determination of a color change from above the well. Although the fluorescent particles are microscopic (~1 µm), imaging is carried out without magnification.

Because a flat, optically clear well-bottom is required imaging individual binding events, an appropriate microtiter plate is substituted for the secondary antibody-coated plate supplied in the commercial kit. A 96-well microtiter plate with an optically clear bottom (Greiner Labs; catalogue number 665097) is coated with mouse anti-interleukin 2 antibody (Chemicon; #MAB1018) as described previously (Coligan et al., 1994, section 6.22.1, supra).

In the commercial kit, a streptavidin:alkaline phosphatase conjugate is used to detect the bound IL-2:biotin conjugate via the reaction of chromogenic alkaline phosphate substrates. In this example, streptavidin-coated fluorescent particles (Molecular Probes; cat #8775; 1 µm diameter; fluorescent red) are substituted for the streptavidin:alkaline phosphatase conjugate.

Competitive immunoassays for both standards (included in the commercial kit) and unknowns are processed as recommended by the commercial kit manufacturer with the following exceptions. Samples are processed in plates with optically clear well-bottoms (see above). At the point when the streptavidin:alkaline phosphatase conjugate would be added according to manufacturer's protocol, streptavidin-coated fluorescent particles are added (100 µl; $10^7$ particles/ml in PBS-T). The assays are then processed and imaged as described in Example 11. Optical filters for excitation (Chroma HQ560/55x) and emission (Chroma HQ645/75m) used to image the wells are chosen in concordance with the optical properties of the fluorescent particles (excitation/emission: 580/605).

Example 13. Sensitive Detection of Nucleic Acid Molecules Using a Dipstick Format and Non-Magnified Large Area Imaging Overview.

In this example, non-magnified large area imaging was used to detect biotinylated DNA that was specifically bound to avidin-labeled fluorescent beads. A simple but sensitive dipstick assay was used to achieve rapid binding of the fluorescent beads to biotinylated lambda DNA that was bound to a nylon membrane. The assay format may have potential in point-of-care genetic testing.

Experimental Design.

Biotinylated lambda DNA was spotted on a nylon membrane (0.2 µm pore; Pall Biodyne A; cat. num. 28152-409) in ten fold dilutions (ranging from 1 µg to 10 pg). On the same filter, a negative control sample (1 µg of non-biotinylated lambda DNA) was deposited. The DNA was crosslinked to the membranes using a U.V. crosslinker (Stratagene). The membranes were blocked by saturating the membranes with BB buffer (50 µl) for 30 min at room temperature. The membranes were then allowed to dry. After blocking, one end of the membrane was dipped into a solution containing $10^{12}$ avidin-coated Texas red fluorescent beads (0.45 µm; Spherotech; cat. num. VFP-0562-5) in a 1.5 ml tube. The solution traveled up the membrane by capillary action until it reached its peak height, about three quarters of the length of the strip. The spots of DNA were placed on the strip so that they would be well below the peak height of the solution. The membrane was then washed in PBS-TB (35 ml) for 10 minutes at room temperature. Fluorescence was detected by imaging using a CCD imager in conjunction with a Texas Red optical filter set (Chroma; excitation 560/55 nm, emission 645/75 nm) that was appropriate for detection the red fluorescent beads. Image Pro Plus software, version 4.1 (Media cybernetics) was used to capture and process images from the CCD Imager. Positive signals detected on the Imager were confirmed to be beads by using an Axioplan II fluorescent microscope (Carl, Zeiss Inc., Thornwood, N.Y.) equipped with the same filter sets.
Results.

FIG. 17 shows the detection of DNA molecules down to a level of about $10^6$ molecules in a spot using non-magnified large area imaging. The spot containing 100 pg of biotinylated lambda DNA has a significantly stronger signal than does the negative control containing 1 μg of non-biotinylated lambda DNA. The expected dose response can be seen in the figure. As The DNA in a spot increases, so does the number of fluorescent beads (seen as white spots in the figure).
Variations.

An important variation of the test is to use specific hybridization probes as the category binding molecule. Such probes could be directly or indirectly labeled as described in various other examples. Similarly, tests for measuring expression of particular categories of RNA molecules could be developed in this assay format.

Example 14. A Test for Genotyping Single Nucleotide Polymorphisms

Detecting single nucleotide polymorphisms (SNPs) is a critical modern genetics application—in both applied (e.g., medical and agricultural) and basic biological fields. This example describes the application of the invention for creating a novel test that determines a patient's genotype at the site of a common mutation causing sickle cell anemia using a homogenous, non-amplified format. The test uses an oligonucleotide ligation assay in which one of the probes is labeled with a magnetic particle and one with fluorescent particles
Labeled probes for oligonucleotide ligation assay.

The oligonucleotide ligation assay for genotyping SNPs uses two oligonucleotide moieties are used in the assay: a "constant" oligonucleotide and an "allele specific" oligonucleotide. The constant oligonucleotide is labeled with a magnetic particle at the 3' end. The allele specific oligonucleotide is labeled with fluorescent particle at its 5' end (different color particles are used for different alleles). The constant oligonucleotide is designed to hybridize to one strand at the locus so that the 5' end of the oligonucleotide is adjacent to the polymorphic nucleotide. The "allele specific" oligonucleotide hybridizes to the locus so that its 3' terminal nucleotide, which corresponds to the single nucleotide polymorphism, abuts the 5' terminal nucleotide of the constant oligonucleotide when both are hybridized to the complementary nucleic acid strand.

The constant oligonucleotide (p GGAGAAGTCTGCCGTTACTGCGCTCTAGAAC-TAGTGGATC$(T)_{50}$-$NH_2$, SEQ ID NO: 3) is synthesized with a 3' amino group modification (Midland Certified Scientific Reagent Co.) and is phosphorylated enzymatically on the 5' end using polynucleotide kinase (New England Biolabs) according to the manufacturer's specifications. The sickle cell and wild-type allele specific oligonucleotides $NH_2$-$(T)_{50}$CGCTCTAGAACTAGTGGATC<u>ATGGTGCACCTGACTCCTGT</u> (SEQ ID NO: 4) and $NH_2$-$(T)_{50}$CGCTCTAGAACTAGTGGATC<u>ATGGTGCACCTGACTCCTGA</u> (SEQ ID NO: 5) are synthesized with 5' amino group modifications. Note that the oligonucleotides are bipartite: one part (distal to the amino modification, underlined) hybridizes to the globin gene and the other part (proximal to the amino modification) functions as a spacer or tether. Incorporating a spacer between the end of oligonucleotide that binds to the particle (via the amino group) and the part of the oligonucleotide that is destined to hybridize to genomic DNA may improve hybridization efficiency.
Binding Oligonucleotides to Particles.

Oligonucleotides, modified by terminal amino groups, are covalently linked to particles using tosyl chemistry as described previously (Example 10). The constant oligonucleotide is linked via its 3' amino group to tosyl activated magnetic particles (2.8 μm; Dynal; cat. num 140.03). The sickle cell allele specific oligonucleotide is linked to red fluorescent particles (200 nm; Molecular Probes; catalogue #F-8811) and the wild-type allele specific oligonucleotide is linked to green fluorescent particles (200 nm; Molecular Probes; catalogue num. F-8810) via their 5' amino groups. After linkage, washing, and blocking, the oligonucleotide coated particles are mixed together at a final concentration of 2%.
Homogenous Oligonucleotide Ligation Assay.

Human DNA is purified from the buffy coat blood fraction (Sambrook, J, et al., Molecular Cloning A Laboratory Manual (Cold Spring Harbor Press, Cold Spring Harbor, N.Y., 2001)). Purified human genomic DNA (1 μg in 12 μl EE) is denatured by heating at 100° C. for 3 min, quick-chilled on an ice bath, and then mixed with 5 μl of the oligonucleotide-coated particle mixture, and 2 μl of 10× ligation buffer (New England Biolabs) and allowed to anneal at 50° C. for 1 hr. T4 DNA ligase (1 μl 400 u/μl; New England Biolabs) is added and the ligation reaction is allowed to proceed at 37° C. for 1 hr. A negative control sample is placed in another well of a dish. The negative control is identical in composition to the experimental sample except that EE is substituted for the human DNA. The negative control is processed in the same way as the experimental sample. The samples are diluted to 200 μl by adding EE (120 μl). Black ink (50 μl; Black No. 17, Pelikan, Hanover, Germany) is added to the well of a 96-well microtiter dish with an optically clear bottom (Greiner Labs; catalogue number 665097). The microtiter dish is placed on a flat magnet (Dexter Magnetics, LifeSep, 96F) for 15 minutes. The dish is then gently moved into position over a CCD imager (FIG. 3), and the bottom of the wells containing the assay and control are imaged successively. The images are then analyzed using an image analysis software package (Image-Pro Plus software, version 4.1; Media Cybernetics) as in Example 2. The number of green and red particles imaged on the bottom of the negative control sample represents the background particle count. These numbers are subtracted from the number of similarly colored particles imaged on the bottom of the experimental sample. The ratio of red particles to green particles determines the genotype at the sickle cell locus. If the ratio of green particles (wild-type allele) to red particles (mutant allele) is high (<90%), the genotype is homozygous wild-type. If the ratio is small (<10%) the genotype is homozygous for the sickle cell allele. Finally, if the ratio is approximately 1:1, the genotype is heterozygous for the sickle cell allele.
Variations.

Numerous variations of this scheme can be incorporated. Amplification products of genomic DNA or cellular RNA can also be used as the template to which the oligonucleotide probes anneal prior to ligation. Alternative labeling strategies can also be used. For example, the selection moiety (magnetic particles in the example) can be replaced by a hapten (e.g., biotin or digoxygenin) which can function as a selection moiety by using streptavidin or anti-digoxygenin antibodies as a capture reagent (Immobilized, for example, on a surface or a magnetic particle). Similarly, the signaling moiety can have one or more of various signaling characters (e.g., fluorescence, chemiluminescence, bioluminescence, radio frequency, size, etc.). As is true for the selection moiety, the signaling moiety can be directly (e.g., covalently) or indirectly linked to the allele specific oligonucleotide. For example, the allele specific oligonucleotide could be modified by biotin and fluorescently labeled streptavidin could be indirectly bound and used as the signaling moiety. Alternatively, a signaling moiety, such as a fluorescent particle or a selection moiety, such as a magnetic particle, could be coated with a tag sequence that allows the particle to bind by nucleic acid hybridization to a tag complement moiety on the oligonucleotide that hybridizes to genomic DNA. When, as in this latter case, the labeling is indirect, assays can be constructed in which the ligation to genomic DNA is carried out first, and then the labeling and/or signaling moieties are associated with the oligonucleotides (ligated and unligated) afterwards. This method may be advantageous when using large labeling moieties that could sterically or kinetically lower the efficiency of the ligation reaction. Finally, genomic or cellular RNA can be used as the template on which ligation takes place.

Example 15. Non-Amplified Multiplex SNP Analysis Using a Lateral Flow Format and Non-Magnified Large Area Imaging An important goal of modern medical genetics and pharmacogenomics is to obtain genomic profiles of patients rapidly. Genetic markers can be an early warning of disease (e.g., breast cancer or Huntington's disease) or can indicate to which medications a patient is likely to respond favorably. Single-nucleotide polymorphisms (SNPs) are medically important genetic markers because of their abundance in the genome and because many human genetic diseases are caused by point mutations.

Development of technology that is rapid, highly multiplexed, and inexpensive is a current aim of applied medical genetics. In this example, the invention is used to create a test with these attributes. The assay—which does not require DNA amplification—scans a human DNA sample for nucleotide polymorphism genotypes in 3 different genes (β-globin, α-antitrypsin, and cystic fibrosis transmembrane conductance regulator (CFTR)).

Technical overview.

As in the previous example, this assay uses the oligonucleotide ligation assay to test for SNP alleles. However, in this example, a lateral flow test is used to detect the ligated products. This format facilitates testing for numerous target molecules (in this case SNPs) using only a single signaling moiety. The ability to detect many target SNP alleles in this format arises from the potential to distinguish targets by their hybridization to distinct capture oligonucleotides immobilized at known sites on the membrane.

The test can be divided into two stages, which are diagrammed in FIG. 18 and FIG. 19. The first stage is an oligonucleotide ligation assay (top of FIG. 18). As in the previous example, oligonucleotide pairs, designed for allele-specific ligation, are hybridized to denatured genomic DNA and ligated. In the second stage of the assay, ligated single-stranded products are applied to a lateral flow device where they encounter and hybridize to complementary capture oligonucleotide tags (bottom of FIG. 18). The individual captured oligonucleotides are imaged using a CCD imager by virtue of bound particles that emit a high-intensity chemiluminescent signal (FIG. 19).

Oligonucleotides.

In this example, nucleotide polymorphisms are genotyped in 3 genes: β-globin, α-antitrypsin, and CFTR. A set of oligonucleotides is synthesized for each locus to be genotyped. As in the previous example, each set comprises one constant oligonucleotide and one or more allele-specific oligonucleotides. When hybridized to the corresponding strand of genomic DNA, the constant oligonucleotide and the one allele-specific oligonucleotide that complements the nucleotide polymorphism are ligated.

The oligonucleotide sets are designed analogously to the set in the previous example except for the following differences. Each allele-specific oligonucleotide is bipartite with one part corresponding to a genomic sequence, as before. However, in this example the allele-specific oligonucleotide is synthesized with an adjacent unique tag sequence.

To facilitate equivalent hybridization of multiple probes in a single reaction, oligonucleotides are designed so that the melting temperatures ($T_m$; see definitions) of the functional segments with their complements are approximately equal. The multi-partite oligonucleotides are preferably about 20 nucleotides long with $T_m$'s equal to 60°±2°. The target mutations and oligonucleotide ligation assay with oligonucleotides similar to those in Table 3 have been described previously (Nickerson, D. A., et al., Proc Natl Acad Sci USA 87: 8923-7, 1990).

TABLE 3

Oligonucleotides for genotyping nucleotide polymorphisms in Example 15.

| gene | target polymorphism[a] | allele-specific oligonucleotides[b,c] | constant oligonucleotide[b] | capture oligonucleotide[b,d] |
|---|---|---|---|---|
| β-globin | βA | CGCTCTAGAACTAGTGGATC-TGGTGCACCTGACTCCTGA (SEQ ID NO:6) | pGGAGAAGTCTGCCGTTACTG-b (SEQ ID NO:12) | GATCCACTAGTTCTAGAGCG (SEQ ID NO:15) |
|  | βS | TCTCGAGGTCGACGGTATC-TGGTGCACCTGACTCCTGT (SEQ ID NO:7) |  | GATACCGTCGACCTCGAGA (SEQ ID NO:16) |
| α1 antitrypsin | M | CATCGATACCGTCGACCTC-GCTGTGCTGACCATCGACG (SEQ ID NO:8) | pAGAAAGGGACTGAAGCTGCT-b (SEQ ID NO:13) | GAGGTCGACGGTATCGATC (SEQ ID NO:17) |
|  | Z | GCAAGTTCAGCCTGGTTAAG-GCTGTGCTGACCATCGACA (SEQ ID NO:9) |  | ATTAACCAGGCTGAACTTGC (SEQ ID NO:18) |
| CFTR | non-F508 | GCCTTTTGCTCACATGTTCTT-CACCATTAAAGAAAATATCATCTT (SEQ ID NO:10) | pTGGTGTTTCCTATGATGAATATA-b (SEQ ID NO:14) | AAGAACATGTGAGCAAAGGC (SEQ ID NO:19) |

TABLE 3-continued

Oligonucleotides for genotyping nucleotide polymorphisms in Example 15.

| gene | target polymorphism[a] | allele-specific oligonucleotides[b,c] | constant oligonucleotide[b] | capture oligonucleotide[b,d] |
|------|------------------------|---------------------------------------|------------------------------|-------------------------------|
|      | F508                   | AAGGCGATTAAGTTGGGTAAC-GGCACCATTAAAGAAAATATCAT (SEQ ID NO:11) |                              | GTTACCCAACTTAATCGCCTT (SEQ ID NO:20) |

[a]Nomenclature follows that in (Nickerson, et al., 1990 supra).
[b]oligonucleotide sequences are written in the 5' to 3' orientation; b = biotin; p = 5' phosphate
[c]Genomic sequences are underlined; sequences that are not underlined are tag sequences.
[d]Capture oligonucleotides are complementary to the corresponding tag sequence moieties in the allele-specific oligonucleotides (i.e., the segments that are not underlined in the allele-specific oligonucleotides)

Binding capture oligonucleotides to a membrane.

Capture oligonucleotides (Table 3) are applied and bound to plastic-backed nitrocellulose filters (3 μm pore size; Schleicher & Schuell) as described previously (Rule, G. S., et al., Clinical Chemistry 42: 1206-9, 1996), except that, in the present example, multiple capture oligonucleotides are used. As described by Rule et al., the first line is applied 1 cm from the bottom edge of the filter. Subsequent lines of capture oligonucleotides are applied in parallel lines separated by a space of 3 mm (moving away from the bottom edge of the filter and the previous line). Filters are cut into 0.5 mm×8 cm strips (oligonucleotide lines run perpendicular to the long dimension).

Oligonucleotide ligation assay.

The oligonucleotide mixture (1 nM, each oligonucleotide) and human genomic DNA (1 μg) are combined in 14 μl ligation buffer (see definitions). The mixture is denatured by heating to 95° C. (3 min) in a thermal cycler (Perkin Elmer, GeneAmp PCR System 9700) and then cooled (at 5% of the maximum down-ramp rate) to 37° C. T4 DNA ligase (1 μl of 400 u/μl enzyme; New England Biolabs; enzyme concentration expressed as cohesive end units) is added to the reaction which is then incubated at 37° for 1 hr.

The reaction is stopped and the DNA is denatured by heating to 100° C. in a heat block for 1 minute. The sample is quick chilled at 0° C. by immersion in an ice bath and then diluted to 150 μl with HYB (see definitions).

Binding Alkaline Phosphatase to Avidin-Coated Particles.

Streptavidin-coated particles (0.95 μm diameter; Bangs Labs; #CP01N) are coated with biotinylated alkaline-phosphatase (Pierce; #29339) so that only about half of the maximum number of alkaline phosphatase molecules are bound. Such particles retain the ability to bind to biotinylated target molecules via the free streptavidin moieties. Partial coating is accomplished by incubating the streptavidin-coated particles with biotinylated alkaline phosphatase at a ratio of about $1 \times 10^4$ biotinylated alkaline phosphatase molecules per particle. The ratio is empirically established for each lot of particles by determining a minimum ratio of biotinylated alkaline phosphatase to particles required to saturate the biotinylated alkaline phosphatase binding sites on the particles. A fraction of this ratio (e.g., ½) is then used to coat the particles. The minimum ratio of biotinylated alkaline phosphatase to particles required to saturate the particles is determined by binding serial dilutions of biotinylated alkaline phosphatase with a fixed number of particles, eliminating free biotinylated alkaline phosphatase by spin filtration (spinX; Costar; #8161), recovering the particles, and measuring the chemiluminescent signal of single particles on nylon filters (GeneScreen; NEN) using CDP-star (CDP-Star; NEN) and X-ray film luminography.

Streptavidin-coated particles ($2 \times 10^9$ particles) are partially coated with biotinylated alkaline phosphatase using the biotinylated alkaline phosphatase:particle ratio established as described above (e.g., $10^4$). The coating reaction (100 μl) is carried out for 1 hr at room temperature in EEN (1×EE, 500 mM NaCl)/0.1% BSA. Particles are washed (3×500 μl EEN) using spin filtration (spinX; costar; #8161) and collected in EEN (200 μl).

Chromatography and Detection.

Chromatography is carried out at 37° C. according to the method of Rule et al. (1996, supra). The oligonucleotide ligation assay (150 μl) is placed in a 10×75 mm polystyrene test tube. A nitrocellulose strip is then placed in the tube so that the bottom of the strip (the first oligonucleotide stripe applied to the strip is 1 cm above the bottom edge) is resting in the oligonucleotide ligation assay solution. After 20 minutes, the strip is removed from the tube and washed 3 times (5 minutes each wash) in HYB solution (50° C.). The strips are covered with particles ($10^8$ biotinylated alkaline phosphatase-coated particles in 1 ml EEN) and allowed to incubate for 1 hr at room temperature. Free particles are washed from the strips (5×10 ml EEN washes with vigorous agitation). Strips are covered with CDP-Star (NEN) and luminographed using x-ray film. Before exposing, the corners of the strips are distinctly marked using fluorescent tape (Glogos™ II Autorad Markers, Stratagene Cat #420201) so that the exposed x-ray film can be aligned in register with a template that indicates the position of the various SNP lines on the strip. Chemiluminescent signal arising from binding of the particles to single captured SNP molecules indicates the presence of particular SNP genotypes in the target DNA.

Alternative Embodiments.

Other types of labels could be used including fluorescent and light-scattering labels. Similarly, a wide range of instrumentation can be used to detect the signal (e.g., CCD cameras, chromogenic detection, instant film, etc.). Other types of substrates could be used such as non-bibulous substrates (e.g., glass slides). Flow through test formats are also possible. The assay could also use a microfluidic format (using, for example, the Flow-Thru Chip™ system; Genelogic) rather than using bibulous filter in the lateral flow assay. In this case, the capture probes are immobilized in an addressable geometry (i.e., in a known order) on the walls of a micro-machined channel through which the (ligated and unligated) oligonucleotide probes flow.

OTHER EMBODIMENTS

All patents, patent applications, and publications referenced in this application are hereby incorporated by reference. Other embodiments of the invention will be apparent to those skilled in the art from consideration of the specification and practice of the invention disclosed herein. It is intended that the specification and examples be considered as exemplary only, with a true scope and spirit of the invention being indicated by the following claims. Examples of other embodiments that may be adapted to the methods described herein are found in U.S. application Ser. No. 10/237,010, entitled "RAPID AND SENSITIVE DETECTION OF CELLS AND VIRUSES", filed Sep. 6, 2002 and U.S. application Ser. No. 10/236,107, entitled "RAPID AND SENSITIVE DETECTION OF REPLICATING CELLS", filed Sep. 6, 2002, each of which is hereby incorporated by reference.

Other embodiments are in the claims.

What is claimed is:

1. A method for detecting target molecules in a sample, wherein said method comprises the steps of:
   a. contacting said target molecules with labeling particles at a labeling ratio of less than 100 to form individual target molecule:labeling particle complexes, wherein said labeling particles have photonic signaling character,
   b. concentrating the target molecule:labeling particle complexes in a liquid phase in a container comprising an optically transparent detection surface having a longest linear dimension of greater than 1 mm so that the complexes are deposited in a detection zone that is a volume with one face defined by the detection surface and an opposite face spaced from the detection surface by the depth of field of an optical detection system, thereby separating the complexes from unbound labeling particles lying outside of said detection zone, wherein said concentrating comprises either (i) binding said complexes to said detection surface or (ii) applying a selection force to said complexes, wherein said complexes further comprise a selection moiety bound to said target molecule; and
   c. simultaneously optically detecting individual target molecule:labeling particle complexes in the detection zone with the optical detection system, thereby detecting said target molecules, wherein said detecting does not entail magnification of more than 5×, wherein said labeling particles that do not bind to said targets are not removed from said container prior to said detecting wherein the container comprises a colloidal or soluble substance that absorbs the photonic signal emitted by said labeling particles, and wherein said substance is present at a concentration sufficient to prevent the detection of unbound labeling particles not in said detection zone and sufficient to allow the detection of the labeling particles in the complexes deposited in the detection zone.

2. The method of claim 1, wherein said complexes are randomly dispersed in said detection zone at a density of less than 10 complexes per mm$^2$ of the detection surface.

3. The method of claim 2, wherein said complexes are randomly dispersed in said detection zone at a density of less than 1 complex per mm$^2$ of the detection surface.

4. The method of claim 1, wherein said detecting does not entail magnification of more than 2×.

5. The method of claim 4, wherein said detecting does not entail magnification of more than 1×.

6. The method of claim 5, wherein said detecting does not entail magnification.

7. The method of claim 1, wherein said target molecules are proteins.

8. The method of claim 1, wherein said target molecules are nucleic acids.

9. The method of claim 1, wherein said target molecules have a molecular weight of less than 100 kD.

10. The method of claim 9, wherein said target molecules have a molecular weight of less than 10 kD.

11. The method of claim 10, wherein said target molecules have a molecular weight of less than 1 kD.

12. The method of claim 1, wherein said detecting detects and identifies more than one non-overlapping category of target molecules.

13. The method of claim 1, wherein said target molecules comprise category-specific binding sites and said category-specific binding sites on said target molecules are sites that bind specifically to natural or recombinant antibodies or aptamers.

14. The method of claim 1, wherein said target molecules comprise category-specific binding sites and said category-specific binding sites on said target molecules are sites that bind specifically to DNA, RNA, or PNA probes.

15. The method of claim 1, wherein said target molecules comprise category-specific binding sites and said the category-specific binding sites on said target molecules are or are immediately adjacent to nucleic acid polymorphisms including single nucleotide polymorphisms.

16. The method of claim 1, wherein said sample comprises a fluid or tissue obtained from a multicellular organism.

17. The method of claim 16, wherein said sample comprises the bodily fluids or tissues of an animal.

18. The method of claim 17, wherein said sample is derived from a human.

19. The method of claim 17, wherein said sample is derived from a non-human vertebrate.

20. The method of claim 17, wherein said sample is selected from the group consisting of: respiratory, urogenital, reproductive tract, central nervous system, urine, blood, dermal, plasma, serum, saliva, wound tissue, wound exudate, biopsy, feces, and solid tissue samples.

21. The method of claim 1, wherein said sample is derived from a plant.

22. The method of claim 1, wherein said sample is obtained by sampling environmental air or water, or surfaces, objects, or organisms exposed to the environment.

23. The method of claim 1, wherein said sample is selected from the group consisting of: raw, finished or in-process material in the manufacture pharmacological, cosmetic, blood, or other products for topical or internal use in humans or animals; raw, in-process or finished material in the manufacture of foods or beverages; and chemical products.

24. The method of claim 1, wherein in step (b) said complexes are deposited on a detection surface by magnetic selection, centrifugation, or settling.

25. The method of claim 24, wherein said magnetic selection comprises contacting said sample with magnetic particles that are conjugated to category-binding molecules.

26. The method of claim 24, wherein said target molecules are contacted in the liquid phase with target-molecule specific selection moieties that have an average density greater than the average density of said liquid phase and are subsequently deposited on said detection surface using gravitational, centrifugal, or centripetal force.

27. The method of claim 1, wherein said sample is treated to liquefy and/or homogenize said sample.

28. The method of claim 1, wherein said contacting occurs in a liquid phase.

29. The method of claim 1, wherein said contacting occurs at an interface between a liquid and solid phase.

30. The method of claim 1, wherein said sample is treated to remove substances or objects other than said target molecules.

31. The method of claim 1, wherein said target molecules are immobilized on the detection surface prior to said contacting.

32. The method of claim 1, wherein said target molecules are specifically bound in the detection zone by category-binding molecules that are bound to the matrix or substrate of the detection zone.

33. The method of claim 1, wherein said target molecules are specifically bound in the detection zone by forming chemical bonds to matrix or substrate of the detection zone.

34. The method of claim 1, wherein said target molecules are immobilized in said detection zone by a process selected from the group consisting of air drying, heat fixation, and chemical fixation.

35. The method of claim 1, wherein said target molecules comprise category-specific binding sites and said sample is treated so that the category-specific binding sites on said target molecules become accessible to contact by said labeling particles.

36. The method of claim 1, wherein said sample is subdivided into individual aliquots that are tested, in parallel, for the presence of different non-overlapping categories of target molecules.

37. The method of claim 36, wherein each of said aliquots is contacted with a population of labeling particles that is conjugated to a different non-overlapping family of category-binding molecules.

38. The method of claim 36, wherein said sample is contacted successively with distinct families of category-binding molecules that specifically bind to non-overlapping categories of target-entities.

39. The method of claim 1, wherein said detection surface is selected from the group consisting of solid glass, solid plastic, the surface of the wells of microtiter plates, bibulous membranes, plastic strips, the surfaces of capillary tubes, the surfaces of microfluidic chambers, and the surfaces of microfluidic channels.

40. The method of claim 1, wherein said method is automatically repeated on a series of samples.

41. The method of claim 40, wherein said samples are automatically loaded into an instrument that contains a detector for detecting said complexes.

42. The method of claim 40, wherein said samples are automatically deposited in a series of detection zones that are physically associated and that are automatically and successively loaded into an instrument that contains a detector for detecting said complexes.

43. The method of claim 1, wherein said complexes are illuminated to generate a detectable signal.

44. The method of claim 43, wherein said method detects light emitted, scattered, reflected, or absorbed as a result of said illumination of said complexes.

45. The method of claim 43, wherein said detecting detects fluorescence.

46. The method of claim 1, wherein said detecting detects chemiluminescence.

47. The method of claim 43, wherein said complexes are illuminated by one or more lasers.

48. The method of claim 43, wherein said complexes are illuminated by one or more light-emitting diodes.

49. The method of claim 43, wherein said complexes are illuminated by a source of white-light.

50. The method of claim 43, wherein said complexes are illuminated using one or more optical filters adapted for illuminating said sample with light of a wavelength appropriate for detecting said complexes.

51. The method of claim 44, wherein said emitted, scattered, transmitted, or absorbed light is detected using optical filters adapted to detect the signals derived from the illumination of said complexes.

52. The method of claim 1, wherein said detecting does not employ illumination.

53. The method of claim 1, wherein said detecting detects thermal radiation.

54. The method of claim 1, wherein said detecting detects optical absorbance.

55. The method of claim 54, wherein said optical absorbance is in the infrared region.

56. The method of claim 1, wherein said detecting detects fluorescence polarization.

57. The method of claim 1, wherein said detecting detects optical reflectance.

58. The method of claim 1, wherein said detecting detects light scattering.

59. The method of claim 1, wherein said detecting detects Raman scattering.

60. The method of claim 1, wherein said labeling particles are less than 20 microns in size.

61. The method of claim 60, wherein said labeling particles are less than 10 microns in size.

62. The method of claim 61, wherein said labeling particles are less than 5 microns in size.

63. The method of claim 62, wherein said labeling particles are less than 1 micron in size.

64. The method of claim 63, wherein said labeling particles are less than 100 nm in size.

65. The method of claim 64, wherein said labeling particles are less than 10 nm in size.

66. The method of claim 1, wherein said labeling particles are latex particles, silica particles, quantum dots, resonance light scattering particles, up-converting phosphors, or particles composed chiefly of gold or silver.

67. The method of claim 1, wherein said labeling particles are coated with enzymatic signaling moieties.

68. The method of claim 67, wherein said labeling particles comprise enzymatic signaling moieties at an average density of greater than or equal to 2 enzymatic signaling moieties per cubic micron of particle volume.

69. The method of claim 1, wherein said labeling particles comprise signaling moieties are alkaline phosphatase or horseradish peroxidase enzymes.

70. The method of claim 1, wherein said labeling particles bind to category-binding molecules that have been previously contacted with the sample.

71. The method of claim 1, wherein said labeling particles comprise signaling moieties are selected from the group consisting of organic fluorophores, up-regulated phosphors, lanthanides, quantum dots, and enzymes that generate fluorescent product from non-fluorescent substrates.

72. The method of claim 1, wherein said labeling particles comprise signaling moieties are particles dyed with or conjugated to signaling moieties that have fluorescent signal character and that are selected from the group consisting of: organic fluorophores, up-regulated phosphors, lanthanides, quantum dots, and enzymes that generate fluorescent product form non-fluorescent substrates.

73. The method of claim 1, wherein said labeling particles comprise signaling moieties with fluorescent signaling character.

74. The method of claim 1, wherein said labeling particles comprise signaling moieties with chemiluminescent signaling character.

75. The method of claim 74, wherein said signaling moieties are acridinium esters.

76. The method of claim 1, wherein said labeling particles comprise signaling moieties with chromogenic signaling character.

77. The method of claim 1, wherein said labeling particles comprise signaling moieties with light scattering character.

78. The method of claim 1, wherein step (a) comprises contacting said sample with labeling particles comprising category-binding molecules under conditions that allow the formation of complexes between said category-binding molecules and category-specific binding sites on said target molecules.

79. The method of claim 78, wherein said category-binding molecules comprise antibodies.

80. The method of claim 78, wherein said category-binding molecules comprise aptamers.

81. The method of claim 78, wherein said category-binding molecules comprise nucleic acids or peptide nucleic acids.

82. The method of claim 78, wherein said category-binding molecules comprise ligands.

83. The method of claim 78, wherein said category-binding molecules comprise molecules with molecular weights less than 100 kD.

84. The method of claim 83, wherein said category-binding molecules comprise molecules with molecular weights less than 10 kD.

85. The method of claim 84, wherein said category-binding molecules comprise molecules with molecular weights less than 1 kD.

86. The method of claim 1, wherein said labeling particles comprise different populations, wherein each population is conjugated to a different non-overlapping family of category-binding molecules.

87. The method of claim 86, wherein each of said populations binds specifically to a category of target molecules that also binds specifically to a corresponding, second family of category-binding molecules that is stably bound to a section of the detection zone, wherein each of said corresponding, second families is bound at a distinct site that can be distinguished by said detecting.

88. The method of claim 87, wherein each of said populations of labeling particles has the same signaling class and signature.

89. The method of claim 86, wherein each of said populations has a distinct signaling signature or signaling class.

90. The method of claim 89, wherein said method comprises optical filters adapted to discriminate between the signal signatures of said populations of labeling particles.

91. The method of claim 86, wherein said families of category-binding molecules have a family complexity that is greater than 1.

92. The method of claim 86, wherein said families of category-binding molecules have a family complexity $\geq 5$.

93. The method of claim 86, wherein said families of category-binding molecules have a family complexity $\geq 10$.

94. The method of claim 86, wherein said families of category-binding molecules have a family complexity $\geq 20$.

95. The method of claim 1, wherein the container has a bar code or equivalent label for tracking the sample automatically.

96. The method of claim 1, wherein the detection surface has registration marks to facilitate alignment of multiple images of the same surface.

97. The method of claim 1, wherein said method detects control marks or control cells in a specified region of the detection zone.

98. The method of claim 1, wherein said detecting comprises use of a photoelectric detector.

99. The method of claim 1, wherein said detecting comprises use of a photoelectric array detector.

100. The method of claim 99, wherein said photoelectric detector comprises a CCD or CMOS detector.

101. The method of claim 44, wherein detecting of said emitted, scattered, or absorbed light does not employ an image intensifier.

102. The method of claim 1, wherein said detecting comprises use of a photomultiplier tube detector.

103. The method of claim 1, wherein said detecting comprises use of a photodiode detector.

104. The method of claim 1, wherein the detecting comprises use of photosensitive film.

105. The method of claim 1, wherein said detecting comprises direct visual detection.

106. The method of claim 1, wherein the number of target molecules is inferred from said detecting by analyzing images acquired by said detecting.

107. The method of claim 1, wherein the category of target molecules is inferred from said detecting using image analysis software.

108. The method of claim 107, wherein said image analysis software further comprises functions for discerning the signals generated by said complexes from other signals.

109. The method of claim 1, wherein said sample is obtained from raw, in-process, or finished material in the manufacture of medical or in vitro diagnostic devices; industrial surfaces; instrumentation; or machinery.

110. The method of claim 1, wherein the liquid phase is aqueous.

* * * * *